US008071761B2

US 8,071,761 B2

(12) United States Patent
Tsien et al.

(10) Patent No.: US 8,071,761 B2
(45) Date of Patent: Dec. 6, 2011

(54) SUBSTRATES FOR BETA-LACTAMASE AND USES THEREOF

(75) Inventors: Roger Y. Tsien, La Jolla, CA (US); Gregor Zlokarnik, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 808 days.

(21) Appl. No.: 11/606,642

(22) Filed: Nov. 29, 2006

(65) Prior Publication Data

US 2007/0184513 A1 Aug. 9, 2007

Related U.S. Application Data

(63) Continuation of application No. 10/280,482, filed on Oct. 24, 2002, now Pat. No. 7,157,575, which is a continuation of application No. 09/481,756, filed on Jan. 11, 2000, now Pat. No. 6,472,205, which is a continuation of application No. 08/727,616, filed on Oct. 15, 1996, now Pat. No. 6,291,162, which is a continuation of application No. PCT/US96/04059, filed on Mar. 20, 1996, which is a continuation-in-part of application No. 08/407,544, filed on Mar. 20, 1995, now Pat. No. 5,741,657.

(51) Int. Cl.
*C07D 501/14* (2006.01)
(52) U.S. Cl. .................................. 540/222; 540/205
(58) Field of Classification Search .................. None
See application file for complete search history.

(56) References Cited

U.S. PATENT DOCUMENTS

| 4,234,683 | A | 11/1980 | McMillan |
|---|---|---|---|
| 4,383,032 | A | 5/1983 | Stahl et al. |
| 4,448,880 | A | 5/1984 | Schindler et al. |
| 4,740,459 | A | 4/1988 | Chen et al. |
| 4,760,018 | A | 7/1988 | Charm |
| 4,764,462 | A | 8/1988 | Bredeehorst et al. |
| 4,978,613 | A | 12/1990 | Bieniarz et al. |
| 5,162,524 | A | 11/1992 | Farina et al. |
| 5,264,346 | A | 11/1993 | Chen |
| 5,338,843 | A | 8/1994 | Quante et al. |
| 5,501,979 | A | 3/1996 | Geller et al. |
| 5,514,561 | A | 5/1996 | Quante et al. |
| 5,583,217 | A | 12/1996 | Quante et al. |
| 5,593,866 | A | 1/1997 | Hancock et al. |
| 5,639,596 | A | 6/1997 | Bornkamm et al. |
| 5,741,657 | A | 4/1998 | Tsien et al. |
| 5,955,604 | A | 9/1999 | Tsien et al. |
| 6,291,162 | B1 | 9/2001 | Tsien et al. |
| 6,472,205 | B1 | 10/2002 | Tsein et al. |

FOREIGN PATENT DOCUMENTS

| EP | 0 053 541 | 6/1982 |
|---|---|---|
| EP | 0 354 757 | 5/1990 |
| JP | 0 075 184 94 | 2/1975 |
| WO | WO 91/13160 | 9/1991 |
| WO | WO 96/30540 | 10/1996 |
| WO | WO 97/19180 | 5/1997 |
| WO | WO 97/19183 | 5/1997 |

OTHER PUBLICATIONS

Alam, et al., "Reporter Genes: Application to the Study of Mammalian Gene Transcripion", Analytical Biochemistry, 188, 245-254 (1990).
Ambler R.P., "The structure of .beta.-lactamases", Phil. Trans. R. Soc. Lond. B 289, 321-331 (1980).
Berlman I.B., "Energy transfer parameters of aromatic compounds", Academic Press New York and London (1973).
Bojarski C. et al., "Energy Transfer and Migration in Fluorescent Solutions", Photochemistry and Photophysics, edited by Rabek, J.F. Boca Raton: CRC Press, Inc., 1990, pp. 1-57.
Broach et al., "High-throughput screening for drug discovery", Nature, vol. 384, Nov. 7, 1996, pp. 14-16.
Bundgaard, H. "Design of prodrugs: Bioreversible derivatives for various functional groups and chemical entities", Elsevier Science Publishers (1985).
Bundgaard H., "Design of Bioreversible Drug Derivatives and the Utility of the Double Prodrug Concept", New York Pergamon Press (1987).
Bunnell C.A. et al., "Industrial manufacture of cephalosporius", Beta-Lactam Antibiotics for Clinical Use. Series: Clinical Pharmacology vol. 4, edited by Queener, S.F., Webber, J.A. and Queener, S.W., New York: M. Dekker, 1986, pp. 255-283.
Bush K., "Methodology for the Study of .beta.-Lactamases", Antimicrobial Agents and Chemotherapy, Jul. 1986, pp. 6-10 (1986).
Cartwright, Charles P. et al., "Use of .beta.-Lactamase as a Secreted Reporter of Promoter Function in Yeast", Yeast, vol. 10:497-508 (1994).

(Continued)

*Primary Examiner* — Elli Peselev
(74) *Attorney, Agent, or Firm* — Morgan, Lewis & Bockius LLP

(57) ABSTRACT

Substrates for β-lactamase of the general formula I

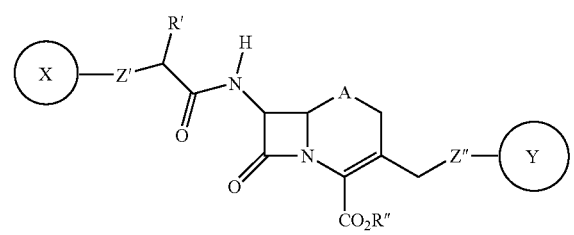

in which one of X and Y is a fluorescent donor moiety and the other is a quencher (which may or may not re-emit); R' is selected from the group consisting of H, lower (i.e., alkyl of 1 to about 5 carbon atoms) and $(CH_2)_nOH$, in which n is 0 or an integer from 1 to 5; R" is selected from the group consisting of H, physiologically acceptable metal and ammonium cations, $-CHR^2OCO(CH_2)_nCH_3$, $-CHR^2OCOC(CH_3)_3$, acylthiomethyl, acyloxy-alpha-benzyl, delta-butyrolactonyl, methoxycarbonyloxymethyl, phenyl, methylsulphinylmethyl, beta-morpholinoethyl, dialkylaminoethyl, acyloxyalkyl, dialkylaminocarbonyloxymethyl and aliphatic, in which $R^2$ is selected from the group consisting of H and lower alkyl; A is selected from the group consisting of S, O, SO, $SO_2$ and $CH_2$; and Z' and Z" are linkers for the fluorescent donor and quencher moieties. Methods of assaying β-lactamase activity and monitoring expression in systems using β-lactamase as a reporter gene also are disclosed.

12 Claims, 17 Drawing Sheets

OTHER PUBLICATIONS

Cartwright, Charles P. et al., Yeast 8:261-272, 1992.

Castagnoli L. et al., "The phasmid as a tool for phasmid genetics", Genet. Res. 40: 217-231 (1982).

Castelli, L.A. et al., "High-level secretion of correctly processed .beta.-lactamase from *Saccharomyces cerevisiae* using a high-copy-number secretion vector", Gene 142 (1994) pp. 113-117.

Chalfie et al., "Green Fluorescent Protein as a Marker for Gene Expression," Science, vol. 263, Feb. 11, 1994.

Chang, Y.H et al., "Altering enzymatic activity: Recruitment of carboxypeptides activity into an RTEM .beta.-lactamase/penicillin-binding protein 5 chimera", Proc. Nat. Acad. Sci., USA vol. 87, pp. 2823-2827, Apr. 1990.

Christensen, M. et al., ".beta.-Lactamases as fully efficient enzymes", Biochem. J. (199) 266, 853-861.

Cuchural et al., J. Antimicrobial Chemother. 22:785-790, 1988.

Daehne W.V. et al., "Acyloxymethyl Esters of Ampicillin", J. Med. Chem. 13:607-612 (1970).

Darnell et al., "The Architecture of Lipid Membranes", Molecular Cell Biology, 1986, 570-573.

Davis, Bernhard D. et al.,"Bacterial Physiology", Microbiology, 3.sup.rd Edition, 1980, pp. 82-91.

De Sutter et al., "A Bifunctional Murine:Human Chimeric Antibody With One Antigen-Binding Arm Replaced by Bacterial .beta.-Lactamase", Mol. Immunol. vol. 31, No. 4 pp. 261-267 (1994).

dos Remedios, C.G. et al., "Fluorescence resonance energy transfer measurements of distances in actin and myosin. A critical evaluation", J. Muscle Research and Cell Motility, 8:97-117.

Ferres H., "Pro-drugs of .beta.-lactam antibiotics", Chem. Ind., Jun. 1980, pp. 435-440.

Forster V.T., "Zwischenmolekulare Energiewanderung and Fluoreszenz", Ann. Physik 2:55-75.

Forster, Annalen. Der Physik. G. Folge. Band 2. (1948).

Garcia, Pablo D. et al., "Wild Type Mutant Signal Peptides of *Escherichia coli* Outer Membrane Lipoprotein Interact with Equal Efficiency with Mammalian Recognition Particle", The Journal of Biological Chemistry, vol. 262, No. 20, Issue of Jul. 15, 1987, pp. 9463-9468.

Gorman, C.M. et al., "Recombinant Genomes which Express Chloramphenicol Acetyltransferase in Mammalian Cells", Mol. Cell. Bio. 2:1044-1051 (1982).

Jansen, A.B.A. et al., "Some Novel Penicillin Derivatives," J. Chem. Soc., 2127-2132 (1965).

Jones, R.N. et al., "In Vitro Evaluation of Pyridine-2-Azo-p-Dimethylaniline Cephalosporin, a New Diagnostic Chromogenic Reagent, and Comparison with Nitrocefin, Cephacetrile, and Other Beta-Lactam Compounds", J. Clin. Microbiol., 15:677-683 (1982).

Jones R.N., "In Vitro Evaluation of CENTA, a New Beta-Lactamase-Susceptible Chromogenic Cephalosporing Reagent", J. Clin. Microbiol., 15:954-958 (1982).

Kadonaga J.T. et al., "The Role of the .beta.-Lactamase Signal Sequence in the Secretion of Proteins by *Escherichia coli*.star-solid.", The Journal of Biological Chemistry, vol. 259, No. 4, Feb. 25, 1984, pp. 2149-2154.

Kozak, M., "The Scanning Model for Translation and Update," The Journal of Cell Biology 108:229-241 (Feb. 1989).

Krasnow et al., "Whole animal cell sorting of *Drosophilia* embryos," Science, 4:251(4989):81-85 (Jan. 1991) Abstract Only.

Kuo et al., "Iodometric Method for Detection of .beta.-Lactamase Activity in Yeast Cells Carrying Ampicillin Resistance Gene in Chimeric Plasmids", Analytical Bacteria, 177, pp. 165-167 (1989).

Lakowicz J.R., Principles of Fluorescence Spectroscopy, New York:Plenum Press (1983) Herman B., Resonnance energy transfer microscopy, in:Fluorescence Microscopy of Living Cells in Culture, Part B, Methods in Cell. Biology, vol. 30, ed.

Li et al., "RNA Polymerase II Initiation Factor Interactions and Transcription Start Site Selection," Science, vol. 263 (Feb. 1994).

Lin et al., "lacZ expression in germline transgenic zebrafish can be detected in living embryos," Dev. Biology 161(1):77-83 (Jan. 1994). Abstract Only.

Moore et al.. The development of beta lactamase as a highly versatile genetic reporter for eukaryotic cells. 1997. Analytical Biochemistry vol. 247, pp. 203-209.

Murphy B.P. et al., "N-(Phenylacetyl)glycl-D-aziridine-2-carboxylate, an Acyclic Amide Substrate of .beta.-Lactamases: Importance of the shape of the Substrate in .beta.-Lactamase Evolution", Biochemistry, 1991, 30, 3640-3649.

O'Callaghan. C.H. et al., "Effects of .beta.-Lactamase from Gram-negative Organisms on Cephalosporins and Penicillins", Antimicrobial Agents and Chemotherapy (1968), pp. 57-63.

O'Callaghan C.H. et al., "Novel Method for Detection of .beta.-Lactamases by Using a Chromogenic Cephalosporin Substrate", Antimicrob. Agents Chemother., 1:283-288 (1972).

Page M.I., "The Mechanisms of Reactions of .beta.-Lactam Antibiotics", Adv. Phys. Org. Chem. 23:165-270 (1987).

Parr et al., Antimicrobial Agents Chemother. 31:121-123, 1987.

Pratt R.F. et al., ".beta.-Lactamase-catalyzed hydrolysis of acyclic depsipeptides and acyl transfer to specific amino acid acceptors", Proc. Natl. Acad. Sci. USA vol. 81, pp. 1302-1306, Mar. 1984.

Przybycien et al. Secondary structure characterization of .beta.-lactamase inclusion bodies. Protein Engineering. 7(1): 131-136, Jan. 1994.

Richmond, M.H. et al., "The .beta.-Lactamases of Gram-Negative Bacteria Including Pseudomonads.star-solid.", Ann. N.Y. Acad. Sci., 182: 243-257 (1971).

Richmond M.H., "The .beta.-Lactamases of Gram-Negative Bacteria and their Possible Physiological Role", Adv. Microb. Physiol., 9:31-88 (1973).

Rodrigues, et al. "Development of a Humanized Disulfide-stabilized Anti-p185HER2Fv-.beta.-Lactamase Fusion Protein for Activation of a Cephalosporin Doxorubicin Prodrug", Cancer Res., 55:63-70 (1995).

Rosenthal, N., Identification of Regulatory Elements of Cloned Genes with Functional Assays, Methods Enzymol., 152:704-720 (1987).

Schilling et al., "Regulation of a fos-lacz Fusion Gene: A Paradigm for Quantitative Analysis of Stimulus Transcription Coupling," (Abstract) Proceedings of the National Academy of Sciences 88(1) (Jul. 1, 1991).

Sekkali et al., Mol. Marine Biol. Biotechnol. 3:30-34, 1994.

Shiau, A. et al., "Improved cat gene cassette for promoter analysis and genetic constructions", Gene 67 (1988) 295-299.

Simon, Kay et al., "Translocation of Globin Fusion Proteins across the Endoplasmic Reticulum Membrane in *Xenopus laevis* Oocytes", The Journal of Cell Biology, vol. 104, May 1987, pp. 1165-1172.

Simonen et al., "The Role of the Carrier Protein and Disulfide Formation in the Folding of .beta.-Lactamase Fusion Proteins in the Endoplasmic Reticulum of Yeast", Jrnl. Biol. Chem. 269:13887-13892, (1994).

Smith et al. Construction and use of signal sequence selection vectors in *Escherichia coli Bacillus subtilis*. J. Bacteriology 169 (7):3321-3328, Jul. 1987.

Stratton, C.W., "Activity of .beta.-Lactamases against .beta.-lactams", Journal of Antimicrobial Chemotherapy, (1988) 22, Supp. A 23-35.

Stryer, I., "Introduction to Enzymes" Biochemistry, 1981, pp. 103-134.

Sui-Lam Wong, "Development of an inducible and enhancible expression and secretion system in *Bacillus subtilis*", Gene, 83 (1989) pp. 215-223.

Sutcliffe J.G., "Nucleotide sequence of the ampicillin resistance gene of *Escherichia coli* plasmid pBR322", Proc. Natl. Acad. Sci., vol. 75, No. 8, pp. 3737-3741, Aug. 1978.

Taylor D.I. et al., San Diego: Academic Press (1989) pp. 219-243.

Tomilin et al., "Expression in Chinese hamster transformant TK+- cells of the bacterial gene for beta-lactamase", Tsitologia, 27(6):688-692 (Jun. 1985) Abstract Only.

Tsien R.Y., "New Tetracarboxylate Chelators for Fluorescence Measurement and Photochemical Manipulation of Cytosolic Free Calcium Concentrations", Optical Methods in Cell Physiology, ed de Weer, P. & Salzberg B., New York:Wiley, pp. 327-345.

Tsien R.Y. et al., "Practical design criteria for a dynamic ratio imaging system", Cell Calcium (1990) 11:93-109.

Tsien et al., "Fluorophores for Confocal Microscopy: Photophysics and Photochemistry", Handbook of Biological Confocal Microscopy. edited by James B. Pawley, Plenum Publishing Corp., 1990, pp. 169-178.

Turro N.J., "Modern Molecular Photochemistry", Menlo Part:Benjamin/Cummings Publishing Co., Inc., 1978, pp. 296-361.

Van Heyningen et al., "The Chemistry of Cephalosporins. IV. Acetoxyl Replacements with Xanthates and Dithiocarbamates", J. Med. Chem., 8:174-181 (1965).

Waley, S.G., ".beta.-Lactamases a major cause of antibiotic resistance", Sci. Prog. Oxf. (1988) 72, 579-597.

Waterham, Hans R. et al., "The Hansenula polymorpha PER1 Gene is Essential for Peroxisome Bioigenesis and Encodes a Peroxisomal Matrix Protein with Both Carboxy- and Amino-terminal Targeting Signals", The Journal of Cell Biology, vol. 127, No. 3, Nov. 1994, pp. 737-749.

Wiedmann, M. et al., "*Xenopus oocytes* can secrete bacterial .beta.-lactamase", Nature, vol. 309, Jun. 14, 1984, pp. 637-639.

Wong et al., Gene 10:87-94, 1980.

Yaron A. et al., Anal. Biochem., 95:228-235 (1979).

Zlokarnik at al., "Quantitation of Transcription and Clonal Selection of Single Living Cells with .beta.-Lactamase as Reporter", Science, vol. 279, Jan. 2, 1998.

| Seq ID | parent β-lactamase gene and reference | modification | mammalian expression vector | location of expression |
|---|---|---|---|---|
| #1 | Escherichia coli RTEM Kadonaga et al. | signal sequence replaced by: ATG TGA | pMAM-neo glucocorticoid inducible | cytoplasmic |
| #2 | Escherichia coli RTEM Kadonaga et al. | wild type secreted enzyme 2 changes in pre-sequence: ser 2 arg, ala 23 gly | pMAM-neo glucocorticoid inducible | secreted extracellularly |
| #3 | Escherichia coli RTEM | β-globin up stream leader: AAGCTTTTTGCAGAAGCTCA GAATAAACGCAACTTTCCG Kozak sequence: GGTACCACCATGG signal sequence replaced by: ATG GGG | pCDNA 3 CMV promotor and pZEO SV40 promotor | cytoplasmic |
| #4 | Escherichia coli RTEM | Kozak sequence: GGTACCACCATGG signal sequence replaced by: ATG GAC (GAC replaces CAT) | pMAM-neo glucocorticoid inducible | cytoplasmic |
| #5 | Bacillus licheniformis 749/C Neugebauer et al. | signal sequence removed, new N-terminal ATG | pCDNA 3 CMV promotor | cytoplasmic |

J. Kadonaga et al., J. Biol. Chem., 259: 2149 (1984)
K. Neugebauer et al., Nucleic Acid Res., 9: 2577 (1981)

FIG. 7A

Sequence no. 1: range 1 to 795
E. coli RTEM as modified by Kadonaga at al (1984)

```
            10          20          30          40          50
         *           *           *           *           *
ATG AGT CAC CCA GAA ACG CTG GTG AAA GTA AAA GAT GCT GAA GAT CAG TTG
Met Ser His Pro Glu Thr Leu Val Lys Val Lys Asp Ala Glu Asp Gln Leu
         60          70          80          90          100
         *           *     *     *           *           *     *
GGT GCA CGA GTG GGT TAC ATC GAA CTG GAT CTC AAC AGC GGT AAG ATC CTT
Gly Ala Arg Val Gly Tyr Ile Glu Leu Asp Leu Asn Ser Gly Lys Ile Leu
         110         120         130         140         150
    *     *     *     *     *     *     *     *     *     *
GAG AGT TTT CGC CCC GAA GAA CGT TTT CCA ATG ATG AGC ACT TTT AAA GTT
Glu Ser Phe Arg Pro Glu Glu Arg Phe Pro Met Met Ser Thr Phe Lys Val
         160         170         180         190         200
    *     *     *     *     *     *     *     *     *     *
CTG CTA TGT GGC GCG GTA TTA TCC CGT GTT GAC GCC GGG CAA GAG CAA CTC
Leu Leu Cys Gly Ala Val Leu Ser Arg Val Asp Ala Gly Gln Glu Gln Leu
         210         220         230         240         250
    *     *     *     *     *     *     *     *     *     *     *
GGT CGC CGC ATA CAC TAT TCT CAG AAT GAC TTG GTT GAG TAC TCA CCA GTC
Gly Arg Arg Ile His Tyr Ser Gln Asn Asp Leu Val Glu Tyr Ser Pro Val
         260         270         280         290         300
    *     *     *     *     *     *     *     *     *     *
ACA GAA AAG CAT CTT ACG GAT GGC ATG ACA GTA AGA GAA TTA TGC AGT GCT
Thr Glu Lys His Leu Thr Asp Gly Met Thr Val Arg Glu Leu Cys Ser Ala
         310         320         330         340         350
    *     *     *     *     *     *     *     *     *     *
GCC ATA ACC ATG AGT GAT AAC ACT GCG GCC AAC TTA CTT CTG ACA ACG ATC
Ala Ile Thr Met Ser Asp Asn Thr Ala Ala Asn Leu Leu Leu Thr Thr Ile
         360         370         380         390         400
    *     *     *     *     *     *     *     *     *     *
GGA GGA CCG AAG GAG CTA ACC GCT TTT TTG CAC AAC ATG GGG GAT CAT GTA
Gly Gly Pro Lys Glu Leu Thr Ala Phe Leu His Asn Met Gly Asp His Val
         410         420         430         440         450
    *     *     *     *     *     *     *     *     *     *
ACT CGC CTT GAT CGT TGG GAA CCG GAG CTG AAT GAA GCC ATA CCA AAC GAC
Thr Arg Leu Asp Arg Trp Glu Pro Glu Leu Asn Glu Ala Ile Pro Asn Asp
         460         470         480         490         500         510
    *     *     *     *     *     *     *     *     *     *     *
GAG CGT GAC ACC ACG ATG CCT GCA GCA ATG GCA ACA ACG TTG CGC AAA CTA
Glu Arg Asp Thr Thr Met Pro Ala Ala Met Ala Thr Thr Leu Arg Lys Leu
```

FIG. 7B

```
        520           530           540           550           560
         *        *    *        *    *        *    *        *    *        *
TTA ACT GGC GAA CTA CTT ACT CTA GCT TCC CGG CAA CAA TTA ATA GAC TGG
Leu Thr Gly Glu Leu Leu Thr Leu Ala Ser Arg Gln Gln Leu Ile Asp Trp
        570           580           590           600           610
         *        *    *        *    *        *    *        *    *        *
ATG GAG GCG GAT AAA GTT GCA GGA CCA CTT CTG CGC TCG GCC CTT CCG GCT
Met Glu Ala Asp Lys Val Ala Gly Pro Leu Leu Arg Ser Ala Leu Pro Ala
        620           630           640           650           660
         *        *    *        *    *        *    *        *    *        *
GGC TGG TTT ATT GCT GAT AAA TCT GGA GCC GGT GAG CGT GGG TCT CGC GGT
Gly Trp Phe Ile Ala Asp Lys Ser Gly Ala Gly Glu Arg Gly Ser Arg Gly
        670           680           690           700           710
         *        *    *        *    *        *    *        *    *        *
ATC ATT GCA GCA CTG GGG CCA GAT GGT AAG CCC TCC CGT ATC GTA GTT ATC
Ile Ile Ala Ala Leu Gly Pro Asp Gly Lys Pro Ser Arg Ile Val Val Ile
        720           730           740           750           760
         *        *    *        *    *        *    *        *    *        *
TAC ACG ACG GGG AGT CAG GCA ACT ATG GAT GAA CGA AAT AGA CAG ATC GCT
Tyr Thr Thr Gly Ser Gln Ala Thr Met Asp Glu Arg Asn Arg Gln Ile Ala
        770           780           790
         *        *    *        *    *        *
GAG ATA GGT GCC TCA CTG ATT AAG CAT TGG
Glu Ile Gly Ala Ser Leu Ile Lys His Trp
```

FIG. 7C

Sequence no. 2: range 1 to 858
Wild-type secreted RTEM enzyme with Ser2→Arg, Ala23→Gly

```
         10              20              30              40              50
    *    *     *    *    *    *    *    *    *    *    *    *    *    *    *    *    *
ATG AGA ATT CAA CAT TTC CGT GTC GCC CTT ATT CCC TTT TTT GCG GCA TTT
Met Arg Ile Gln His Phe Arg Val Ala Leu Ile Pro Phe Phe Ala Ala Phe
         60              70              80              90             100
    *    *    *    *    *    *    *    *    *    *    *    *    *    *    *    *
TGC CTT CCT GTT TTT GGT CAC CCA GAA ACG CTG GTG AAA GTA AAA GAT GCT
Cys Leu Pro Val Phe Gly His Pro Glu Thr Leu Val Lys Val Lys Asp Ala
        110             120             130             140             150
    *    *    *    *    *    *    *    *    *    *    *    *    *    *    *    *
GAA GAT CAG TTG GGT GCA CGA GTG GGT TAC ATC GAA CTG GAT CTC AAC AGC
Glu Asp Gln Leu Gly Ala Arg Val Gly Tyr Ile Glu Leu Asp Leu Asn Ser
        160             170             180             190             200
    *    *    *    *    *    *    *    *    *    *    *    *    *    *    *    *
GGT AAG ATC CTT GAG AGT TTT CGC CCC GAA GAA CGT TTT CCA ATG ATG AGC
Gly Lys Ile Leu Glu Ser Phe Arg Pro Glu Glu Arg Phe Pro Met Met Ser
        210             220             230             240             250
    *    *    *    *    *    *    *    *    *    *    *    *    *    *    *    *
ACT TTT AAA GTT CTG CTA TGT GGC GCG GTA TTA TCC CGT GTT GAC GCC GGG
Thr Phe Lys Val Leu Leu Cys Gly Ala Val Leu Ser Arg Val Asp Ala Gly
        260             270             280             290             300
    *    *    *    *    *    *    *    *    *    *    *    *    *    *    *    *
CAA GAG CAA CTC GGT CGC CGC ATA CAC TAT TCT CAG AAT GAC TTG GTT GAG
Gln Glu Gln Leu Gly Arg Arg Ile His Tyr Ser Gln Asn Asp Leu Val Glu
        310             320             330             340             350
    *    *    *    *    *    *    *    *    *    *    *    *    *    *    *    *
TAC TCA CCA GTC ACA GAA AAG CAT CTT ACG GAT GGC ATG ACA GTA AGA GAA
Tyr Ser Pro Val Thr Glu Lys His Leu Thr Asp Gly Met Thr Val Arg Glu
        360             370             380             390             400
    *    *    *    *    *    *    *    *    *    *    *    *    *    *    *    *
TTA TGC AGT GCT GCC ATA ACC ATG AGT GAT AAC ACT GCG GCC AAC TTA CTT
Leu Cys Ser Ala Ala Ile Thr Met Ser Asp Asn Thr Ala Ala Asn Leu Leu
        410             420             430             440             450
    *    *    *    *    *    *    *    *    *    *    *    *    *    *    *    *
CTG ACA ACG ATC GGA GGA CCG AAG GAG CTA ACC GCT TTT TTG CAC AAC ATG
Leu Thr Thr Ile Gly Gly Pro Lys Glu Leu Thr Ala Phe Leu His Asn Met
460             470             480             490             500             510
    *    *    *    *    *    *    *    *    *    *    *    *    *    *    *    *    *
GGG GAT CAT GTA ACT CGC CTT GAT CGT TGG GAA CCG GAG CTG AAT GAA GCC
Gly Asp His Val Thr Arg Leu Asp Arg Trp Glu Pro Glu Leu Asn Glu Ala
```

FIG. 7D

```
          520           530           540           550           560
    *      *     *      *     *      *     *      *     *      *
ATA CCA AAC GAC GAG CGT GAC ACC ACG ATG CCT GCA GCA ATG GCA ACA ACG
Ile Pro Asn Asp Glu Arg Asp Thr Thr Met Pro Ala Ala Met Ala Thr Thr
          570           580           590           600           610
    *      *     *      *     *      *     *      *     *      *
TTG CGC AAA CTA TTA ACT GGC GAA CTA CTT ACT CTA GCT TCC CGG CAA CAA
Leu Arg Lys Leu Leu Thr Gly Glu Leu Leu Thr Leu Ala Ser Arg Gln Gln
          620           630           640           650           660
    *      *     *      *     *      *     *      *     *      *
TTA ATA GAC TGG ATG GAG GCG GAT AAA GTT GCA GGA CCA CTT CTG CGC TCG
Leu Ile Asp Trp Met Glu Ala Asp Lys Val Ala Gly Pro Leu Leu Arg Ser
          670           680           690           700           710
    *      *     *      *     *      *     *      *     *      *
GCC CTT CCG GCT GGC TGG TTT ATT GCT GAT AAA TCT GGA GCC GGT GAG CGT
Ala Leu Pro Ala Gly Trp Phe Ile Ala Asp Lys Ser Gly Ala Gly Glu Arg
          720           730           740           750           760
    *      *     *      *     *      *     *      *     *      *
GGG TCT CGC GGT ATC ATT GCA GCA CTG GGG CCA GAT GGT AAG CCC TCC CGT
Gly Ser Arg Gly Ile Ile Ala Ala Leu Gly Pro Asp Gly Lys Pro Ser Arg
          770           780           790           800           810
    *      *     *      *     *      *     *      *     *      *
ATC GTA GTT ATC TAC ACG ACG GGG AGT CAG GCA ACT ATG GAT GAA CGA AAT
Ile Val Val Ile Tyr Thr Thr Gly Ser Gln Ala Thr Met Asp Glu Arg Asn
          820           830           840           850
    *      *     *      *     *      *     *      *
AGA CAG ATC GCT GAG ATA GGT GCC TCA CTG ATT AAG CAT TGG
Arg Gln Ile Ala Glu Ile Gly Ala Ser Leu Ile Lys His Trp
```

FIG. 7E

Sequence no. 3: range 1 to 795
RTEM enzyme with β-globin upstream leader, mammalian Kozak sequence, replacement of signal sequence by Met Gly

```
AAGCTTTTTGCAGAAGCTCAGAATAAACGCAACTTTCCGGGTACCACC
         10        20        30        40        50
          *    *    *    *    *    *    *    *    *    *    *
ATG GGG CAC CCA GAA ACG CTG GTG AAA GTA AAA GAT GCT GAA GAT CAG TTG GGT GCA
Met Gly His Pro Glu Thr Leu Val Lys Val Lys Asp Ala Glu Asp Gln Leu Gly Ala
     60             70             80             90            100
      *    *    *    *    *    *    *    *    *    *
CGA GTG GGT TAC ATC GAA CTG GAT CTC AAC AGC GGT AAG ATC CTT GAG AGT
Arg Val Gly Tyr Ile Glu Leu Asp Leu Asn Ser Gly Lys Ile Leu Glu Ser
 110           120           130           140           150
  *    *    *    *    *    *    *    *    *    *
TTT CGC CCC GAA GAA CGT TTT CCA ATG ATG AGC ACT TTT AAA GTT CTG CTA
Phe Arg Pro Glu Glu Arg Phe Pro Met Met Ser Thr Phe Lys Val Leu Leu
160'          170           180           190           200           210
  *    *    *    *    *    *    *    *    *    *    *
TGT GGC GCG GTA TTA TCC CGT GAT GAC GCC GGG CAA GAG CAA CTC GGT CGC
Cys Gly Ala Val Leu Ser Arg Ile Asp Ala Gly Gln Glu Gln Leu Gly Arg
         220           230           240           250           260
      *    *    *    *    *    *    *    *    *    *
CGC ATA CAC TAT TCT CAG AAT GAC TTG GTT GAG TAC TCA CCA GTC ACA GAA
Arg Ile His Tyr Ser Gln Asn Asp Leu Val Glu Tyr Ser Pro Val Thr Glu
         270           280           290           300           310
      *    *    *    *    *    *    *    *    *    *
AAG CAT CTT ACG GAT GGC ATG ACA GTA AGA GAA TTA TGC AGT GCT GCC ATA
Lys His Leu Thr Asp Gly Met Thr Val Arg Glu Leu Cys Ser Ala Ala Ile
         320           330           340           350           360
      *    *    *    *    *    *    *    *    *    *
ACC ATG AGT GAT AAC ACT GCG GCC AAC TTA CTT CTG ACA ACG ATC GGA GGA
Thr Met Ser Asp Asn Thr Ala Ala Asn Leu Leu Leu Thr Thr Ile Gly Gly
         370           380           390           400           410
      *    *    *    *    *    *    *    *    *    *
CCG AAG GAG CTA ACC GCT TTT TTG CAC AAC ATG GGG GAT CAT GTA ACT CGC
Pro Lys Glu Leu Thr Ala Phe Leu His Asn Met Gly Asp His Val Thr Arg
         420           430           440           450           460
  *    *    *    *    *    *    *    '*    *    *    *
CTT GAT CAT TGG GAA CCG GAG CTG AAT GAA GCC ATA CCA AAC GAC GAG CGT
Leu Asp His Trp Glu Pro Glu Leu Asn Glu Ala Ile Pro Asn Asp Glu Arg
```

FIG. 7F

```
        470          480          490          500          510
         *    *       *    *       *    *       *    *       *    *
GAC ACC ACG ATG CCT GTA GCA ATG GCA ACA ACG TTG CGC AAA CTA TTA ACT
Asp Thr Thr Met Pro Val Ala Met Ala Thr Thr Leu Arg Lys Leu Leu Thr
   520          530          540          550          560
    *    *       *    *       *    *       *    *       *    *
GGC GAA CTA CTT ACT CTA GCT TCC CGG CAA CAA TTA ATA GAC TGG ATG GAG
Gly Glu Leu Leu Thr Leu Ala Ser Arg Gln Gln Leu Ile Asp Trp Met Glu
 570          580          590          600          610
  *    *       *    *       *    *       *    *       *    *
GCG GAT AAA GTT GCA GGA CCA CTT CTG CGC TCG GCC CTT CCG GCT GGC TGG
Ala Asp Lys Val Ala Gly Pro Leu Leu Arg Ser Ala Leu Pro Ala Gly Trp
620          630          640          650          660
  *    *       *    *       *    *       *    *       *    *
TTT ATT GCT GAT AAA TCT GGA GCC GGT GAG CGT GGG TCT CGC GGT ATC ATT
Phe Ile Ala Asp Lys Ser Gly Ala Gly Glu Arg Gly Ser Arg Gly Ile Ile
670          680          690          700          710          720
  *    *       *    *       *    *       *    *       *    *    *
GCA GCA CTG GGG CCA GAT GGT AAG CCC TCC CGT ATC GTA GTT ATC TAC ACG
Ala Ala Leu Gly Pro Asp Gly Lys Pro Ser Arg Ile Val Val Ile Tyr Thr
            730          740          750          760          770
    *    *       *    *       *    *       *    *       *    *    *
ACG GGG AGT CAG GCA ACT ATG GAT GAA CGA AAT AGA CAG ATC GCT GAG ATA
Thr Gly Ser Gln Ala Thr Met Asp Glu Arg Asn Arg Gln Ile Ala Glu Ile
            780          790
    *    *       *    *    *
GGT GCC TCA CTG ATT AAG CAT TGG
Gly Ala Ser Leu Ile Lys His Trp
```

FIG. 7G

Sequence no. 4: range 1 to 792
RTEM β-lactamase with mammalian Kozak sequence and replacement of signal sequence by Met Asp

```
             10            20            30            40            50
       *      *      *      *      *      *      *      *      *      *
ATG GAC CCA GAA ACG CTG GTG AAA GTA AAA GAT GCT GAA GAT CAG TTG GGT
Met Asp Pro Glu Thr Leu Val Lys Val Lys Asp Ala Glu Asp Gln Leu Gly
             60            70            80            90           100
       *      *      *      *      *      *      *      *      *      *
GCA CGA GTG GGT TAC ATC GAA CTG GAT CTC AAC AGC GGT AAG ATC CTT GAG
Ala Arg Val Gly Tyr Ile Glu Leu Asp Leu Asn Ser Gly Lys Ile Leu Glu
            110           120           130           140           150
       *      *      *      *      *      *      *      *      *      *
AGT TTT CGC CCC GAA GAA CGT TTT CCA ATG ATG AGC ACT TTT AAA GTT CTG
Ser Phe Arg Pro Glu Glu Arg Phe Pro Met Met Ser Thr Phe Lys Val Leu
            160           170           180           190           200
       *      *      *      *      *      *      *      *      *      *
CTA TGT GGC GCG GTA TTA TCC CGT ATT GAC GCC GGG CAA GAG CAA CTC GGT
Leu Cys Gly Ala Val Leu Ser Arg Ile Asp Ala Gly Gln Glu Gln Leu Gly
            210           220           230           240           250
       *      *      *      *      *      *      *      *      *      *
CGC CGC ATA CAC TAT TCT CAG AAT GAC TTG GTT GAG TAC TCA CCA GTC ACA
Arg Arg Ile His Tyr Ser Gln Asn Asp Leu Val Glu Tyr Ser Pro Val Thr
            260           270           280           290           300
       *      *      *      *      *      *      *      *      *      *
GAA AAG CAT CTT ACG GAT GGC ATG ACA GTA AGA GAA TTA TGC AGT GCT GCC
Glu Lys His Leu Thr Asp Gly Met Thr Val Arg Glu Leu Cys Ser Ala Ala
            310           320           330           340           350
       *      *      *      *      *      *      *      *      *      *
ATA ACC ATG AGT GAT AAC ACT GCG GCC AAC TTA CTT CTG ACA ACG ATC GGA
Ile Thr Met Ser Asp Asn Thr Ala Ala Asn Leu Leu Leu Thr Thr Ile Gly
            360           370           380           390           400
       *      *      *      *      *      *      *      *      *      *
GGA CCG AAG GAG CTA ACC GCT TTT TTG CAC AAC ATG GGG GAT CAT GTA ACT
Gly Pro Lys Glu Leu Thr Ala Phe Leu His Asn Met Gly Asp His Val Thr
            410           420           430           440           450
       *      *      *      *      *      *      *      *      *      *
CGC CTT GAT CAT TGG GAA CCG GAG CTG AAT GAA GCC ATA CCA AAC GAC GAG
Arg Leu Asp His Trp Glu Pro Glu Leu Asn Glu Ala Ile Pro Asn Asp Glu
            460           470           480           490           500           510
       *      *      *      *      *      *      *      *      *      *      *
CGT GAC ACC ACG ATG CCT GTA GCA ATG GCA ACA ACG TTG CGC AAA CTA TTA
Arg Asp Thr Thr Met Pro Val Ala Met Ala Thr Thr Leu Arg Lys Leu Leu
```

FIG. 7H

```
              520         530         540         550         560
               *           *           *           *           *
ACT GGC GAA CTA CTT ACT CTA GCT TCC CGG CAA CAA TTA ATA GAC TGG ATG
Thr Gly Glu Leu Leu Thr Leu Ala Ser Arg Gln Gln Leu Ile Asp Trp Met
          570         580         590         600         610
           *           *           *           *           *
GAG GCG GAT AAA GTT GCA GGA CCA CTT CTG CGC TCG GCC CTT CCG GCT GGC
Glu Ala Asp Lys Val Ala Gly Pro Leu Leu Arg Ser Ala Leu Pro Ala Gly
      620         630         640         650         660
       *           *           *           *           *
TGG TTT ATT GCT GAT AAA TCT GGA GCC GGT GAG CGT GGG TCT CGC GGT ATC
Trp Phe Ile Ala Asp Lys Ser Gly Ala Gly Glu Arg Gly Ser Arg Gly Ile
          670         680         690         700         710
           *           *           *           *           *
ATT GCA GCA CTG GGG CCA GAT GGT AAG CCC TCC CGT ATC GTA GTT ATC TAC
Ile Ala Ala Leu Gly Pro Asp Gly Lys Pro Ser Arg Ile Val Val Ile Tyr
      720         730         740         750         760
       *           *           *           *           *
ACG ACG GGG AGT CAG GCA ACT ATG GAT GAA CGA AAT AGA CAG ATC GCT GAG
Thr Thr Gly Ser Gln Ala Thr Met Asp Glu Arg Asn Arg Gln Ile Ala Glu
          770         780         790
           *           *           *
ATA GGT GCC TCA CTG ATT AAG CAT TGG
Ile Gly Ala Ser Leu Ile Lys His Trp
```

FIG. 7I

Sequence no. 5: range 1 to 786
Bacillus licheniformis β-lactamase with
signal sequence replaced

```
              10               20               30               40               50
        *        *        *        *        *        *        *        *        *        *
ATG  AAA  GAT  GAT  TTT  GCA  AAA  CTT  GAG  GAA  CAA  TTT  GAT  GCA  AAA  CTC  GGG
Met  Lys  Asp  Asp  Phe  Ala  Lys  Leu  Glu  Glu  Gln  Phe  Asp  Ala  Lys  Leu  Gly
         60               70               80               90              100
        *        *        *        *        *        *        *        *        *        *
ATC  TTT  GCA  TTG  GAT  ACA  GGT  ACA  AAC  CGG  ACG  GTA  GCG  TAT  CGG  CCG  GAT
Ile  Phe  Ala  Leu  Asp  Thr  Gly  Thr  Asn  Arg  Thr  Val  Ala  Tyr  Arg  Pro  Asp
              110              120              130              140              150
        *        *        *        *        *        *        *        *        *        *
GAG  CGT  TTT  GCT  TTT  GCT  TCG  ACG  ATT  AAG  GCT  TTA  ACT  GTA  GGC  GTG  CTT
Glu  Arg  Phe  Ala  Phe  Ala  Ser  Thr  Ile  Lys  Ala  Leu  Thr  Val  Gly  Val  Leu
         160              170              180              190              200
        *        *        *        *        *        *        *        *        *        *
TTG  CAA  CAG  AAA  TCA  ATA  GAA  GAT  CTG  AAC  CAG  AGA  ATA  ACA  TAT  ACA  CGT
Leu  Gln  Gln  Lys  Ser  Ile  Glu  Asp  Leu  Asn  Gln  Arg  Ile  Thr  Tyr  Thr  Arg
         210              220              230              240              250
        *        *        *        *        *        *        *        *        *        *
GAT  GAT  CTT  GTA  AAC  TAC  AAC  CCG  ATT  ACG  GAA  AAG  CAC  GTT  GAT  ACG  GGA
Asp  Asp  Leu  Val  Asn  Tyr  Asn  Pro  Ile  Thr  Glu  Lys  His  Val  Asp  Thr  Gly
         260              270              280              290              300
        *        *        *        *        *        *        *        *        *        *
ATG  ACG  CTC  AAA  GAG  CTT  GCG  GAT  GCT  TCG  CTT  CGA  TAT  AGT  GAC  AAT  GCG
Met  Thr  Leu  Lys  Glu  Leu  Ala  Asp  Ala  Ser  Leu  Arg  Tyr  Ser  Asp  Asn  Ala
         310              320              330              340              350
        *        *        *        *        *        *        *        *        *        *
GCA  CAG  AAT  CTC  ATT  CTT  AAA  CAA  ATT  GGC  GGA  CCT  GAA  AGT  TTG  AAA  AAG
Ala  Gln  Asn  Leu  Ile  Leu  Lys  Gln  Ile  Gly  Gly  Pro  Glu  Ser  Leu  Lys  Lys
         360              370              380              390              400
        *        *        *        *        *        *        *        *        *        *
GAA  CTG  AGG  AAG  ATT  GGT  GAT  GAG  GTT  ACA  AAT  CCC  GAA  CGA  TTC  GAA  CCA
Glu  Leu  Arg  Lys  Ile  Gly  Asp  Glu  Val  Thr  Asn  Pro  Glu  Arg  Phe  Glu  Pro
410              420              430              440              450
        *        *        *        *        *        *        *        *        *        *
GAG  TTA  AAT  GAA  GTG  AAT  CCG  GGT  GAA  ACT  CAG  GAT  ACC  AGT  ACA  GCA  AGA
Glu  Leu  Asn  Glu  Val  Asn  Pro  Gly  Glu  Thr  Gln  Asp  Thr  Ser  Thr  Ala  Arg
         460              470              480              490              500              510
        *        *        *        *        *        *        *        *        *        *
GCA  CTT  GTC  ACA  AGC  CTT  CGA  GCC  TTT  GCT  CTT  GAA  GAT  AAA  CTT  CCA  AGT
Ala  Leu  Val  Thr  Ser  Leu  Arg  Ala  Phe  Ala  Leu  Glu  Asp  Lys  Leu  Pro  Ser
```

FIG. 7J

```
              520            530           540           550           560
       *    *    *      *    *    *    *    *    *    *    *
GAA AAA CGC GAG CTT TTA ATC GAT TGG ATG AAA CGA AAT ACC ACT GGA GAC
Glu Lys Arg Glu Leu Leu Ile Asp Trp Met Lys Arg Asn Thr Thr Gly Asp
              570            580           590           600           610
       *    *    *      *    *    *    *    *    *    *    *
GCC TTA ATC CGT GCC GGA GCG GCA TCA TAT GGA ACC CGG AAT GAC ATT GCC
Ala Leu Ile Arg Ala Gly Val Pro Asp Gly Trp Glu Val Ala Asp Lys Thr
              620            630           640           650           660
       *    *    *      *    *    *    *    *    *    *    *
ATC ATT TGG CCG CCA AAA GGA GAT CCT GTC GGT GTG CCG GAC GGT TGG GAA
Gly Ala Ala Ser Tyr Lys Gly Asp Pro Val Gly Thr Arg Asn Asp Ile Ala
              670            680           690           700           710
       *    *    *      *    *    *    *    *    *    *    *
GTG GCT GAT AAA ACT GTT CTT GCA GTA TTA TCC AGC AGG GAT AAA AAG GAC
Ile Ile Trp Pro Pro Val Leu Ala Val Leu Ser Ser Arg Asp Lys Lys Asp
              720            730           740           750           760
       *    *    *      *    *    *    *    *    *    *    *
GCC AAG TAT GAT GAT AAA CTT ATT GCA GAG GCA ACA AAG GTG GTA ATG AAA
Ala Lys Tyr Asp Asp Lys Leu Ile Ala Glu Ala Thr Lys Val Val Met Lys
              770            780
       *    *    *      *
GCC TTA AAC ATG AAC GGC AAA
Ala Leu Asn Met A9((
```

FIG. 7K

SUBSTRATES FOR BETA-LACTAMASE AND USES THEREOF

BACKGROUND OF THE INVENTION

This application is a continuation application of U.S. application Ser. No. 10/280,482, filed Oct. 24, 2002, now U.S. Pat. No. 7,157,575, which is a continuation application of U.S. application Ser. No. 09/481,756, filed Jan. 11, 2000, now U.S. Pat. No. 6,472,205, which is a continuation application of U.S. application Ser. No. 08/727,616, filed Oct. 15, 1996, now U.S. Pat. No. 6,291,162, which is a continuation application of PCT/US96/04059, filed Mar. 20, 1996, which is a continuation-in-part of U.S. application Ser. No. 08/407,544, filed Mar. 20, 1995, now U.S. Pat. No. 5,741,657.

STATEMENT REGARDING FEDERALLY SPONSORED RESEARCH OR DEVELOPMENT

This invention was made with government support under Grant No. NS27177 awarded by the National Institutes of Health. The government has certain rights in the invention.

The present invention relates generally to the fields of chemistry and biology. More particularly, the present invention relates to compositions and methods for use in measuring gene expression.

A reporter gene assay measures the activity of a gene's promoter. It takes advantage of molecular biology techniques, which allow one to put heterologous genes under the control of any promoter and introduce the construct into the genome of a mammalian cell [Gorman, C. M. et al., *Mol. Cell Biol.* 2: 1044-1051 (1982); Alam, J. and Cook, J. L., *Anal-.Biochem.* 188: 245-254, (1990)]. Activation of the promoter induces the reporter gene as well as or instead of the endogenous gene. By design the reporter gene codes for a protein that can easily be detected and measured. Commonly it is an enzyme that converts a commercially available substrate into a product. This conversion is conveniently followed by either chromatography or direct optical measurement and allows for the quantification of the amount of enzyme produced.

Reporter genes are commercially available on a variety of plasmids for the study of gene regulation in a large variety of organisms [Alam and Cook, supra]. Promoters of interest can be inserted into multiple cloning sites provided for this purpose in front of the reporter gene on the plasmid [Rosenthal, N., *Methods Enzymol.* 152: 704-720 (1987); Shiau, A. and Smith, J. M., *Gene* 67: 295-299 (1988)]. Standard techniques are used to introduce these genes into a cell type or whole organism [e.g., as described in Sambrook, J., Fritsch, E. F. and Maniatis, T. Expression of cloned genes in cultured mammalian cells. In: *Molecular Cloning*, edited by Nolan, C. New York: Cold Spring Harbor Laboratory Press, 1989]. Resistance markers provided on the plasmid can then be used to select for successfully transfected cells.

Ease of use and the large signal amplification make this technique increasingly popular in the study of gene regulation. Every step in the cascade DNA --> RNA --> Enzyme --> Product --> Signal amplifies the next one in the sequence. The further down in the cascade one measures, the more signal one obtains.

In an ideal reporter gene assay, the reporter gene under the control of the promoter of interest is transfected into cells, either transiently or stably. Receptor activation leads to a change in enzyme levels via transcriptional and translational events. The amount of enzyme present can be measured via its enzymatic action on a substrate. The substrate is a small uncharged molecule that, when added to the extracellular solution, can penetrate the plasma membrane to encounter the enzyme. A charged molecule can also be employed, but the charges need to be masked by groups that will be cleaved by endogenous cellular enzymes (e.g., esters cleaved by cytoplasmic esterases).

For a variety of reasons, the use of substrates which exhibit changes in their fluorescence spectra upon interaction with an enzyme are particularly desirable. In some assays, the fluorogenic substrate is converted to a fluorescent product. Alternatively, the fluorescent substrate changes fluorescence properties upon conversion at the reporter enzyme. The product should be very fluorescent to obtain maximal signal, and very polar, to stay trapped inside the cell.

To achieve the highest possible sensitivity in a reporter assay one has to maximize the amount of signal generated by a single reporter enzyme. An optimal enzyme will convert $10^5$ substrate molecules per second under saturating conditions [Stryer, L. Introduction to enzymes. In: *Biochemistry*, New York: W. H. Freeman and company, 1981, pp. 103-134]. β-Lactamases will cleave about $10^3$ molecules of their favorite substrates per second [Chang, Y. H. et al., *Proc.Natl.Acad.Sci.USA* 87: 2823-2827 (1990)]. Using a fluorogenic substrate one can obtain up to $10^6$ photons per fluorescent product produced, depending on the type of dye used, when exciting with light of the appropriate wavelength. The signal terminates with the bleaching of the fluorophore [Tsien, R. Y. and Waggoner, A. S. Fluorophores for confocal microscopy: Photophysics and photochemistry. In: *Handbook of Biological Confocal Microscopy*, edited by Pawley, J. B. Plenum Publishing Corporation, 1990, pp. 169-178]. These numbers illustrate the theoretical magnitude of signal obtainable in this type of measurement. In practice a minute fraction of the photons generated will be detected, but this holds true for fluorescence, bioluminescence or chemiluminescence. A good fluorogenic substrate for a reporter enzyme has to have a high turnover at the enzyme in addition to good optical properties such as high extinction and high fluorescence quantum yield.

SUMMARY OF THE INVENTION

It is an object of the present invention to provide β-lactamase substrate compounds. It is a further object of the invention to provide membrane-permeant compounds. The membrane-permeant compounds may be transformed into substantially membrane-impermeant compounds.

Another object of the invention is to provide β-lactamase reporter genes. A further object of the present invention is to create cells containing the β-lactamase reporter genes functionally linked to a promotor such that when the promotor is turned on, the reporter gene will be expressed. Expression of the β-lactamase is measured with the β-lactamase substrates which emit light after hydrolysis by the β-lactamase.

A further object of the invention is to use the β-lactamase reporter genes in cells and the β-lactamase substrate compounds of the present invention to screen for biochemical activity.

In accordance with the present invention, fluorogenic substrates are provided of the general formula I

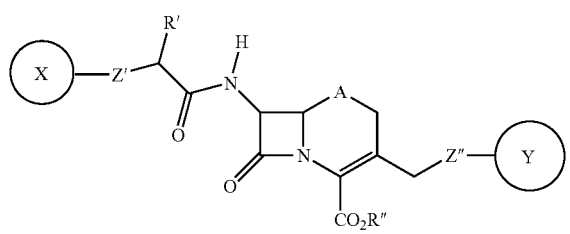

wherein:
one of X and Y is a fluorescent donor moiety or a membrane-permeant derivative thereof, and the other is a quencher moiety, an acceptor fluorophore moiety or a membrane-permeant derivative thereof;

R' is selected from the group consisting of H, lower alkyl, $(CH_2)_nOH$, $(CH_2)_nCOOR''$, and =NOJ, in which n is 0 or an integer from 1 to 5 and J is H, Me, $CH_2COOH$, $CHMeCOOH$, and $CMe_2COOH$;

R'' is selected from the group consisting of H, physiologically acceptable metal and ammonium cations, $-CHR^2OCO(CH_2)_nCH_3$, $-CHR^2OCOC(CH_3)_3$, acylthiomethyl, acyloxy-alpha-benzyl, delta-butyrolactonyl, methoxycarbonyloxymethyl, phenyl, methylsulphinylmethyl, betamorpholinoethyl, dialkylaminoethyl, dialkylaminocarbonyloxymethyl, in which $R^2$ is selected from the group consisting of H and lower alkyl;

A is selected from the group consisting of S, O, SO, $SO_2$ and $CH_2$;

Z' is a linker for X; and

Z'' is a linker for Y.

In another aspect, this invention provides methods for determining whether a sample contains β-lactamase activity. The methods involve contacting the sample with a compound substrate of the invention, which exhibits fluorescence resonance energy transfer when the compound is excited; exciting the compound; and determining the degree of fluorescence resonance energy transfer in the sample. A degree of fluorescence resonance energy transfer that is lower than an expected amount indicates the presence of β-lactamase activity. One embodiment of this method is for determining the amount of an enzyme in a sample. According to this method, determining the degree of fluorescence resonance energy transfer in the sample comprises determining the degree at a first and second time after contacting the sample with the substrate, and determining the difference in the degree of fluorescence resonance energy transfer. The difference in the degree of fluorescence resonance energy transfer reflects the amount of enzyme in the sample.

In another aspect, this invention provides recombinant nucleic acid molecule comprising expression control sequences adapted for function in a vertebrate cell and operably linked to a nucleotide sequence coding for the expression of a β-lactamase. It also provides recombinant nucleic acid molecules comprising expression control sequences adapted for function in a eukaryotic cell and operably linked to a nucleotide sequence coding for the expression of a cytosolic β-lactamase. In certain embodiments, the invention is directed to mammalian host cells transfected with these recombinant nucleic acid molecules.

In another aspect, this invention provides methods for determining the amount of β-lactamase activity in a cell. The methods involve providing a host cell transfected with a recombinant nucleic acid molecule comprising expression control sequences operatively linked to nucleic acid sequences coding for the expression of a β-lactamase; contacting a sample comprising the cell or an extract of the cell with a substrate for β-lactamase; and determining the amount of substrate cleaved, whereby the amount of substrate cleaved is related to the amount of β-lactamase activity.

In another aspect, this invention provides methods for monitoring the expression of a gene operably linked to a set of expression control sequences. The methods involve providing a host cell transfected with a recombinant nucleic acid molecule comprising expression control sequences operatively linked to nucleic acid sequences coding for the expression of a β-lactamase, except if the eukaryote is a fungus, wherein the β-lactamase is a cytosolic β-lactamase; contacting a sample comprising the cell or an extract of the cell or conditioned medium with a substrate for β-lactamase; and determining the amount of substrate cleaved. The amount of substrate cleaved is related to the amount of β-lactamase activity.

In another aspect, this invention provides methods for determining whether a test compound alters the expression of a gene operably linked to a set of expression control sequences. The methods involve providing a cell transfected with a recombinant nucleic acid construct comprising the expression control sequences operably linked to nucleic acid sequences coding for the expression of a β-lactamase except if the eukaryote is a fungus, wherein the β-lactamase is a cytosolic β-lactamase; contacting the cell with the test compound; contacting a sample comprising the cell or an extract of the cell with a β-lactamase substrate; and determining the amount of substrate cleaved, whereby the amount of substrate cleaved is related to the amount of β-lactamase activity. In one embodiment of the methods, the substrate is a compound of this invention. The step of determining the amount of substrate cleaved comprises exciting the compound; and determining the degree of fluorescence resonance energy transfer in the sample. A degree of fluorescence resonance energy transfer that is lower than an expected amount indicates the presence of β-lactamase activity.

In another aspect, this invention provides methods of clonal selection comprising providing cells transfected with a recombinant nucleic acid molecule comprising the expression control sequences operably linked to nucleic acid sequences coding for the expression of a cytosolic β-lactamase; contacting the cells with a substance that activates or inhibits the activation of the expression control sequences; contacting the cells with a compound of claim 9 which is converted into a substrate; determining whether substrate is cleaved within each individual cell, whereby cleavage reflects β-lactamase activity; selecting and propagating those cells with a selected level of β-lactamase activity. In a further embodiment, the method further involves culturing selected cells in the absence of activator for a time sufficient for cleaved substrate to be substantially lost from the cells and for β-lactamase levels to return to unactivated levels; incubating the selected cells with a compound of claim 9 which is converted into a substrate; and selecting cells that have not substantially cleaved the substrate.

BRIEF DESCRIPTION OF THE DRAWINGS

FIG. 7A presents a table describing various nucleotide and amino acid sequences useful in the invention.

FIG. 7B-C depicts Sequence 1, the nucleotide and deduced amino acid sequence of E. coli RTEM as modified by Kadonaga et al (1984).

FIG. 7D-E depicts Sequence 2, the nucleotide and deduced amino acid sequence of Wild-type secreted RTEM enzyme with Ser2→Arg, Ala23→Gly.

FIG. 7F-G depicts Sequence 3, the nucleotide and deduced amino acid sequence of RTEM enzyme with β-globin upstream leader, mammalian Kozak sequence, replacement of signal sequence by Met Gly.

FIG. 7H-I depicts Sequence 4, the nucleotide and deduced amino acid sequence of RTEM β-lactamase with mammalian Kozak sequence and replacement of signal sequence by Met Asp.

FIG. 7J-K depicts Sequence 5, the nucleotide and deduced amino acid sequence of Bacillus licheniformis β-lactamase with signal sequence replaced.

DESCRIPTION OF THE INVENTION

Definitions

Figure 1A:
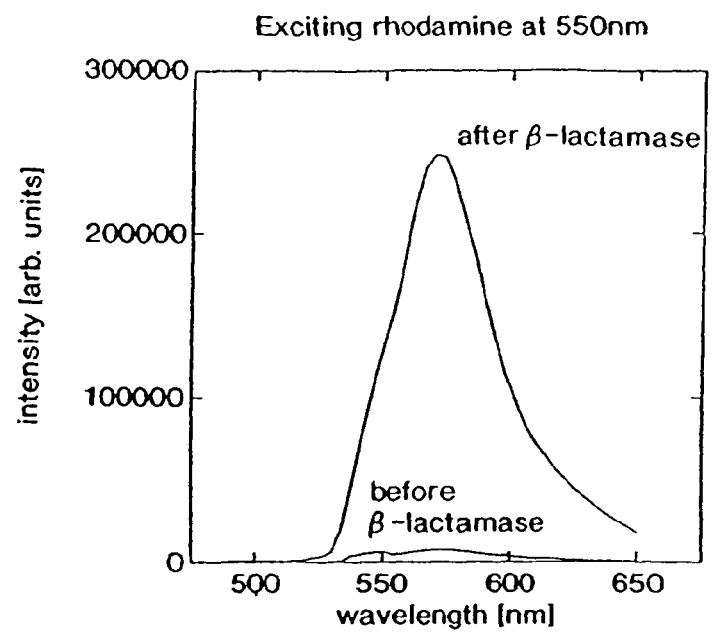
FIGS. 1(*a*) and 1(*b*) illustrate the emission spectra for the fluorescein (a) and rhodamine (b) components of compound 11 (Example 1) before and after β-lactamase cleavage of the β-lactam ring.

In accordance with the present invention and as used herein, the following terms are defined with the following meanings, unless stated otherwise.

The term "fluorescent donor moiety" refers the radical of a fluorogenic compound which can absorb energy and is capable of transferring the energy to another fluorogenic molecule or part of a compound. Suitable donor fluorogenic molecules include, but are not limited to, coumarins and related dyes xanthene dyes such as fluoresceins, rhodols, and rhodamines, resorufins, cyanine dyes, bimanes, acridines, isoindoles, dansyl dyes, aminophthalic hydrazides such as luminol and isoluminol derivatives, aminophthalimides, aminonaphthalimides, aminobenzofurans, aminoquinolines, dicyanohydroquinones, and europium and terbium complexes and related compounds.

The term "quencher" refers to a chromophoric molecule or part of a compound which is capable of reducing the emission from a fluorescent donor when attached to the donor. Quenching may occur by any of several mechanisms including fluorescence resonance energy transfer, photoinduced electron transfer, paramagnetic enhancement of intersystem crossing, Dexter exchange coupling, and exciton coupling such as the formation of dark complexes. The term "acceptor" as used herein refers to a quencher which operates via fluorescence resonance energy transfer. Many acceptors can re-emit the transferred energy as fluorescence. Examples include coumarins and related fluorophores, xanthenes such as fluoresceins, rhodols, and rhodamines, resorufins, cyanines, difluoroboradiazaindacenes, and phthalocyanines. Other chemical classes of acceptors generally do not re-emit the transferred energy. Examples include indigos, benzoquinones, anthraquinones, azo compounds, nitro compounds, indoanilines, di- and triphenylmethanes.

The term "dye" refers to a molecule or part of a compound which absorbs specific frequencies of light, including but not limited to ultraviolet light. The terms "dye" and "chromophore" are synonymous.

The term "fluorophore" refers to chromophore which fluoresces.

The term "membrane-permeant derivative" means a chemical derivative of a compound of general formula wherein at least one of X and Y contains at least one acylated aromatic hydroxyl, acylated amine, or alkylated aromatic hydroxyl wherein the acyl group contains 1 to 5 carbon atoms and wherein the alkyl group is selected from the group consisting of —CH$_2$OC(O)alk, —CH$_2$SC(O)alk, —CH$_2$OC(O)Oalk, lower acyloxy-alpha-benzyl, and deltabutyrolactonyl; wherein alk is lower alkyl of 1 to 4 carbon atoms. These derivatives are made better able to cross cell membranes, i.e. membrane permeant, because hydrophilic groups are masked to provide more hydrophobic derivatives. Also, the masking groups are designed to be cleaved from the fluorogenic substrate within the cell to generate the derived substrate intracellularly. Because the substrate is more hydrophilic than the membrane permeant derivative it is now trapped within the cells.

The term "alkyl" refers to straight, branched, and cyclic aliphatic groups of 1 to 8 carbon atoms, preferably 1 to 6 carbon atoms, and most preferably 1 to 4 carbon atoms.

The term "lower alkyl" refers to straight and branched chain alkyl groups of 1 to 4 carbon atoms.

The term "aliphatic" refers to saturated and unsaturated alkyl groups of 1 to 10 carbon atoms, preferably 1 to 6 carbon atoms, and most preferably 1 to 4 carbon atoms.

Substrates

β-Lactamases are nearly optimal enzymes in respect to their almost diffusion-controlled catalysis of β-lactam hydrolysis [Christensen, H. et al., *Biochem. J.* 266: 853-861 (1990)]. Upon examination of the other properties of this class of enzymes, it was determined that they were suited to the task of an intracellular reporter enzyme. They cleave the β-lactam ring of β-lactam antibiotics, such as penicillins and cephalosporins, generating new charged moieties in the process [O'Callaghan, C. H. et al., *Antimicrob.Agents.Chemother.* 8: 57-63, (1968); Stratton, C. W., *J. Antimicrob. Chemother.* 22. Suppl. A: 23-35 (1988)]. A first generation cephalosporin is illustrated below, left, with the arrow pointing to the site of cleavage by β-lactamase. The free amino group thus generated (middle structure below) donates electron density through the vinyl group to promote irreversible cleavage of a nucleofugal group R$_2$ from the 3'-position. R$_2$ is thus free to diffuse away from the R$_1$-cephalosporin conjugate (right-hand structure below).

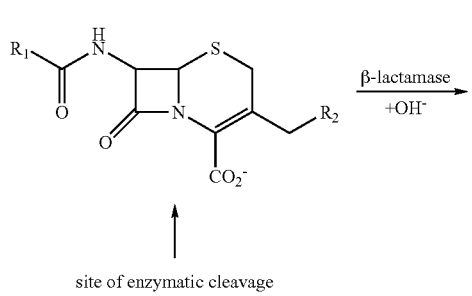

site of enzymatic cleavage

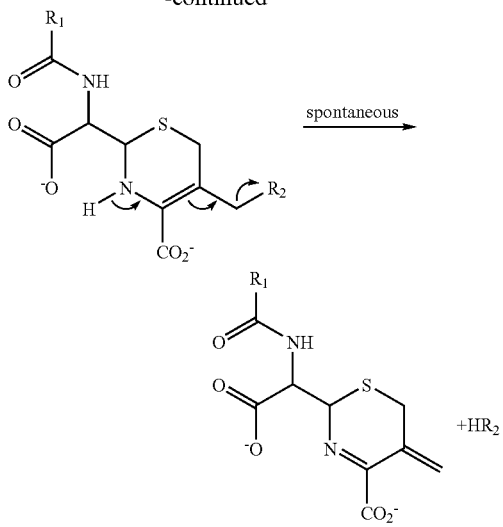

β-Lactamases are a class of enzymes that have been very well characterized because of their clinical relevance in making bacteria resistant to β-lactam antibiotics [Waley, S. G., Sci. Prog. 72: 579-597 (1988); Richmond, M. H. et al., Ann. N.Y. Acad. Sci. 182: 243-257 (1971)]. Most β-lactamases have been cloned and their amino acid sequence determined [see, e.g., Ambler, R. P., Phil. Trans. R. Soc. Lond. [Ser.B.] 289: 321-331 (1980)].

A gene encoding β-lactamase is known to molecular biologists as the ampicillin resistance gene ($Amp^r$) and is commonly used to select for successfully transduced bacteria [Castagnoli, L. et al., Genet. Res. 40: 217-231 (1982)]; clones thereof are almost universally available. The enzyme catalyzes the hydrolysis of a β-lactam ring and will not accept peptides or protein substrates [Pratt, R. F. and Govardhan, C. P., Proc. Natl. Acad. Sci. USA 81: 1302-1306 (1984); Murphy, B. P. and Pratt, R. F., Biochemistry 30: 3640-3649 (1991)]. The kinetics of this reaction is well understood and there is no product inhibition [Bush, K. and Sykes, R. B., Antimicrob. Agents. Chemother. 30: 6-10 (1986); Christensen et al. (1990), supra]. The enzyme substrates are less polar than the products.

The carboxyl group in the substrate can be easily masked by an acetoxymethyl ester [Jansen, A. B. A. and Russell, T. J., J. Chem. Soc. 2127-2132, (1965); Daehne, W. et al., J. Med. Chem. 13: 607-612 (1970)], which is readily cleaved by endogenous mammalian intracellular esterases. Conversion by these esterases followed by the β-lactam cleavage by β-lactamase generates two negative charges and a tertiary amine, which protonates. To date, there has been no report of a fluorogenic substrate with the appropriate properties, but multiple chromogenic substrates of different design have been reported and are commercially available [Jones, R. N. et al., J.Clin.Microbiol. 15: 677-683 (1982); Jones, R. N. et al., J.Clin.Microbiol. 15: 954-958 (1982); O° Callaghan, C. H. et al., Antimicrob.Agents.Chemother. 1: 283-288 (1972)].

A large number of β-lactamases have been isolated and characterized, all of which would be suitable for use in accordance with the present invention. Initially, β-lactamases were divided into different classes (I through V) on the basis of their substrate and inhibitor profiles and their molecular weight [Richmond, M. H. and Sykes, R. B., Adv.Microb. .Physiol. 9: 31-88 (1973)]. More recently, a classification system based on amino acid and nucleotide sequence has been introduced [Ambler, R. P., Phil. Trans. R. Soc. Lond. [Ser.B.] 289: 321-331 (1980)]. Class A β-lactamases possess a serine in the active site and have an approximate weight of 29 kd. This class contains the plasmid-mediated TEM β-lactamases such as the RTEM enzyme of pBR322. Class B β-lactamases have an active-site zinc bound to a cysteine residue. Class C enzymes have an active site serine and a molecular weight of approximately 39 kd, but have no amino acid homology to the class A enzymes.

The coding region of an exemplary β-lactamase employed in the reporter gene assays described herein is indicated in SEQ ID NO:1 (nucleic acid sequence) and SEQ ID NO:2 (amino acid sequence). The pTG2del1 containing this sequence has been described [Kadonaga, J. T. et al., J.Biol.Chem. 259: 2149-2154 (1984)]. The entire coding sequence of wildtype pBR322 β-lactamase has also been published [Sutcliffe, J. G., Proc.Natl.Acad.Sci.USA 75: 3737-3741 (1978)]. As would be readily apparent to those skilled in the field, this and other comparable sequences for peptides having β-lactamase activity would be equally suitable for use in accordance with the present invention. The β-lactamase reporter gene is employed in an assay system in a manner well known per se for the use of reporter genes (for example, in the form of a suitable plasmid vector).

In conjunction with a suitable β-lactamase, there are employed in accordance with the present invention fluorogenic substrates of the general formula I

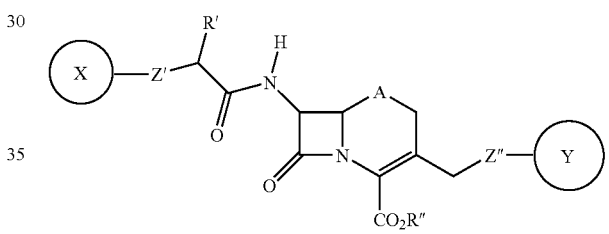

in which one of X and Y is a fluorescent donor moiety and the other is a quencher (which may or may not re-emit); R' is selected from the group consisting of H, lower alkyl, $(CH_2)_n$OH, $(CH_2)_n COOR''$, and =NOJ, in which n is 0 or an integer from 1 to 5 and J is H, Me, $CH_2COOH$, $CHMeCOOH$, and $CMe_2COOH$; R'' is selected from the group consisting of H, physiologically acceptable metal and ammonium cations, —$CHR^2OCO(CH_2)_nCH_3$, —$CHR^2OCOC (CH_3)_3$, acylthiomethyl, acyloxy-alpha-benzyl, delta-butyrolactonyl, methoxycarbonyloxymethyl, phenyl, methylsulphinylmethyl, beta-morpholinoethyl, dialkylaminoethyl, and dialkylaminocarbonyloxymethyl, in which $R^2$ is selected from the group consisting of H and lower alkyl; A is selected from the group consisting of S, O, SO, $S_2$ and $CH_2$; and Z' and Z'' are linkers for the fluorescent donor and quencher moieties.

The linkers Z' and Z'' serve the purpose of attaching the fluorescent donor and quencher moieties to the cephalosporin-derived backbone, and may facilitate the synthesis of the compounds of general formula I. In general formula I, Z' may represent a direct bond to the backbone; alternatively, suitable linkers for use as Z' include, but are not limited to, the following: —$(CH_2)_nCONR^2(CH_2)_m$—, —$(CH_2)_nNR^2CO(CH_2)_m$—, —$(CH_2)_nNR^3CONR^2(CH_2)_m$—, —$(CH_2)_nNR^3CSNR^2(CH_2)_m$—, —$(CH_2)_nCONR^3(CH_2)_pCONR^2(CH_2)_m$—, —$(CH_2)_n$—, —$(CH_2)_nNR^3CO$ $(CH_2)_pS$ $(CH_2)_m$—, —$(CH_2)_nS(CH_2)_m$—, —$(CH_2)_nO(CH_2)_m$—, —$(CH_2)_nNR^2(CH_2)_m$—, —$(CH_2)_nSO_2NR^2(CH_2)_m$—, —$(CH_2)_nCO_2(CH_2)_m$—,

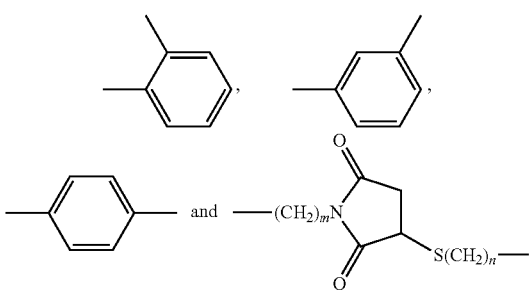

wherein $R^2$ and n are as previously defined; $R^3$ is selected from the group consisting of hydrogen and lower alkyl; and each of m and p is independently selected from the group consisting of 0 and integers from 1 to 4. Especially preferred are Z' groups such where n and m are 0. Also particularly preferred are such Z' groups where $R^2$ is H.

Suitable linkers Z" for the Y moiety include, but are not limited to, a direct bond to a heteroatom (e.g., O, N or S) in the dye's chromophore or the following: $-O(CH_2)_n-$, $-S(CH_2)_n-$, $-NR^2(CH_2)_n-$, $-N^+R^2{}_2(CH_2)_n-$, $-OCONR^2(CH_2)_n-$, $-O_2C(CH_2)_n-$, $-SCSNR^2(CH_2)_n-$, $-SCSO(CH_2)_n-$, $-S(CH_2)_nCONR^2(CH_2)_m$, $-S(CH_2)_nNR^2CO(CH_2)_m$, and

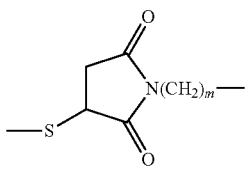

in which $R^2$, n and m are as previously defined; and m is an integer from 0 to 4. Particularly preferred Z" groups are $-S(CH_2)_n$. Especially preferred is H.

Preferred R' groups include H and methyl. Particularly preferred is H. Preferred R" groups include H and acetoxymethyl. A preferred $R^2$ group is H. A preferred A group is $-S-$.

In a preferred aspect, the compounds of the present invention are membrane-permeant. Particularly preferred are such compounds wherein at least one of X and Y contains at least one acylated aromatic hydroxyl, acylated amine, or alkylated aromatic hydroxyl wherein the acyl group contains 1 to 5 carbon atoms and wherein the alkyl group is selected from the group consisting of $-CH_2OC(O)alk$, $-CH_2SC(O)alk$, $-CH_2OC(O)Oalk$, lower acyloxy-alpha-benzyl, and delta-butyrolactonyl, wherein alk is lower alkyl of 1 to 4 carbon atoms. Particularly preferred are such compounds where at least one of X and Y contains at least one acylated aromatic hydroxy, wherein the acyl group is either acetyl, n-propionyl, or n-butyryl. Also particularly preferred are such compounds wherein at least one of X and Y contains an acetoxy methyl group on an aromatic hydroxyl group.

In another preferred aspect, the quencher or acceptor is a fluorescein, rhodol, or rhodamin of formulae VIII-XII. Preferred are such compounds where the donor is a fluorescein of formula VIII and the quencher or acceptor is a rhodol or rhodamine of formulae VIII-XII. Also preferred are such compounds where the donor is a fluorescein of formula VIII and the quencher or acceptor is a tetrahalo fluorescein of formula VIII in which $R^a$, $R^b$, $R^c$, and $R^d$ are independently Br or Cl. Also preferred are such compounds where the quencher or acceptor is a rhodol of formulae VIII, IX, and XI. Another preferred group of such compounds are those where the quencher or acceptor is a rhodamine of formulae VIII, X, and XII.

In a another preferred aspect, the donor is a coumarin of formulae II-VII and the quencher/acceptor is a fluorescein, rhodol, or rhodamine of formulae VIII-XII, XLVII, or XLVII, and membrane-permeant fluorogenic derivatives thereof. Particularly preferred are such compounds with a fluorescein quencher/acceptor of formula VIII. Especially preferred are such compounds where the coumarin is 7-hydroxycoumarin or 7-hydroxy-6-chlorocoumarin and the fluorescein acceptor is fluorescein or dichlorofluorescein.

As would readily be appreciated by those skilled in the art, the efficiency of fluorescence resonance energy transfer depends on the fluorescence quantum yield of the donor fluorophore, the donor-acceptor distance and the overlap integral of donor fluorescence emission and acceptor absorption. The energy transfer is most efficient when a donor fluorophore with high fluorescence quantum yield (preferably, one approaching 100%) is paired with an acceptor with a large extinction coefficient at wavelengths coinciding with the emission of the donor. The dependence of fluorescence energy transfer on the above parameters has been reported [Forster, T. (1948) Ann. *Physik* 2: 55-75; Lakowicz, J. R., *Principles of Fluorescence Spectroscopy*, New York: Plenum Press (1983); Herman, B., Resonance energy transfer microscopy, in: *Fluorescence Microscopy of Living Cells in Culture, Part B, Methods in Cell Biology*, Vol 30, ed. Taylor, D. L. & Wang, Y.-L., San Diego: Academic Press (1989), pp. 219-243; Turro, N. J., *Modern Molecular Photochemistry*, Menlo Part: Benjamin/Cummings Publishing Co., Inc. (1978), pp. 296-361], and tables of spectral overlap integrals are readily available to those working in the field [for example, Berlman, I. B. *Energy transfer parameters of aromatic compounds*, Academic Press, New York and London (1973)]. The distance between donor fluorophore and acceptor dye at which fluorescence resonance energy transfer (FRET) occurs with 50% efficiency is termed $R_0$ and can be calculated from the spectral overlap integrals. For the donor-acceptor pair fluorescein-tetramethyl rhodamine which is frequently used for distance measurement in proteins, this distance $R_0$ is around 50-70 Å [dos Remedios, C. G. et al. (1987) *J. Muscle Research and Cell Motility* 8:97-117]. The distance at which the energy transfer in this pair exceeds 90% is about 45 Å. When attached to the cephalosporin backbone the distances between donors and acceptors are in the range of 10 Å to 20 Å, depending on the linkers used and the size of the chromophores. For a distance of 20 Å, a chromophore pair will have to have a calculated $R_0$ of larger than 30 Å for 90% of the donors to transfer their energy to the acceptor, resulting in better than 90% quenching of the donor fluorescence. Cleavage of such a cephalosporin by β-lactamase relieves quenching and produces an increase in donor fluorescence efficiency in excess of tenfold. Accordingly, it is apparent that identification of appropriate donor-acceptor pairs for use as taught herein in accordance with the present invention would be essentially routine to one skilled in the art.

To measure β-lactamase activity in the cytoplasm of living cells, smaller molecular weight chromophores as hereinafter described are in general preferred over larger ones as substrate delivery becomes a problem for larger compounds. Large molecules, especially those over about 1200 daltons, also tend to bind more avidly to cellular constituents than small ones, thereby removing at least some of them from access and cleavage by β-lactamase.

Chromophores suitable for use as X and Y are well known to those skilled in the art. Generic structures of particular classes of chromophores suitable for use as X and Y are provided below. Compounds of general formulas II-XXXIV are exemplary of fluorophores which serve as the basis for particularly suitable donor moieties in the compounds of general formula I. Suitable chromophores for use as the basis of acceptor moieties in the compounds of general formula include, but are not limited to, compounds of general formulas II-LIV. Chromophores of general formulae XXXV-LIV usually do not re-emit efficiently.

Coumarins and related dyes

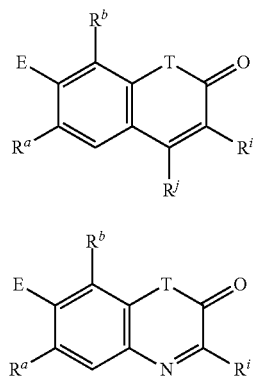

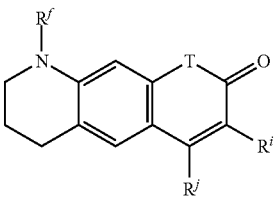

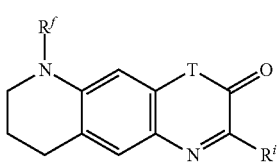

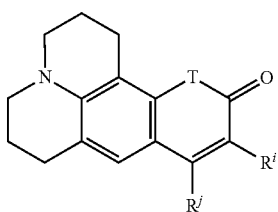

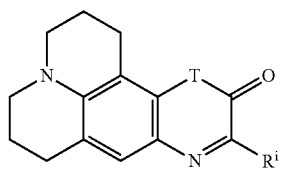

Xanthene dyes including fluoresceins, rhodols and rhodamines)

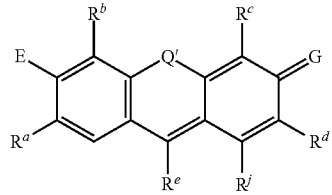

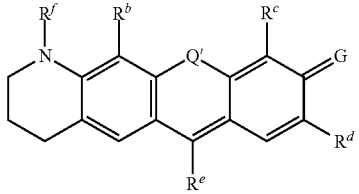

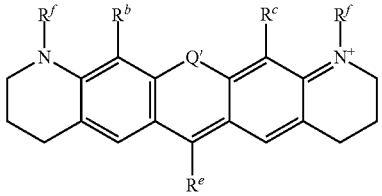

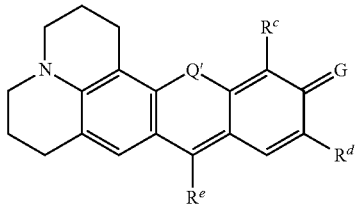

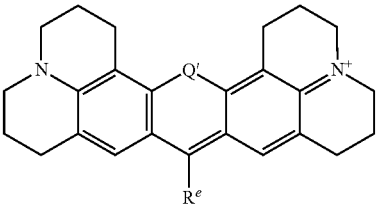

Resorufins

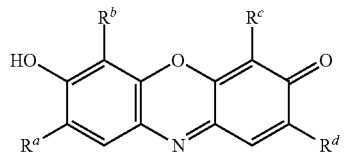

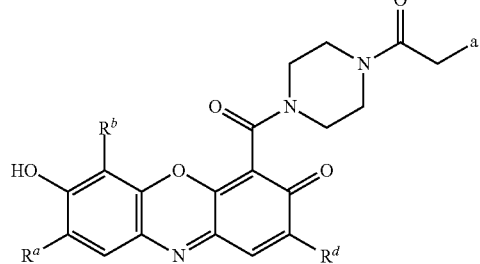

Cyanine dyes
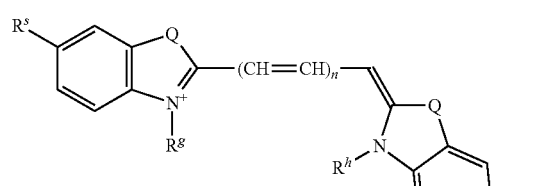
XV
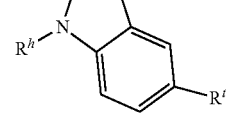
XVI
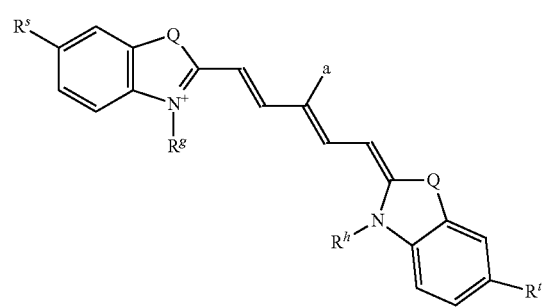
XVII
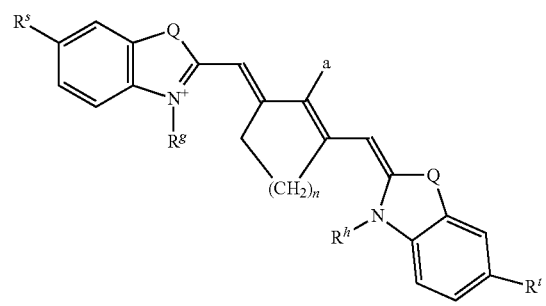
Difluoroboradiazaindacene dyes
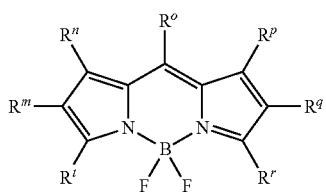
XVIII
Bimanes
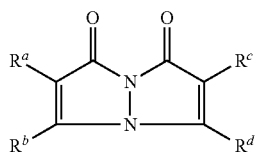
XIX
Acridines
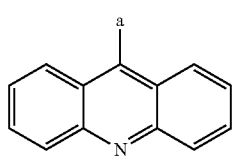
XX
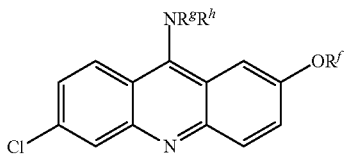
XXI
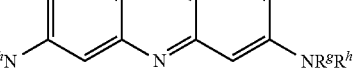
XXII
Isoindoles
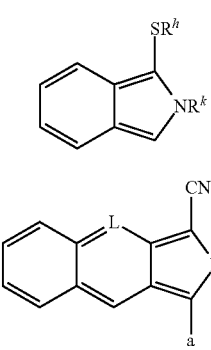
XXIII
XXIV
Dansyl dyes
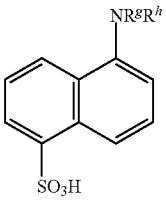
XXV
XXVI
Aminophthalic hydrazides (luminol and isoluminol derivatives)
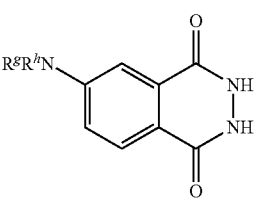
XXVII
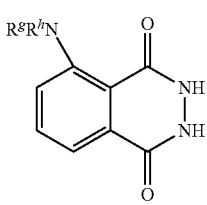
XXVIII -continued
Aminophthalimides
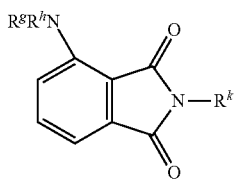
XXIX
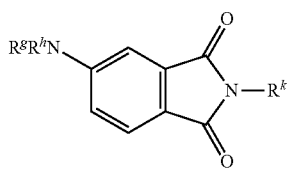
XXX
Aminonaphthalimides
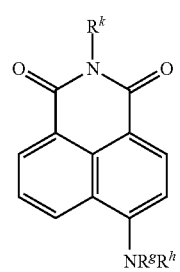
XXXI
Aminobenzofurans
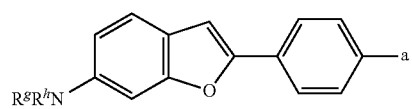
XXXII
Aminoquinolines
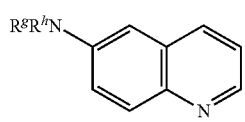
XXXIII
Dicyanohydroquinones
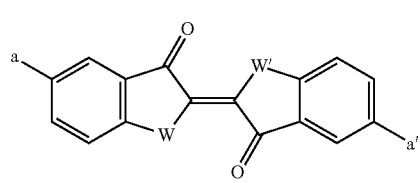
XXXIV
Indigo dyes
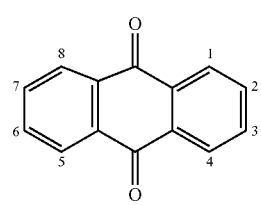
XXXV
Anthraquinone dyes
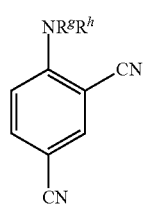
Polymethine dyes
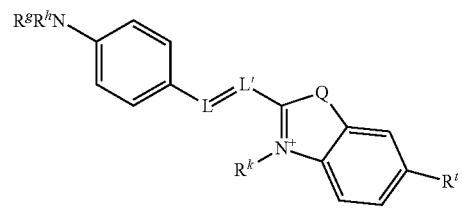
XXXVII
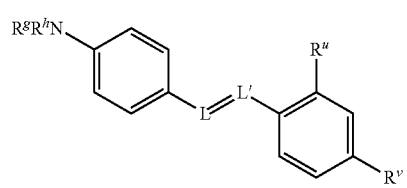
XXXVIII
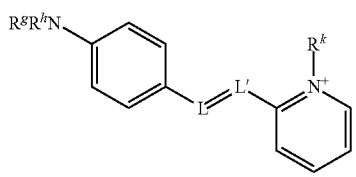
XXXIX
Nitro dyes and cyano derivatives
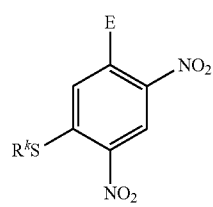
XL
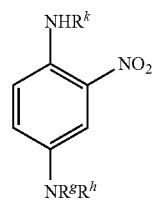
XLI
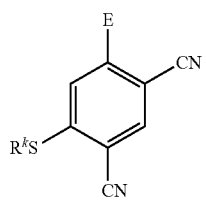
XLII
XLIII Quinone dyes XLIV
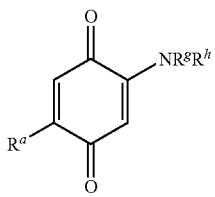

XLV
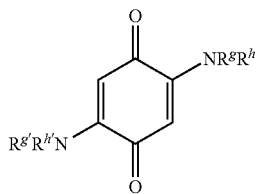

Xanthene dyes

XLVI
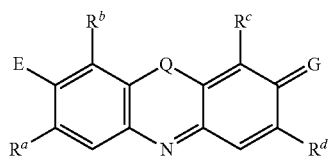

XLII
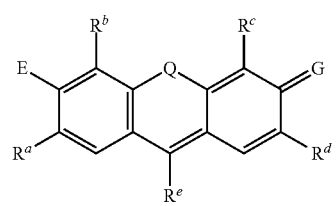

Dicyanovinyl and tricyanovinyl dyes

XLVIII
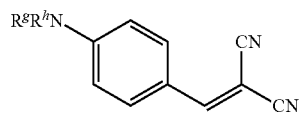

XLIX
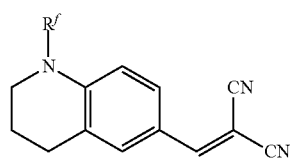

L
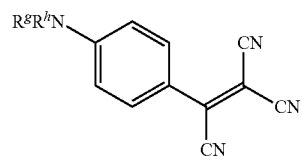

LI
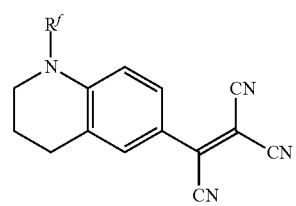

Indoaniline dyes (ninhydrin derivatives)

LII
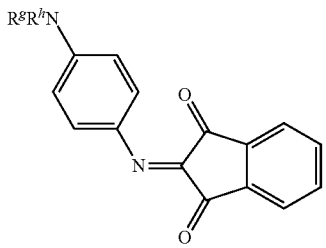

Di- and triphenylmethane dyes

LIII
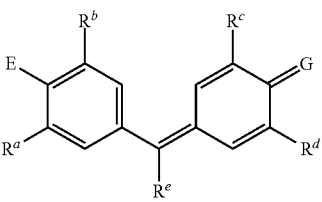

Indamines and related dyes

LIV
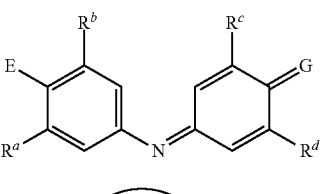

LV
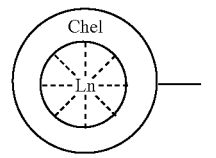

LVI
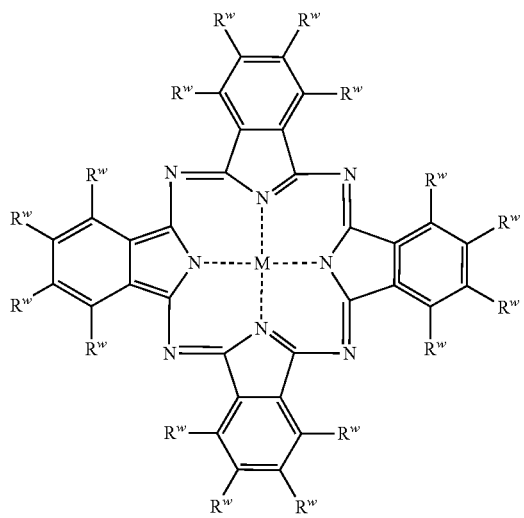

⟨?⟩ indicates text missing or illegible when filed

In preferred embodiments of the compounds of general formulas II-LVI:

each of a and a' is independently H or an attachment point (i.e., a location at which the dye moiety is attached to the core structure of general formula I;

E is selected from the group consisting of H, OH, $OR^k$ and $NR^gR^h$;

G is selected from the group consisting of O and $N^+R^{g'}R^{h'}$;

each of L and L' is independently selected from the group consisting of CH and N;

M is selected from the group consisting of H, Mg, Al, Si, Zn, and Cu;

Q is selected from the group consisting of O, S, $C(CH_3)_2$ and $NR^g$;

Q' is selected from the group consisting of O, $CH_2$, $C(CH_3)_2$, $NR^k$ and $SO_2$;

T is selected from the group consisting of O and $NR^k$;

each of W and W' is selected from the group consisting of O, S, Se and NH;

each of $R^a$, $R^b$, $R^c$ and $R^d$ is independently selected from the group consisting of an attachment point, H, halogen and lower alkyl;

$R^e$ is selected from the group consisting of an attachment point, H, lower alkyl, $(CH_2)_nCO_2H$, $(CH_2)_nCHaCO_2H$, $CHa(CH_2)_nCO_2H$, $(CH_2)_nCOa$, $CH=CHCOa$,

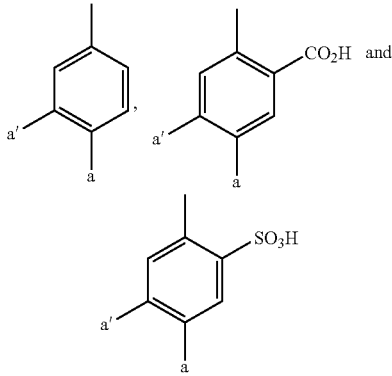

each of $R^f$, $R^g$, $R^{g'}$, $R^h$, $R^{h'}$ and $R^k$ is independently selected from the group consisting of an attachment point, H, lower alkyl and $CH_2(CH_2)_na$;

$R^i$ is selected from the group consisting of an attachment point, H, halogen, lower alkyl, CN, $CF_3$, phenyl, $CO_2H$ and $CONR^gR^{h'}$;

$R^j$ is selected from the group consisting of an attachment point, H, halogen, lower alkyl, CN, $CF_3$, phenyl, $CH_2CO_2H$, $CH_2CONR^gR^{h'}$;

each of $R^l$ and $R^r$ is independently selected from the group consisting of an attachment point, H, lower alkyl,

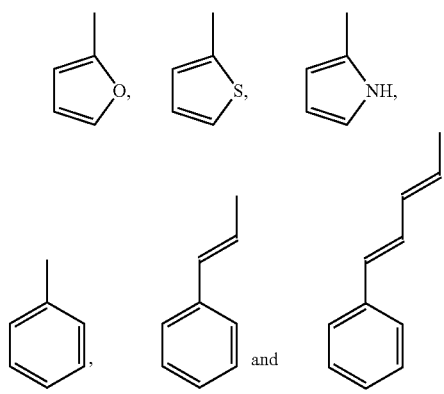

each of $R^m$, $R^n$, $R^p$ and $R^q$ is independently selected from the group consisting of an attachment point, H, lower alkyl and phenyl;

$R^o$ is selected from the group consisting of an attachment point, H and lower alkyl;

each of $R^s$ and $R^t$ is independently selected from the group consisting of an attachment point, H, halogen, lower alkyl and $OR^f$;

each of $R^u$ and $R^v$ is independently selected from the group consisting of an attachment point, H, halogen, CN and $NO_2$;

each of $R^w$ is independently selected from the group consisting of an attachment point, H, $COO^-$, $SO_3^-$, and $PO_3^{2-}$ Ln is selected from the group consisting of $Eu^{3+}$, $Ln^{3+}$, and $Sm^{3+}$;

Chel is a polydentate chelator with at least six and preferably eight to ten donor atoms that can face into a cavity of diameter between 4 and 6 angstroms, which may or may not be macrocyclic, which includes a chromophore absorbing between 300 and 400 nm, and which includes an attachment point through which Chel can be conjugated to Z' or Z". A suitable Chel moiety is a europium tris-(bipyridine) cryptands. In the anthraquinone chromophores of general formula XXXIX, each of positions 1-8 may carry a substituent H or E, or serve as an attachment point.

Europium tris-(bipyridine)cryptand donors may be suitably paired with acceptors of the formulae XV-XVII, XXXVI, XLVI-XLVII, LIV, and LVI. Terbium tris-(bipyridine) cryptand donors may be suitably paired with acceptors of the formulae VIII-XVIII, XXXVI-XLI, and XLV-LIV, and LVI.

The Europium tris-(bipyridine) cryptand/phtalocyanines donor/acceptor pair may be of particular interest when it is desirable to measure β-lactamase activity by emission of energy in the near to far red range.

In many applications it is desirable to derivatize compounds of general formula I to render them hydrophobic and permeable through cell membranes. The derivatizing groups should undergo hydrolysis inside cells to regenerate the compounds of general formula I and trap them inside the cells. For this purpose, it is preferred that any phenolic hydroxyls or free amines in the dye structures are acylated with $C_1$-$C_4$ acyl groups (e. g. formyl, acetyl, n-butryl) or converted to various other esters and carbonates [for examples, as described in Bundgaard, H., *Design of Prodrugs*, Elsevier Science Publishers (1985), Chapter I, page 3 et seq.]. Phenols can also be alkylated with 1-(acyloxy)alkyl, acylthiomethyl, acyloxy-alpha-benzyl, deltabutyrolactonyl, or methoxycarbonyloxymethyl groups. In the case of fluoresceins, rhodols, and rhodamines this manipulation is particularly useful, as it also results in conversion of the acid moiety in these dyes to the spirolactone. To promote membrane permeation, the carboxyl at the 4-position of the cephalosporin should be esterified with 1-(acyloxy)alkyl, acylthiomethyl, acyloxy-alpha-benzyl, delta-butyrolactonyl, methoxycarbonyloxymethyl, phenyl, m ethylsulfinylmethyl, beta-morpholinethyl, 2-(dimethylamino)ethyl, 2-(diethylamino)ethyl, or dialkylaminocarbonyloxymethyl groups as discussed in Ferres, H. (1980) *Chem. Ind.* 1980: 435-440. The most preferred esterifying group for the carboxyl is acetoxymethyl.

A general method for synthesis of compounds of general formula I is depicted below. As one of ordinary skill in the art will appreciate, the methods below can be used for a variety of derivatives, and other methods of synthesis are possible.

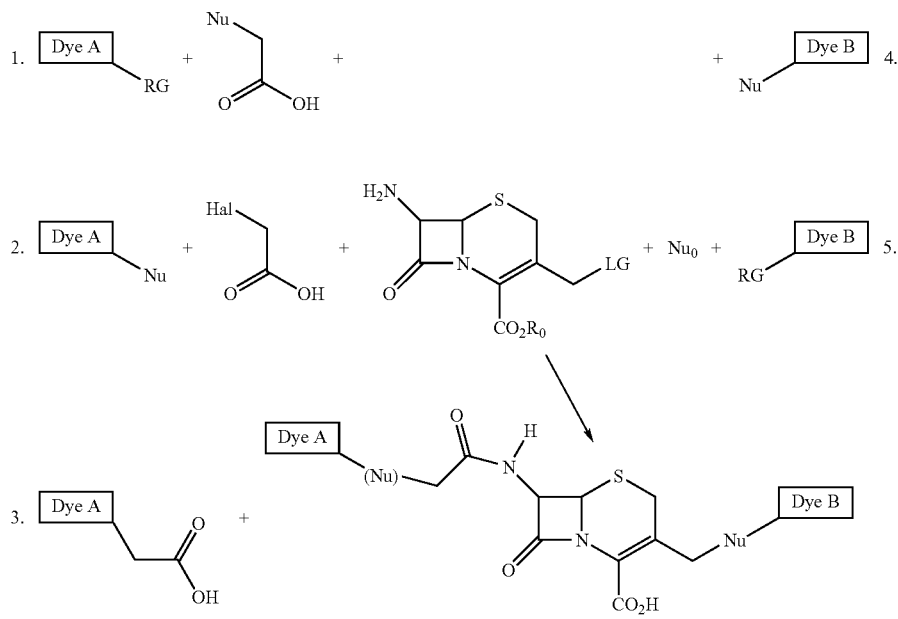

In these compounds, RG is a nucleophile-reactive group (e.g., iodoacetamide, isocyanate, isothiocyanate, etc.); Nu is a nucleophile (e.g., —SH, —NH$_2$, —OH, etc.); R$_0$ is H or an ester group (e.g., benzhydryl ester, tertiary butyl ester, etc.); Nu$_0$ is a bidentate nucleophile (e.g., HS$^-$, HSCH$_2$CH$_2$NH$_2$, xanthate, etc.); and Hal is a halogen (e.g., chlorine, bromine or iodine).

The cephalosporin starting materials are commercially available cephalosporin derivatives 7-aminocephalosporanic acid or 7-amino 3'-chloro-cephalosporanic acid as its benzhydryl or tertiary butyl ester (R$_0$). Prior to coupling the dyes A and B carrying nucleophile reactive groups (RG) it is sometimes advantageous to esterify or alkylate their phenolic and free amine residues. The order of attaching dye A and dye B depends on the choice of reagents. Dye A is tethered to the cephalosporin via an alkyl amide linker. This is achieved by reacting a dye A carrying a nucleophile-reactive group (RG) with a bifunctional aliphatic acid (e.g., amino-, mercapto- or hydroxyalkyl acid) and coupling of the acid to the cephalosporin 7-amine (path 1). Alternatively, dye A carrying a nucleophilic group (e.g., amine or thiol) is reacted with a halogenated alkyl acid and the acid coupled to the cephalosporin 7-amine (path 2). In both pathways, the order of the two reactions can be reversed. Dyes A containing an aliphatic acid can be directly coupled to the cephalosporin (path 3). Dye B carrying a nucleophilic substituent can be coupled to the 3'-position in the cephalosporin by direct displacement of the leaving group (LG) (path 4). A Dye B carrying a nucleophile-reactive group can be reacted with a bidentate nucleophile which is coupled then attached to the cephalosporin by leaving group (LG) displacement (path 5); the order of the reactions can be reversed.

In some cases it might be necessary to conduct tne first reaction with a bidentate nucleophile with one of its nucleophilic groups masked. The second coupling is then performed after removal of that protection group. After attachment of both dyes the cephalosporin ester is cleaved (in cases where R$_0$ is not H). To make membrane permeant substrates the acid is then re-esterified to esters that can be deprotected by the cytoplasmic environment of a mammalian cell. For applications not involving cell cytoplasm, any remaining acyl and alkyl groups that were used to mask phenols and free amines on the dyes are removed.

Preferred combinations of classes of donors and acceptors suitable for use in accordance with the present invention are indicated in Table 1. In embodiments of compounds of general formula I using these combinations, fluorescent resonant energy transfer (FRET) occurs. Of course, as would be readily understood by those working in the field, many other combinations of donors and acceptors/quenchers (including those that re-emit and those that do not) would be suitable for use in accordance with the present invention. In general, suitable donor and acceptor pairs are those where the donor's emission spectrum significantly overlaps the acceptor's excitation spectrum.

TABLE 1

| DONORS | ACCEPTORS | | |
|---|---|---|---|
| | II-VIII, XIX-XXI, XXIII-XXXIV | VII-XIV, XVII, XXII | XV-XVI, LV |
| II - VIII, XIX-XXI, XXIII-XXXIV | FRET | | |
| VII-XIV, XVII, XXII | FRET | FRET | |
| XV-XVII XL-XLV, XLVII-LII | FRET FRET | FRET FRET | FRET |
| XXXV-XXXIX, XLVI-XLVII, LIII-LIV, LVI | FRET | FRET | FRET |

Fluorescent donor moieties of particular interest include coumarins and fluoresceins. Particular quenchers of interest include fluoresceins, rhodols and rhodamines. Combinations of interest include the use of a coumarin donor with a fluorescein, rhodol or rhodamine quencher, and a fluorescein donor with a rhodol or rhodamine quencher. Specific combinations of interest include the following: a coumarin (e. g., 7-hydroxycoumarin) or chloro derivative thereof with a fluorescein or dichloro derivative thereof; a fluorescein with an eosin or tetrachlorofluorescein; a fluorescein with a rhodol derivative; ahd a rhodamine with a fluorescein.

Europium chelate donors may be suitably paired with acceptors of the formulae XV-XVII, XXXVI, XLVI-XLVII, LIV, and LVI. Terbium chelate donors may be suitably paired with acceptors of the formulae VIII-XVIII, XXXVI-XLI, and XLV-LIV, and LVI. The europium and terbium chelate donors may be of particular interest for their very narrow emission peaks and their microsecond-to-millisecond excited state lifetimes, which can be readily discriminated from background fluorescence and scattering with excited-state lifetimes of nanoseconds or less.

In many applications it is desirable to derivatize compounds of general formula I to render them more hydrophobic and permeable through cell membranes. The derivatizing groups should undergo hydrolysis inside cells to regenerate the compounds of general formula I and trap them inside the cells. For this purpose, it is preferred that any phenolic hydroxyls or free amines in the dye structures are acylated with $C_1$-$C_4$ acyl groups (e.g. formyl, acetyl, n-butyryl) or converted to various other esters and carbonates [for example, as described in Bundgaard, H., *Design of Prodrugs*, Elsevier Science Publishers (1985), Chapter 1, page 3 et seq. ]. Phenols can also be alkylated with 1-(acyloxy)alkyl, acylthiomethyl, acyloxy-alpha-benzyl, delta-butyrolactonyl, or methoxycarbonyloxymethyl groups. In the case of fluoresceins, rhodols and rhodamines, acylation or alkylation of the free phenolic groups is particularly useful, as it also results in conversion of the acid moiety in these dyes to the spirolactone. To promote membrane permeation, the carboxyl at the 4-position of the cephalosporin should be esterified with 1-(acyloxy)alkyl, acylthiomethyl, acyloxy-alpha-benzyl, delta-butyrolactonyl, methoxycarbonyloxymethyl, phenyl, methylsulfinylmethyl, beta-morpholinoethyl, 2-(dimethylamino)ethyl, 2-(diethylamino)ethyl, or dialkylaminocarbonyloxymethyl groups as discussed in Ferres, H. (1980) *Chem. Ind.* 1980: 435-440. The most preferred esterifying group for the carboxyl is acetoxymethyl.

The cephalosporin backbone serves as a cleavable linker between two dyes. After cleavage it provides the charges necessary to keep one of the two dyes inside the cell. Dyes are chosen in a manner that one dye absorbs light (quencher or acceptor chromophore) at the wavelength that the other one emits (donor fluorophore). In the intact cephalosporin the two dyes are in close proximity to each other. When exciting the donor fluorophore one observes fluorescence resonance energy transfer (FRET) from the donor to the acceptor instead of donor fluorescence [Forster, T., *Ann. Physik* 2: 55-75 (1948)]. If the acceptor is a nonfluorescent dye the energy is given off to the solvent; the donor fluorescence is quenched. In the case of the acceptor being itself a fluorescent dye, fluorescence re-emission occurs at the acceptor's emission wavelength. In polar solvents such as water, hydrophobic donor and acceptor fluorophores can stack when separated by a short flexible linker. Due to this association in the ground state, a "dark complex" is formed [Yaron, A. et al., *Anal. Biochem.* 95: 228-235 (1979)]. In this complex, neither fluorophore can emit light, causing the fluorescence of both dyes to be quenched [Bojarski, C. and Sienicki, K. Energy transfer and migration in fluorescent solutions. In: *Photochemistry and Photophysics*, edited by Rabek, J. F. Boca Raton: CRC Press, Inc., 1990, pp. 1-57]. In either case, a large change in fluorescence goes along with β-lactam cleavage, which can be used to measure β-lactamase activity. As both dyes diffuse away from each other, stacking and energy transfer are disrupted. Cephalosporins carrying a donor and an acceptor dye which fluoresces are referred to herein as FRET-cephalosporins.

Fluorescence resonance energy transfer has been used as a spectroscopic ruler for measuring molecular distances in proteins and peptides as it is effective in the range from 10-100 Å. This energy transfer is proportional to the inverse sixth power of the distance between donor and acceptor. Its efficiency is higher, the better donor emission and acceptor absorbance overlap, and the longer the fluorescence lifetime of the donor (in absence of the acceptor). FRET can be very efficient over distances of 10-20 Å.

In the cephalosporin, distances for attachment of donor and acceptor are greater than 10 Å and a minimum of 10 bond-lengths, if one includes the two minimal spacers at 7-and 3-positions. Over this distance FRET is very efficient, if the right donor-acceptor pairs are chosen. Conveniently, in a FRET-cephalosporin the 7-amine tethered dye stays attached to the polar hydrolysis products of cephalosporin cleavage, trapping it in the cells' cytoplasm. This position is best occupied by the donor fluorophore, although in some instances the acceptor may occupy this position. Upon cleavage, fluorescence increases due to loss of the quencher dye.

The acceptor fluorophore is generally attached by a linker which imparts the greatest stability of the substrate to nucleophilic attack. A preferred linker is a thioether bond (—S—), which is very stable and due to its inductive effect reduces the reactivity of the β-lactam ring toward nucleophiles [Page, M. I., *Adv. Phys. Org. Chem.* 23: 165-270 (1987)]. In addition, the free thiol or thiolate group released upon hydrolysis often quenches the attached fluorophore, adding to the desired large change in fluorescence upon hydrolysis.

The fluorogenic substrates of the invention are initially colorless and nonfluorescent outside cells. The substrates are designed so they readily cross cell membranes into the cytoplasm, where they are converted to fluorescent compounds by endogenous nonspecific esterases and stay trapped due to their charges. In the intact molecules, fluorescence energy transfer occurs leading to fluorescence at a particular wavelength when the substrates are excited. Lactamase cleavage of the β-lactam ring is followed by expulsion of the fluorescein moiety with loss of fluorescence energy transfer. Excitation of the modified substrate now results in fluorescence at a different wavelength.

The assay systems of the present invention further provide an advantageous and rapid method of isolation and clonal selection of stably transfected cell lines containing reporter genes and having the desired properties which the transfection was intended to confer, e.g. fluorescent signal response after activation of a transfected receptor with a high signal-to-noise ratio from a high proportion of isolated cells. Current procedures for clonal selection of satisfactorily transfected, genetically engineered cells from the initial population, are done mainly by replica plating of colonies, testing of one set of colonies, visual selection of preferred clones, manual isolation of the replicas of the preferred clones by pipetting, and prolonged cellular cultivations. This procedure is laborious and time-consuming; it may require several months to generate a clone useful for assays suited to drug screening. Moreover, it is difficult to manually select and maintain more than a few hundred clones. Using the assays of this present invention, the desired signal from cellular beta-lactamase reporter system can be maintained within living and viable cells. Replica plating of colonies is unnecessary because single cells can be assayed and remain viable for further multiplication. Thus, from the population of initially transfected cells, one can rapidly select those few individual living cells with the best fluorescent signal, using automated instruments such as a fluorescent-activated cell sorter, e.g. the Becton Dickinson FACS Vantage™. The selected cells are then collected for cultivation and propagation to produce a clonal cell line with the desired properties for assays and drug screening.

As would be immediately apparent to those working in the field, the combination of a novel substrate in accordance with the invention and a suitable β-lactamase may be employed in a wide variety of different assay systems (such as are described in U.S. Pat. No. 4,740,459). In particular, the fluorogenic substrates of the invention enable the detection of β-lactamase activity in a wide variety of biologically important environments, such as human blood serum, the cytoplasm of cells and intracellular compartments; this facilitates the measurement of periplasmic or secreted β-lactamase.

Further, the expression of any target protein can be detected by fusing a gene encoding the target protein to a β-lactamase gene, which can be localized by immunostaining and fluorescence or electron microscopy. For example, β-lactamase fusion proteins may be detected in the lumen of organelles through the use of the substrates of the invention; only subcellular compartments containing the fusion protein fluoresce at a wavelength characteristic of the cleaved substrate, whereas all others fluoresce at a wavelength characteristic of the intact molecule.

Both the intact and cleaved substrate are well retained in cells without the use of special measures, such as chilling. The color change (even in individual small mammalian cells) is visible through a fluorescence microscope using normal color vision or photographic film; the fluorescence signal may be quantified and further enhanced by conventional digital image processing techniques. Moreover, because gene activation is detected not by a change in a single intensity but rather by a color change or a change in the ratio between two intensities at different wavelengths, the assays of the present invention are relatively immune to many artifacts such as variable leakiness of cells, quantity of substrate, illumination intensity, absolute sensitivity of detection and bleaching of the dyes.

A variety of substrates (e.g., compounds of general formulas 17, 22 and 25) have been prepared and their emission spectra obtained before and after β-lactamase cleavage. These substrates allow for β-lactamase detection primarily in vitro, as they bind strongly to serum and cellular proteins. Due to their hydrophobic nature, the fluorophores stack; this leads to a loss of fluorescence in the intact substrate. β-lactamase cleaves the substrates and relieves the stacking, allowing for fluorescence. Compounds (e.g., compound 11, Example 1) with reversed location of donor and acceptor fluorophore on the cephalosporin exhibit similar fluorescence behavior.

In one preferred embodiment of the invention, a compound of general formula 1 was coupled to a compound of general formula 2 to form a compound of general formula 3. Commercially-available compound 4 was then coupled to compound 3 using dicyclohexylcarbodiimide and the product reacted with compound 5, yielding a compound of general formula 6. Deprotection of compound 6 generated a compound of general formula 7. In exemplary embodiments, Acyl was acetyl, $R^x$ was Me and $R^y$ H (a), or Acyl was butyryl, $R^x$ was H and $R^y$ Cl (b); $R^z$ was trimethylsilyl or benzyl.

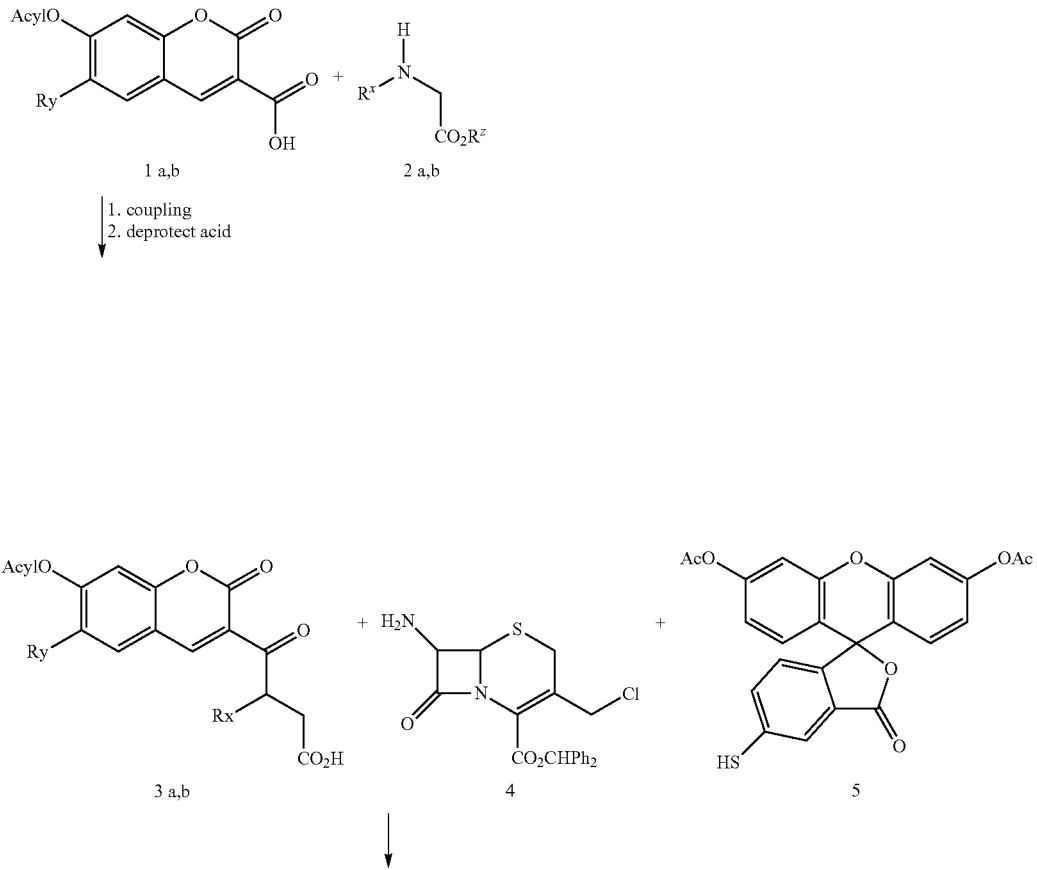

-continued

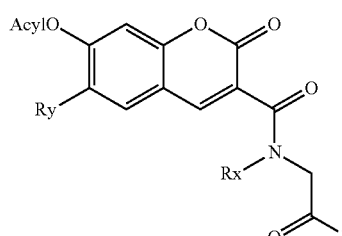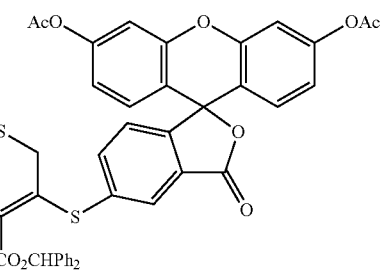

6 a,b

↓ deprotect

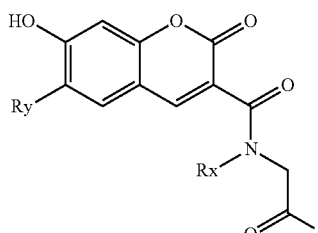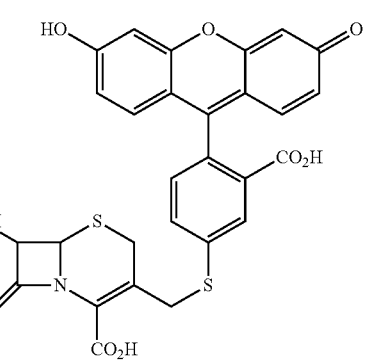

7 a,b

The compounds of general formula 6 were modified to obtain membrane permeant derivatives which were converted to the corresponding fluorescent compounds of general formula 7 in intact cells due to the action of endogenous non-specific esterases. In these molecules, fluorescence resonance energy transfer occurs from the 7-hydroxycoumarin moiety to the fluorescein moiety, leading to green fluorescence when the compounds are excited at about 400 nm. After cleavage of the β-lactam ring, excitation of the 7-hydroxycoumarin moiety results in blue fluorescence; in exemplary embodiments, a 25-fold increase in fluorescence at about 450 nm and a three- to fourfold decrease in fluorescence at 515 nm was observed.

Monitoring Gene Expression

The substrates of this invention make it feasible to use β-lactamase as a reporter gene to monitor the expression from a set of expression control sequences. In one aspect, this invention provides methods for monitoring gene expression from a set of expression control sequences by using β-lactamase as a reporter gene. A cell is provided that has been transfected with a recombinant nucleic acid molecule comprising the expression control sequences operably linked to nucleic acid sequences coding for the expression of β-lactamase.

Recombinant Nucleic Acids As used herein, the term "nucleic acid molecule" includes both DNA and RNA molecules. It will be understood that when a nucleic acid molecule is said to have a DNA sequence, this also includes RNA molecules having the corresponding RNA sequence in which "U" replaces "T." The term "recombinant nucleic acid molecule" refers to a nucleic acid molecule which is not naturally occurring, and which comprises two nucleotide sequences which are not naturally joined together. Recombinant nucleic acid molecules are produced by artificial combination, e.g., genetic engineering techniques or chemical synthesis.

Figure 1B:
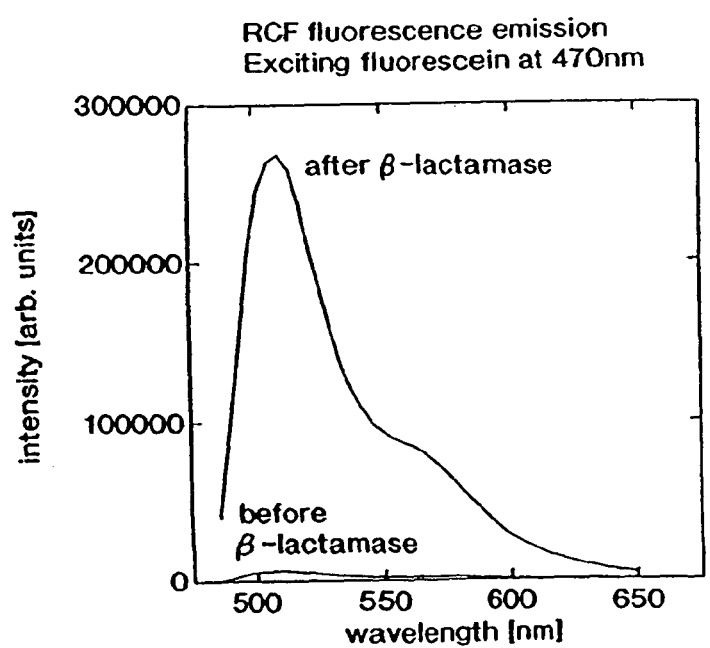

Nucleic acids encoding β-lactamases can be obtained by methods known in the art, for example, by polymerase chain reaction of cDNA using primers based on the DNA sequence in FIG. 1. PCR methods are described in, for example, U.S. Pat. No. 4,683,195; Mullis et al. (1987) *Cold Spring Harbor Symp. Quant. Biol.* 51:263; and Erlich, ed., *PCR Technology*, (Stockton Press, NY, 1989).

The construction of expression vectors and the expression of genes in transfected cells involves the use of molecular cloning techniques also well known in the art. Sambrook et al., *Molecular Cloning—A Laboratory Manual*, Cold Spring Harbor Laboratory, Cold Spring Harbor, N.Y., (1989) and *Current Protocols in Molecular Biology*, F. M. Ausubel et al., eds., (Current Protocols, a joint venture between Greene Publishing Associates, Inc. and John Wiley & Sons, Inc., (most recent Supplement)).

Nucleic acids used to transfect cells with sequences coding for expression of the polypeptide of interest generally will be in the form of an expression vector including expression control sequences operatively linked to a nucleotide sequence coding for expression of the polypeptide. As used, the term nucleotide sequence "coding for expression of" a polypeptide refers to a sequence that, upon transcription and translation of mRNA, produces the polypeptide. As any person skilled in the are recognizes, this includes all degenerate nucleic acid sequences encoding the same amino acid sequence. This can include sequences containing, e.g., introns. As used herein, the term "expression control sequences" refers to nucleic acid sequences that regulate the expression of a nucleic acid sequence to which it is operatively linked. Expression control sequences are "operatively linked" to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the MRNA, and stop codons.

The recombinant nucleic acid can be incorporated into an expression vector comprising expression control S sequences operatively linked to the recombinant nucleic acid. The expression vector can be adapted for function in prokaryotes or eukaryotes by inclusion of appropriate promoters, replication sequences, markers, etc.

The recombinant nucleic acid used to transfect the cell contains expression control sequences operably linked to a nucleotide sequence encoding a β-lactamase. The β-lactamase encoded can be any known to the art or described herein. This includes, for example, the enzymes shown in FIG. 7.

This invention provides novel recombinant nucleic acid molecules including expression control sequences adapted for function in a non-mammalian eukaryotic cell operably linked to a nucleotide sequence coding for the expression of a cytosolic β-lactamase. As used herein, "cytosolic β-lactamase" refers to a β-lactamase that lacks amino acid sequences for secretion from the cell membrane, e.g., the signal sequence. For example, in the polypeptide of Sequence 1 of FIG. 7, the signal sequence has been replaced with the amino acids Met-Ser. Accordingly, upon expression, this β-lactamase remains within the cell.

This invention provides recombinant nucleic acid molecules including expression control sequences adapted for function in a mammalian eukaryotic cell operably linked to a nucleotide sequence coding for the expression of a β-lactamase.

It is further preferable that the ribosome binding site and nucleotide sequence coding for expression of β-lactamase contain sequences preferred by mammalian cells. Such sequences improve expression of β-lactamase in mammalian cells. Preferred sequences for expression in mammalian cells are described in, for example, Kozak, M., *J. Cell Biol.* 108: 229-241 (1989), referred to herein as "Kozak sequences". The nucleotide sequence for cytosolic β-lactamase in Sequence 3 of FIG. 7 contains Kozak sequences for the nucleotides −9 to 4 (GGTACCACCATGA).

When used in mammalian cells, the expression control sequences are adapted for function in mammalian cells. The method of this invention is useful to testing expression from any desired set of expression control sequences. In particular, this invention is useful for testing expression from inducible expression control sequences. As used herein, "inducible expression control sequences" refers to expression control sequences which respond to biochemical signals either by increasing or decreasing the expression of sequences to which they are operably linked. For example, in the case of genes induced by steroid hormones, the expression control sequences includes hormone response elements. The binding of a steroid hormone receptor to the response element induces transcription of the gene operably linked to these expression control sequences. Expression control sequences for many genes and for inducible genes, in particular, have been isolated and are well known in the art. The invention also is useful with constitutively active expression control sequences.

The transfected cell is incubated under conditions to be tested for expression of β-lactamase from the expression control sequences. The cell or an extract of the cell is contacted with a β-lactamase substrate of the invention under selected test conditions and for a period of time to allow catalysis of the substrate by any β-lactamase expressed. Then the donor moiety from this sample is excited with appropriate ultraviolet or visible wavelengths. The degree of fluorescence resonance energy transfer in the sample is measured.

If the cell did not express β-lactamase, very little of the substrate will have been cleaved, the efficiency of FRET in the cell will be high, and the fluorescence characteristics of the cell or sample from it will reflect this efficiency. If the cell expressed a large amount of β-lactamase, most of the substrate will be cleaved. In this case, the efficiency of FRET is low, reflecting a large amount or high efficiency of the cleavage enzyme relative to the rate of synthesis of the tandem fluorescent protein construct. In one aspect, this method can be used to compare mutant cells to identify which ones possess greater or less enzymatic activity. Such cells can be sorted by a fluorescent cell sorter based on fluorescence.

Also, as will be apparent to those working in the field of using reporter gene cell-based assays for screening samples or pools of samples (such as compounds (combinatorial or synthetic), natural product extracts, or marine animal extracts) to identify potential drug candidates which act as agonists, inverse agonists or antagonists of cellular signaling or activation, the combination of cells (preferably mammalian) genetically engineered to express beta-lactamase under the control of different regulatory elements/promoters and the use of the novel beta-lactamase substrate compounds of the present invention will provide distinct advantages over known reporter genes (including, but not limited to, chloramphenicol acetyl transferase, firefly luciferase, bacterial luciferase, Vargula luciferase, aequorin, beta-galactosidase, alkaline phosphatase) and their requisite substrates.

By the choice of appropriate regulatory elements and promoters to control expression of beta-lactamase, assays can be constructed to detect or measure the ability of test substances to evoke or inhibit functional responses of intracellular hormone receptors. These include expression control sequences responsive to inducible by mineralcorticosteroids, including dexamethasone [*J. Steroid Biochem. Molec. Biol.* Vol. 49, No. 1 1994, pp. 31-3]), gluococorticoid, and thyroid hormone receptors [as described in U.S. Pat. No. 5,071,773]. Additional such intracellular receptors include retinoids, vitamin D3 and vitamin A [Leukemia vol 8, Suppl. 3, 1994 ppS1-S10; Nature Vol. 374, 1995, p. 118-119; Seminars in Cell Biol., Vol. 5, 1994, p. 95-103]. Specificity would be enabled by use of the appropriate promoter/enhancer element. Additionally, by choice of other regulatory elements or specific promoters, drugs which influence expression of specific genes can be identified. Such drugs could act on specific signaling molecules such as kinases, transcription factors, or molecules such signal transducers and activators of transcription [Science Vol. 264, 1994, p. 1415-1421; *Mol. Cell Biol.*, Vol. 16, 1996, p. 369-375]. Specific microbial or viral promoters which are potential drug targets can also be assayed in such test systems.

Also by the choice of promoters such as c-fos or c-jun [U.S. Pat. No. 5,436,128; *Proc. Natl. Acad. Sci.* Vol. 88, 1991, pp. 5665-5669] or promoter constructs containing regulatory elements responsive to second messengers [*Oncogene*, 6: 745-751 (1991)] (including cyclic AMP-responsive elements, phorbol ester response element (responsive to protein kinase C activation), serum response element (responsive to protein kinase C-dependent and independent pathways) and Nuclear Factor of Activated T-cells response element (responsive to calcium) to control expression of beta-lactamase, assays can be constructed to detect or measure substances or mixtures of substances that modulate cell-surface receptors including, but not limited to, the following classes: receptors of the cytokine superfamily such as erthyropoietin, growth hormone, interferons, and interleukins (other than IL-8) and colony-stimulating factors; G-protein coupled receptors [U.S. Pat No. 5,436,128] for hormones, such as calcitonin, epinephrine or gastrin, pancrine or autocrine mediators, such as stomatostatin or prostaglandins, and neurotransmitters such as norepinephrine, dopamine, serotonin or acetylcholine; tyrosine kinase receptors such as insulin growth factor, nerve growth factor [U.S. Pat. No. 5,436,128]. Furthermore, assays can be constructed to identify substances that modulate the activity of voltage-gated or ligand-gated ion channels, modulation of which alters the cellular concentration of second messengers, particularly calcium [U.S. Pat. No. 5,436,128]. Assays can be constructed using cells that intrinsically express the promoter, receptor or ion channel of interest or into which the appropriate protein has been genetically engineered.

The expression control sequences also can be those responsive to substances that modulate cell-surface receptors or that modulate intra-cellular receptors.

To measure whether a substance or mixture of substances activates extracellular or intracellular receptors or other cellular responses, cells containing beta-lactamase controlled by a desired promoter/enhancer element are incubated with test substance(s), substrate then added, and after a certain period of time the fluorescence signal is measured at either one or two excitation-emission pairs appropriate to the chosen compound of the invention (e.g. compound CCF2 with wavelength pairs of near 405 nm and near 450 nm and near 405 and near 510 nm). This fluorescent result is compared to control samples which have had no drug treatment and, when feasible, control samples with a known inhibitor and a known activator. The effect of any active drugs is then determined using the ratio of the fluorescence signal found in test wells to the signals found in wells with no drug treatment. Assays are performed in wells in a microtiter plate containing 96 or more wells or in an assay system with no compartments such as a gel matrix or moist membrane environment. Detection could be done for example by microtiter plate fluorimeters, e.g. Millipore Cytofluor, or imaging devices capable of analyzing one or more wells or one or more assay points in a certain surface area, e.g. as supplied by Astromed. The ability to retain the substrate in the cytoplasm of living cells is advantageous as it can allow a reduction in signal interference from coloured or quenching substances in the assay medium. Furthermore, the fluorescent signal from the compounds of this invention, such as CCF2, can be readily detected in single cells and thus allowing assay miniaturization and an increased number of tests per surface area. Miniaturized assays also further increase the throughput of an imaging detection system as there are more samples within the imaging field.

The assay systems of the present invention further provide an advantageous and rapid method of isolation and. clonal selection of stably transfected cell lines containing reporter genes and having the desired properties which the transfection was intended to confer, e.g. fluorescent signal response after activation of a transfected receptor with a high signal-to-noise ratio of at least 10:1 from a high proportion of isolated cells. Current procedures for clonal selection of satisfactorily transfected, genetically engineered cells from the population initial transfected with the vectors of interest, are done mainly by manual means and involve several rounds of microscopic analyses, selecting the visually preferred clone, isolation of the clone by manual pipetting stages and prolonged cellular cultivations. This procedure is laborious and time-consuming; it may require several months to generate a clone useful for assays suited to drug screening. Moreover, it is difficult to manually select and maintain more than a few hundred clones. Using the assays of this present invention, the desired signal from cellular beta-lactamase reporter system can be maintained within living and viable cells. Thus, one can rapidly select, from the population of initially transfected cells, those few living cells with the best fluorescent signal using automated instruments such as a fluorescent-activated cell sorter, e.g. the Becton Dickinson FACS Vantage. The selected cells are then collected for cultivation and propagation to produce a clonal cell line with the desired properties for assays and drug screening.

In addition, the presence (for example, in human serum, pus or urine) of bacteria resistant to β-lactam antibiotics can be readily detected using the substrates of the present invention. Only in the presence of an active β-lactamase is there a change in the fluorescence spectrum from that of the intact molecule to one characteristic of the cleavage product. The substrates of the present invention are superior to prior art chromogenic substrates Nitrocephin and PADAC, in that the inventive substrates are stable to human serum. The novel substrates are also more sensitive than the chromogenic substrate CENTA, because they experience a much smaller optical background signal from human serum and a lower detection limit for fluorescence versus absorbance.

The invention may be better understood with reference to the accompanying examples, which are intended for purposes of illustration only and should not be construed as in any sense limiting the scope of the invention as defined in the claims appended hereto.

Measurements

The degree of FRET can be determined by any spectral or fluorescence lifetime characteristic of the excited construct, for example, by determining the intensity of the fluorescent signal from the donor, the intensity of fluorescent signal from the acceptor, the ratio of the fluorescence amplitudes near the acceptor's emission maxima to the fluorescence amplitudes near the donor's emission maximum, or the excited state lifetime of the donor. For example, cleavage of the linker increases the intensity of fluorescence from the donor, decreases the intensity of fluorescence from the acceptor, decreases the ratio of fluorescence amplitudes from the acceptor to that from the donor, and increases the excited state lifetime of the donor.

Preferably, changes in the degree of FRET are determined as a function of the change in the ratio of the amount of fluorescence from the donor and acceptor moieties, a process referred to as "ratioing." Changes in the absolute amount of substrate, excitation intensity, and turbidity or other background absorbances in the sample at the excitation wavelength affect the intensities of fluorescence from both the donor and acceptor approximately in parallel. Therefore the ratio of the two emission intensities is a more robust and preferred measure of cleavage than either intensity alone.

The excitation state lifetime of the donor moiety is, likewise, independent of the absolute amount of substrate, excitation intensity, or turbidity or other background absorbances. Its measurement requires equipment with nanosecond time resolution, except in the special case of lanthanide complexes in which case microsecond to millisecond resolution is sufficient.

Additional suitable Chel moieties are described in Vallarino, L. M., & Leif, R. C., U.S. Pat. No. 5,373,093; Sabbatini, N. et al, *Pure and Applied Chem.* 67: 135-140 (1995); Mathis, G., *Clinical Chem.* 41: 1391-1397 (1995); Horiguchi, D., *Chem. Pharm. Bull.* 42: 972-975 (1994); Takalo, H. et al, *Bioconjugate Chem.* 5: 278-282 (1994); Saha, A. K. et al, *J. Amer. Chem. Soc.* 115: 11032 (1993); Li, M. & Selvin, P. R., *J. Amer. Chem. Soc.* 117: 8132-8138 (1995).

Fluorescence in a sample is measured using a fluorimeter. In general, excitation radiation, from an excitation source having a first wavelength, passes through excitation optics. The excitation optics cause the excitation radiation to excite the sample. In response, fluorescent proteins in the sample emit radiation which has a wavelength that is different from the excitation wavelength. Collection optics then collect the emission from the sample. The device can include a temperature controller to maintain the sample at a specific temperature while it is being scanned. According to one embodiment, a multi-axis translation stage moves a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation.

Methods of performing assays on fluorescent materials are well known in the art and are described in, e.g., Lakowicz, J. R., *Principles of Fluorescence Spectroscopy*, New York: Plenum Press (1983); Herman, B., Resonance energy transfer microscopy, in: *Fluorescence Microscopy of Living Cells in Culture, Part B, Methods in Cell Biology*, vol. 30, ed. Taylor, D. L. & Wang, Y.-L., San Diego: Academic Press (1989), pp. 219-243; Turro, N. J., *Modern Molecular Photochemistry*, Menlo Park: Benjamin/Cummings Publishing Col, Inc. (1978), pp. 296-361.

EXAMPLES

All silica gel chromatography was performed using silica gel (Merck, grade 60, 230-400 mesh, 60 Å) purchased from Aldrich. Bakerbond Octadecyl from J. T. Baker was used for $C_{18}$ reverse phase chromatography. Solvents (high pressure liquid chromatography grade) were used for chromatography as received, or dried over activated molecular sieves (3 Å) for synthetic purposes.

Fluorescence excitation and emission spectra were measured either on a Spex Fluorolog 111 or on a K2 fluorometer (ISS, Champaigne, Ill.) in ratio mode with a rhodamine B quantum counter. The efficiency of fluorescence energy transfer was determined from the change in the integrated fluorescence emission at the donor emission wavelength upon treatment with β-lactamase. For fluorescence microscopy imaging, two different imaging setups were used. One, with an inverted fluorescence microscope, Zeiss IM-35 (Thornwood, N.Y.) coupled to a silicon-intensified target (SIT) camera (Dage-MTI, Michigan City, Ind.) has been described in detail [Tsien, R. Y. (1986) New tetracarboxylate chelators for fluorescence measurement and photochemical manipulation of cytosolic free calcium concentrations, in: *Optical Methods in Cell Physiology*, ed. de Weer, P. & Salzberg, B., New York: Wiley, pp. 327-345; Tsien and Harootunian (1990) *Cell Calcium* 11:93-109]. The other consisted of a cooled charge-coupled-device. (CCD) camera (Photometrics, Tucson, Ariz.) connected to an inverted fluorescence microscope (Zeiss Axiovert).

Fluorescence resonance energy transfer was measured by monitoring the ratio of fluorescence intensities at donor and acceptor emission wavelengths using commercially-available filters (Omega Optical).

Excitation: 360 DF 40, dichroic mirror 390 DCLP or 405 DF 15, dichroic mirror 420 DRLPO2
Emission: 450 DF 65 (donor emission) 515 EFLP (acceptor emission) 435 EFLP (to view donor and acceptor fluorescence simultaneously)

Example 1

Compound 11

To test the optical properties of a cephalosporin with two dye molecules attached the following model compound was synthesized.

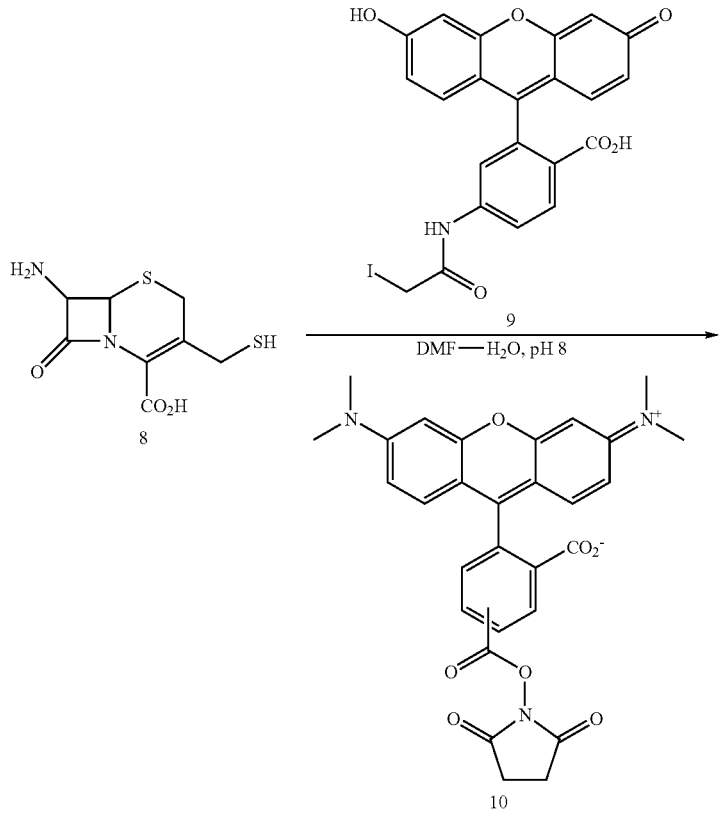

-continued

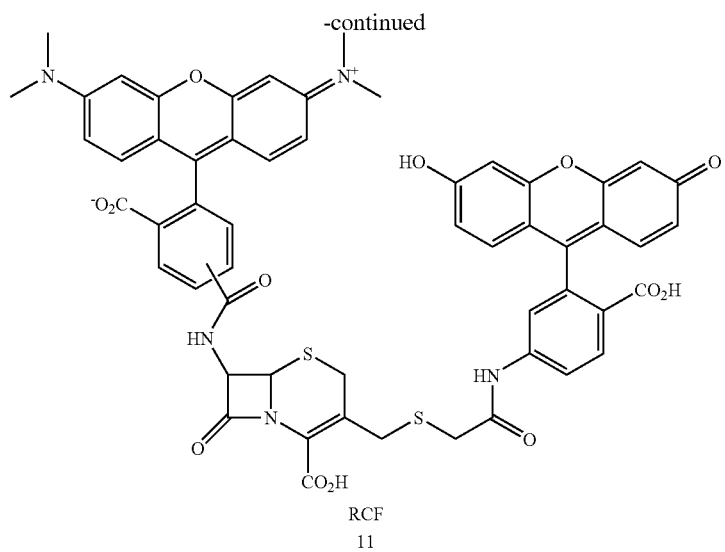

RCF
11

The first synthesis step was to convert 7-aminocephalosporanic acid into a bifunctional cephalosporin carrying a thiol in the 3'-position and the 7-amine [Van Heyningen, E. and Brown, C. N., *J. Med. Chem.* 8: 174-181 (1965); Japanese Patent, Kokai 75/18494, CA 85, 97320d]. This cephalosporin was then reacted selectively with an thiol-reactive dye, followed by an amine-reactive dye. The thiol-reactive dye 5,(6)-iodoacetamido-fluorescein and the amine-reactive dye 5,(6)-carboxy -N,N,N',N'-tetramethylrhodamine-succinimide were coupled to the cephalosporin in aqueous dimethylformamide at pH 8. The product will be referred to as RCF.

In phosphate buffer at pH 7 RCF is virtually non fluorescent; neither fluorescein nor rhodamine show much fluorescence when excited at their respective excitation maxima, which is indicative of chromophore stacking ("dark complex"). After long term treatment with β-lactamase the β-lactam is cleaved causing the fluorescence of both dyes to reappear (FIGS. 1(a) and 1(b)). This experiment confirms that one can measure β-lactamase catalyzed hydrolysis of the β-lactam in cephalosporins by the loss of fluorescence quenching using an appropriate donor-acceptor pair.

Example 2

The thiomethyl linker was introduced by conversion of 5-fluoresceinamine to 5-mercaptofluorescein via diazotization, conversion to the ethylxanthate, and degradation of the xanthate by aqueous acid to the free sulfhydryl. It was coupled to 7-bromoacetamido -cephalosporanic acid by nucleophilic displacement of the bromide by the mercapto group of the fluorescein. 7-Bromoacetamido-cephalosporanic acid had been prepared from 7-aminocephalosporanic acid and bromoacetyl bromide [Bunnell, C. A. et al. Industrial manufacture of cephalosporins. In: *Beta-Lactam Antibiotics for Clinical Use. Series: Clinical Pharmacology Vol.* 4, edited by Queener, S. F., Webber, J. A. and Queener, S. W. New York: M. Dekker, 1986, p. 255-283].

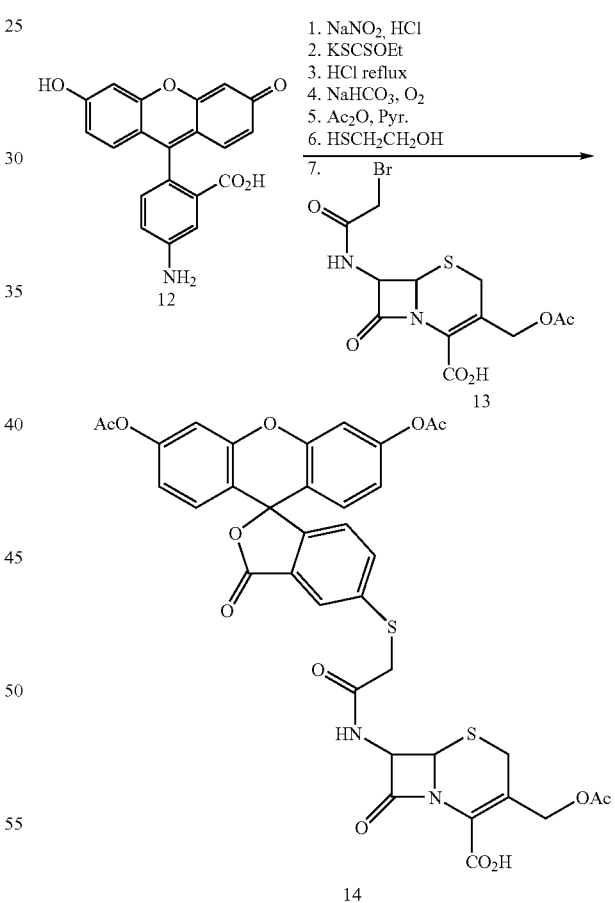

To prepare 7β-[(5-diacetylfluorescein)thiol]acetamido-3-(acetoxymethyl) -3-cephem-4-carboxylic acid (14), in a nitrogen atmosphere 130 mg (0. 29 mmol) 5-fluoresceinthiol diacetate were dissolved in 10 ml dimethylformamide and added to 120 mg (0.31 mmol) 7β-bromoacetamido-3-(acetoxymethyl)-3-cephem-4-carboxylic acid in 10 ml 1M potassium phosphate buffer adjusted to pH 8. 0. The solution was stirred for 8 hours at room temperature after which the solvents were removed in vacuo. The residue was dissolved in 10 ml water and the pH of the solution was carefully adjusted to pH 5 with dilute phosphoric acid. At this point nonpolar byproducts precipitated and were removed by centrifugation. Further acidification to pH 2.7 precipitated the title compound which was collected by centrifugation, washed 3 times with 2 ml diethylether -tetrachloromethane (1:2), and dried in vacuo. $^1$H NMR (CDCl$_3$): δ 2.08 ppm (s, 3H, acetate), δ 3.36 ppm, 3.53 ppm (2d, 2H, J=17.3 Hz, C-2), δ 3.87 ppm (s, 2H, side chain methylene), δ 4.88 ppm, 5.16 ppm (2d, 2H, J=13.6 Hz, C-3'), δ 4.96 ppm (d, 1H, J=4.9 Hz, C-6), δ 5.81 ppm (dd, 1H, J$_1$=8.2 Hz, J$_2$=4.9 Hz, C-7), δ 6.85 ppm (m, 4H, xanthene), δ 7.10 ppm (s, 2H, xanthene), δ 7.15 ppm (d, 1H, J=8.2 Hz, amide), δ 7.69 ppm (d, 1H, J=8.2 Hz, phthalic), δ 7.91 ppm (d, 1H, J=8.2 Hz, phthalic), δ 8.11 ppm (s, 1H, phthalic).

5-Fluoresceinamine was brominated to generate 5-eosinamine, which was converted into 5-mercaptoeosin in analogous way to the 5-mercaptofluorescein. In a nucleophilic displacement of the cephalosporin acetate by 5-mercaptoeosin diacetate the FRET-cephalosporin was generated as the protected tetraacetyl derivative.

white precipitate began to form. An ice-cooled trap attached to the flask kept bromine from escaping into the atmosphere. Excess bromine was then recovered by distillation into a liquid nitrogen cooled collecting flask. One volume of water was added to the acetic acid solution to precipitate any product remaining in solution. The precipitate was collected by filtration and dissolved in 1N aqueous sodium hydroxide. 5-Eosinamine was precipitated as the free amine by addition of glacial acetic acid. The eosinamine was dissolved in little chloroform and methanol was added. Concentrating this solution on the rotary evaporator gave 2.56 g (3.85 mmol, 77%) eosinamine as a fine white powder (the eosinamine-spirolactone).

To prepare 5-eosin-ethylxanthate diacetate, 670 mg (1 mmol) 5-eosinamine were stirred in 2 ml concentrated sulfuric acid and 2 ml glacial acetic acid. The suspension was cooled with an ice-salt bath to a few degrees below 0° C., which turned it into a thick paste that was difficult to stir. 200 mg (2.9 mmol) sodium nitrite in 1 ml water were added dropwise over the period of one hour. After another 2 hours at 0° C. 20 g of ice was slowly added. The flask was put on the

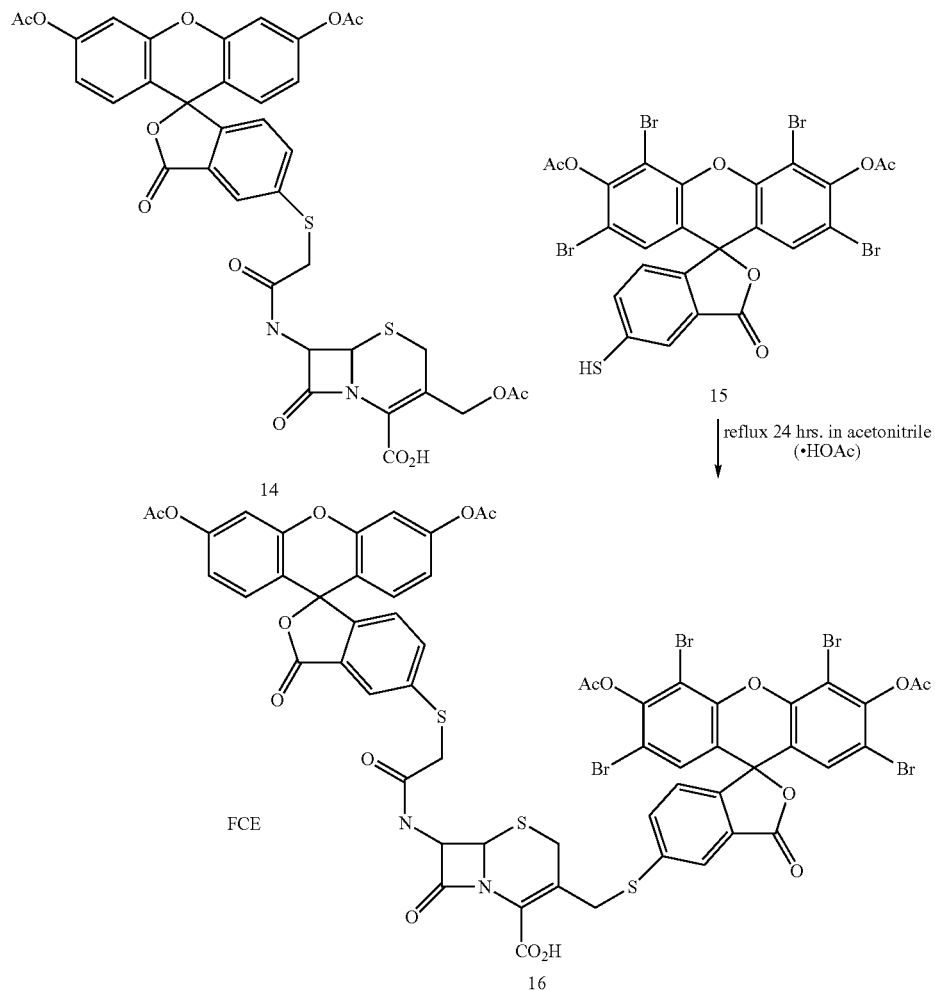

To prepare 5-eosinamine, 1.74 g (5 mmol) 5-fluoresceinamine was suspended in 30 ml glacial acetic and 2.06 ml (40 mmol, 100% excess) bromine was added. With the addition of bromine the fluoresceinamine went into solution. The solution was heated for six hours at 90° C., during which period a high vacuum pump in the cold, to remove excess nitrous gases (caution!!). Saturated ice-cold aqueous sodium bicarbonate solution was added until the solids dissolved into the dark red solution. 200 mg (1.2 mmol) Potassium ethylxanthate was added and a pink precipitate formed (5-eosindiazonium xanthate). A few crystals of nickel(II)chloride catalyzed the conversion of the diazonium salt with evolution of nitrogen. Once nitrogen evolution had ceased the products were precipitated with 1N hydrochloric acid. The precipitate was collected by filtration and dried in vacuo. It was treated with acetic anhydride-pyridine (1:1) at 40° C. for one hour. After removal of the reagents in vacuo, the residue was chromatographed over silica gel with ethyl acetate-hexane (1:4) as eluent. The desired product eluted first. The yield was 110 mg (0.13 mmol, 13%) of the title compound as a white powder.

For preparation of the disulfide dimer of 5-eosinthiol diacetate (dimer of 15), 110 mg (0.13 mmol) 5-eosin-ethylxanthate diacetate was stirred in 10 ml concentrated (30%) aqueous ammonia and the solution was heated to 70° C. Air was bubbled slowly through the solution to oxidize the thiol to the disulfide in situ. After 2 hours the solvents were removed on the rotary evaporator at 40° C. and the residue was treated with acetic anhydride-pyridine (1:1). After removal of the reagents in vacuo the residue was chromatographed over silica gel with ethyl acetate-hexane (1:4) as the eluent. Yield was 90 mg (60 µmol, 91%) of the title product as a white powder. The compound was reduced to the monomer (15) by dissolving it in methanol with addition of sodium acetate and addition of 20 equivalents mercaptoethanol. After 2 hours the methanolic solution was poured into 3 volumes 5% aqueous acetic acid from which the precipitating 5-fluoresceinthiol monomer was collected by centrifugation. The solid was washed with water until no odor of mercaptoethanol remained.

Coupling of diacetyl 5-eosinthiol (15) with 7β-[(5-diacetylfluorescein)thio]acetamido-3-(acetoxymethyl)-3-cephem-4-carboxylic acid (14) and deacylation with acetylesterase was effected as follows. 10 mg (13 µmol) 7β-[(5-Diacetylfluorescein)thio]acetamido-3-(acetoxymethyl)-3-cephem-4-carboxylic acid and 10 mg (13 µmol) diacetyl-5-eosinthiol were dissolved in 200 µl dry acetonitrile and the solution was sealed under argon in a glass tube. The tube was kept in an oil bath at 84° C. (±2° C.) for 16 hours. Then it was cut open, the solution transferred to a flask and the solvent removed in vacuo. The residue was flash-chromatographed over silica gel with ethyl acetate-methanol-acetic acid (100:1:1) as the eluent. Deprotection of the acetates was achieved by incubating the product with orange peel acetylesterase in 50 mM phosphate buffer (pH7) for 24 hours at 37° C. The deacylated product was purified by $C_{18}$ reverse phase chromatography. The eluent was a step gradient of 25 mM aqueous phosphate buffer (pH7) and methanol. Fluorescein byproducts eluted with 33% and 50% methanol in the eluent, after which the desired product eluted in 66% methanol.

The deprotected compound shows little fluorescence in phosphate buffer as the two hydrophobic dyes stack. The remaining fluorescence is due to fluorescence resonance energy transfer (FRET). This compound is a good substrate for RTEM β-lactamase and will be referred to as FCE.

Figure 2:
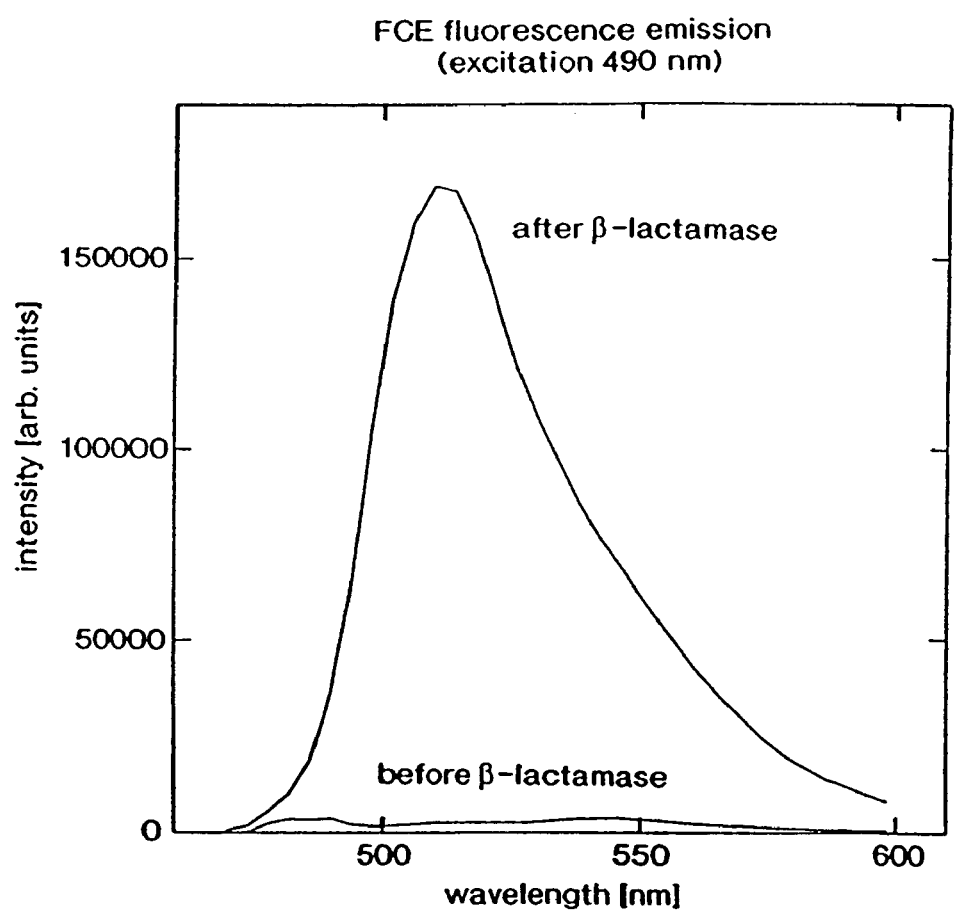
FIG. 2 illustrates the emission spectrum of compound 17 before and after β-lactamase cleavage of the β-lactam ring.

Cleavage of the compound increases fluorescence at 515 nm about 70-fold (FIG. 2). The fluorescence properties of the compound can be attributed to dye-dimer formation, as FRET increases drastically once methanol is added to the solution. Methanol breaks the hydrophobic interaction that causes the fluorophores to stack.

Example 3 compound 22

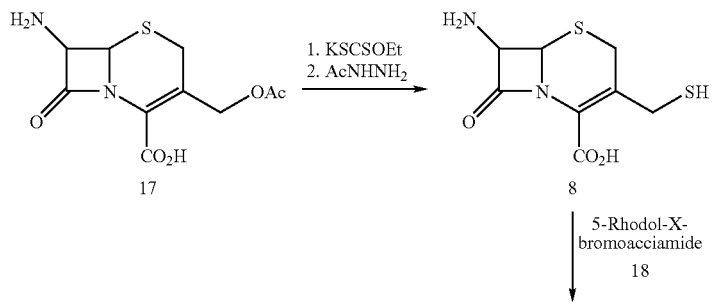

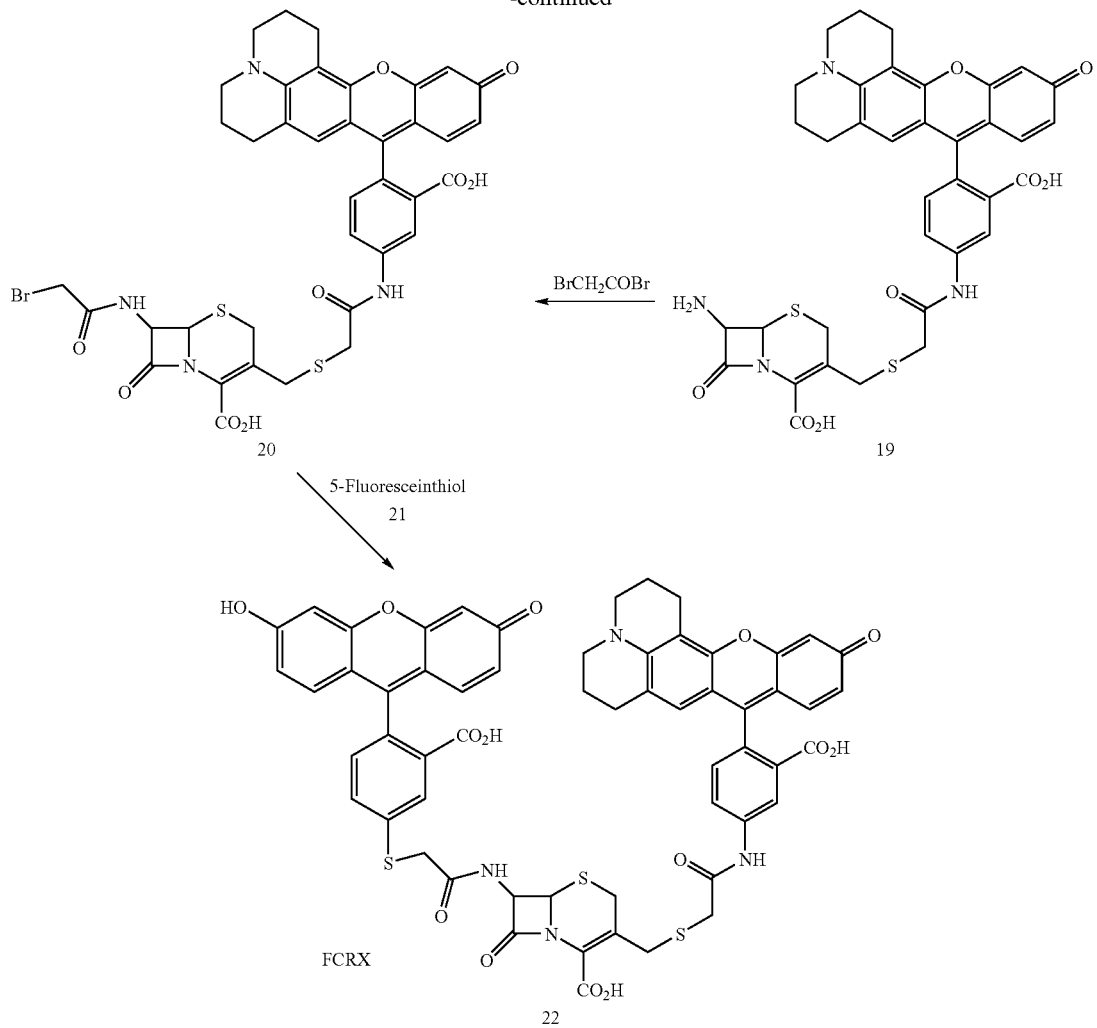

The 3'-acetate of 7-aminocephalosporanic acid was displaced by ethylxanthate [Van Heyningen and Brown (1965), supra] which was hydrolysed to the free sulfhydryl with aqueous acetylhydrazine [Japanese Patent, Kokai 75/18494, CA85 97320d]. The sulfhydryl group was reacted with 5-bromoacetamido-rhodol-X in aqueous dimethylformamide. The cephalosporin 7-amine was reacted with bromoacetyl bromide in aqueous dioxane, followed by bromide displacement with 5-fluoresceinthiol to yield a FRET-cephalosporin that is virtually nonfluorescent in 50 mM phosphate buffer pH 7. This compound is referred to as FCRX.

The first step in preparation of 5-rhodol-X-bromoacetamide was synthesis of 9-(2'-carboxy-4'(5') -nitro-benzoyl)-8-hydroxyjulolidine and separation of the isomers. 10.1 g (48 mmol, 92% purity) 4-Nitrophthalic anhydride were dissolved in 20 ml toluene at 70° C. 9.76 g (50 mmol, 97% purity) 8-Hydroxyjulolidine in 20 ml ethyl acetate were added and the solution kept at 70° C. for 30 min. The reaction mixture was run through a short bed of silica gel followed by ethyl acetate as eluent. The solvents were removed in vacuo and the solid redissolved in a minimum amount of refluxing ethyl acetate. The isomer with the nitro-group meta to the benzoic acid crystallizes over night from solution in orange crystals (3.47 g in first fraction). After additional fractional crystallization the pure isomer was obtained. $^1$H NMR (CDCl$_3$) of crystallized isomer: δ 1.91 ppm (m, 4H, aliphatic methylenes), δ 2.73 ppm, 2.46 ppm (2m, 4H, anilinic methylenes), δ 3.26 ppm (m, 4H, benzylic methylenes), δ 6.32 ppm (s, 1H, julolidine), δ 7.53 ppm (d, 1H, J=8.4 Hz, phthalic), δ 8.43 ppm (dd, J$_1$=8.4 Hz, J$_2$=2.2 Hz, phthalic), δ 8.90 ppm (d, 1H, J=2.2 Hz, phthalic)

For preparation of 5-rhodol-X-amine hydrochloride (named by analogy with rhodamine-X), 1.91 g (5.0 mmol) 9-(2'-Carboxy-4'-nitro-benzoyl)-8-hydroxyjulolidine was stirred in 5 ml concentrated (96%) sulfuric acid. 700 mg (6.4 mmol, 1.25 equ.) resorcinol was added with cooling over a period of 15 minutes. The suspension was stirred 1.5 hours at room temperature and then poured into 200 ml water with vigorous stirring. The purple precipitate was collected by filtration and redissolved in 75 ml water with the help of 5.3 g (22 mmol) sodium sulfide nonahydrate. 2.5 g (44.6 mmol) Anhydrous sodium bisulfide was added and the solution refluxed for 24 hours. Then, after cooling to room temperature, the product was precipitated by addition of glacial acetic acid. The solid was collected by filtration and boiled with 100 ml half-saturated aqueous hydrochloric acid. The solution was filtered hot through a glass frit to remove sulfur. The solution volume was reduced to 10 ml on the rotary evaporator. 1 Volume saturated brine was added and the precipitate collected by filtration. Crystallization from refluxing hydrochloric acid yielded 1.78 g (3.85 mmol, 77%) dark red crystals of 5-rhodol-X-amine hydrochloride. $^1$H NMR (dDMSO) of 5-nitro-rhodol-X: δ 1.90 ppm, 2.05 ppm (2m, 4H, aliphatic methylenes), δ 2.72 ppm, 3.03 ppm (2m, 4H, anilinic methylenes), δ 3.66 ppm (m, 4H, benzylic methylenes), δ 6.90 ppm (s, 1H, xanthene), δ 6.96 ppm (dd, 1H, $J_1$=9.0 Hz, $J_2$=2.1 Hz, xanthene), δ 7.11 ppm (d, 1H, J=9.0 Hz, xanthene), δ 7.22 ppm (d, 1H, J=2.1 Hz, xanthene), δ 7.78 ppm (d, 1H, J=8.4 Hz, phthalic), δ 8.70 ppm (dd, 1H, $J_1$=8.4 Hz, $J_2$=2.4 Hz, phthalic), δ 8.91 ppm (d, 1H, J=2.4 Hz, phthalic). $^1$H NMR (CD$_3$OD) of 5-rhodol-X-amine hydrochloride: δ 2.00 ppm, 2.14 ppm (2m, 4H, aliphatic methylenes), δ 2.75 ppm, 3.11 ppm (2m, 4H, anilinic methylenes), δ 3.67 ppm (m, 4H, benzylic methylenes), δ 6.85 ppm (s, 1H, xanthene), δ 6.94 ppm (dd, 1H, $J_1$=9.0 Hz, $J_2$=2.1 Hz, xanthene), δ 7.13 ppm (d, 1H, J=9.0 Hz, xanthene), δ 7.16 ppm (d, 1H, J=2.1 Hz, xanthene), δ 7.55 ppm (d, 1H, J=8.1 Hz, phthalic), δ 7.82 ppm (dd, 1H, $J_1$ 8.1 Hz, $J_2$=1.9 Hz, phthalic), δ 8.28 ppm (d, 1H, J=1.9 Hz, phthalic).

Preparation of 5-rhodol-X-bromoacetamide (18) was effected as follows. 115 mg (0.25 mmol) 5-Rhodol-X-amine hydrochloride were dissolved with 180 mg (2.1 mmol) sodium bicarbonate in 2ml water-dioxane (1:1). The solution was cooled on ice and 175 µl (2 mmol) bromoacetylbromide were added with stirring over a period of 20 minutes. The solution was then kept at room temperature for 1.5 hours, after which 5 volumes of water were added. The dioxane was removed on the rotary evaporator, and the product was precipitated from the remaining aqueous solution by addition of acetic acid. The precipitate was filtered off and dissolved in a small volume of chloroform-methanol (1:1). Silica gel was added to the solution and the solvents removed in vacuo. The solids were applied to a silica gel column and the product eluted with methanol-ethyl acetate (1:4). This eluent did dissolve some silica gel which remained with the eluted product. $^1$H NMR (CD$_3$OD, 10% dDMSO): δ 1.98 ppm, 2.12 ppm (2 m, 4H, aliphatic methylenes), δ 2.72 ppm, 3.06 ppm (2 m, 4H, anilinic methylenes), δ 3.56 ppm (m, 4H, benzylic methylenes), δ 4.08 ppm (s, 2H, bromoacetyl), δ 6.79 ppm (dd, 1H, $J_1$=9.2 Hz, $J_2$=2.1 Hz, xanthene), δ 6.83 ppm (s, 1H, xanthene), δ 6.9 ppm (d, 1H, J=2.1 Hz, xanthene), δ 7.19 ppm (d, 1H, J=9.2 Hz, xanthene), δ 7.24 ppm (d, 1H, J=8.4 Hz, phthalic), δ 8.02 ppm (dd, 1H, $J_1$=8.4 Hz, $J_2$≈1 Hz, phthalic), δ 8.30 ppm (d, 1H, J≈1 Hz, phthalic).

For preparation of 7β-(bromoacetamido)-3-[[[(5-rhodol-X-amido)methyl]thio]methyl]-3-cephem-4-carboxylic acid (20), 4.5 mg (10 µmol) 5-Rhodol-X-bromoacetamide (18) were dissolved in 0.5 ml 250 mM phosphate buffer adjusted to pH 7.7 and 0.5 ml dimethylformamide. The solution was deoxygenated and 10 mg (40 µmol) 7β-amino -3-(thiomethyl)-3-cephem-4-carboxylic acid (8) prepared according to the literature procedure in 100 µl phosphate buffer was added in an argon atmosphere. The solution was kept for 2 hours at 30° C. Then the solvents were removed in vacuo and the residue dissolved in 1 ml water, from which the product was precipitated by addition of acetic acid. The precipitate was collected and the product purified by C$_{18}$ reverse-phase chromatography with 0.1% trifluoroacetic acid in 35% methanol/water as eluent.

The above product (19) was dissolved in 1 ml dioxane-water (1:1) with 20 mg sodium bicarbonate. 10 µl Bromoacetyl bromide were added to the solution on ice. The solution was kept for another 1.5 hours at room temperature. 20 mg sodium bicarbonate and 10 µl bromoacetyl bromide were added to the solution with ice cooling. After another 1.5 hours at room temperature the dioxane was removed on the rotary evaporator and the products were precipitated from the aqueous solution with 1M phosphoric acid and collected by centrifugation. The solids were suspended in dilute aqueous bicarbonate solution and the undissolved particles removed by centrifugation and discarded. The product was precipitated with 1M phosphoric acid and purified by flash chromatography on silica gel with chloroform-methanol-acetic acid-water (55:15:4:2). This procedure dissolved small amounts of silica gel.

Coupling of diacetyl 5-fluoresceinthiol (21) with 7β-(bromoacetamido)-3-[[[(5-rhodol-X-amido)methyl]thio]methyl]-3-cephem-4-carboxylic acid (20) was effected as follows. 7β-(Bromoacetamido)-3-[[[(5-rhodol-X -amido)methyl]thio]methyl]-3-cephem-4-carboxylic acid was reacted with a 50% excess of 5-fluoresceinthiol under argon with dimethylformamide-(250 mM aqueous phosphate buffer pH 7.7) (1:1) as the solvent. The product was purified from excess fluoresceinthiol by repeated dissolution in methanol and precipitation in ethyl acetate.

Figure 3:
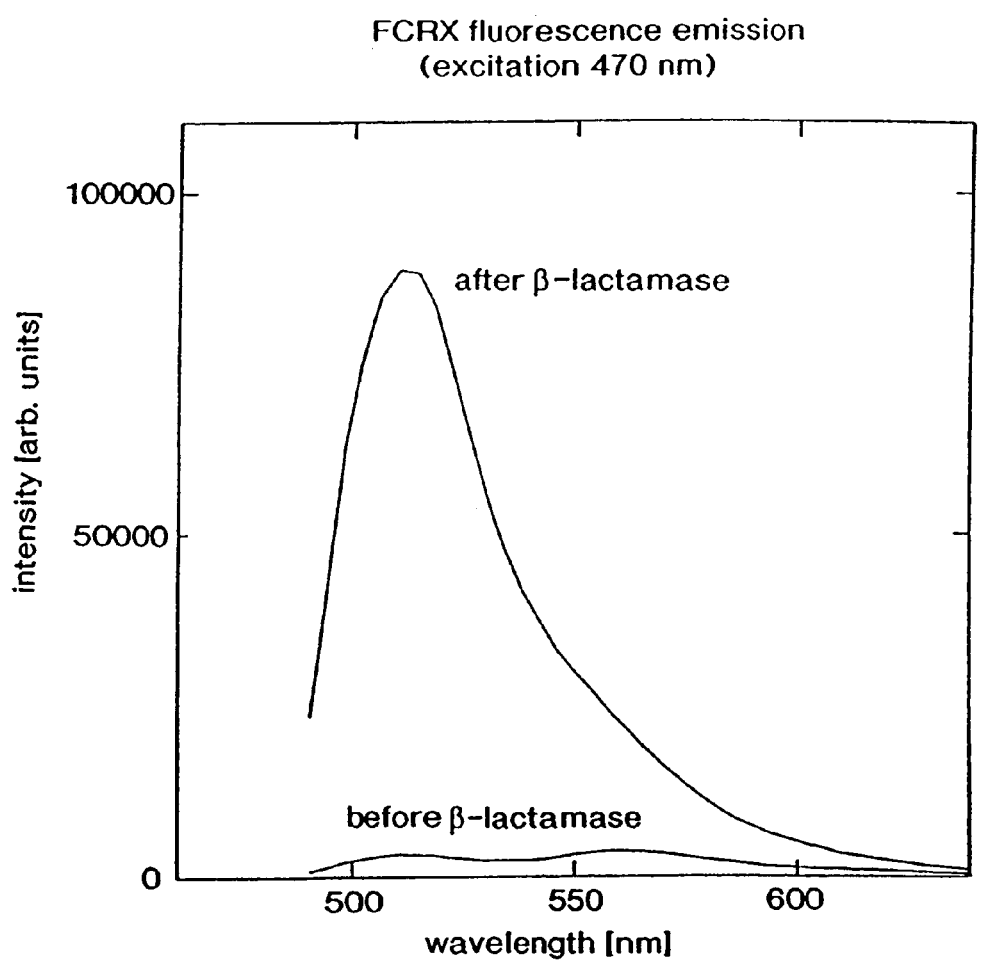
FIG. 3 illustrates the emission spectrum of compound 22 before and after β-lactamase cleavage of the β-lactam ring.

FIG. 3 shows the fluorescence emission spectra of this FRET-cephalosporin in 50 mM phosphate buffer pH 7 before and after treatment with β-lactamase. The low initial fluorescence is due to the stacking of the fluorophores, forming a ground state complex that is nonfluorescent. When one adds methanol to the solution this stacking can be disrupted and efficient fluorescence resonance energy transfer occurs.

Example 4 compound 25

N-[resorufin-4-carbonyl]-N'-iodoacetyl-piperazine (Boehringer Mannheim) was attached to the cephalosporin as a FRET-acceptor for fluorescein. It is referred to as FCRE.

The FRET-cephalosporin FCRE (25) carrying fluorescein as the donor and resorufin as the quencher was made by the same procedure as the one carrying the rhodol-X-acceptor. The N-[resorufin-4-carbonyl]-N'-iodoacetyl-piperazine (Boehringer Mannheim) was coupled to the free 3'-thiol of the cephalosporin followed by bromoacetylation and addition of the 5-fluoresceinthiol. In departure from the protocol, three equivalents of 5-fluorescein thiol were added, as the first equivalent instantaneously reduced the resorufin and formed unreactive difluorescein-disulfide. Exposure to air reoxidized resorufin to the original dye.

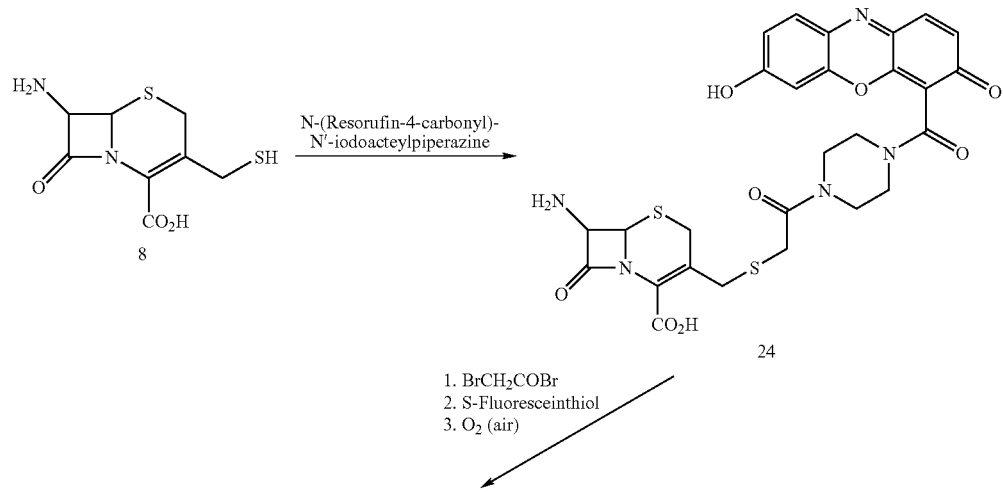

Figure 4:
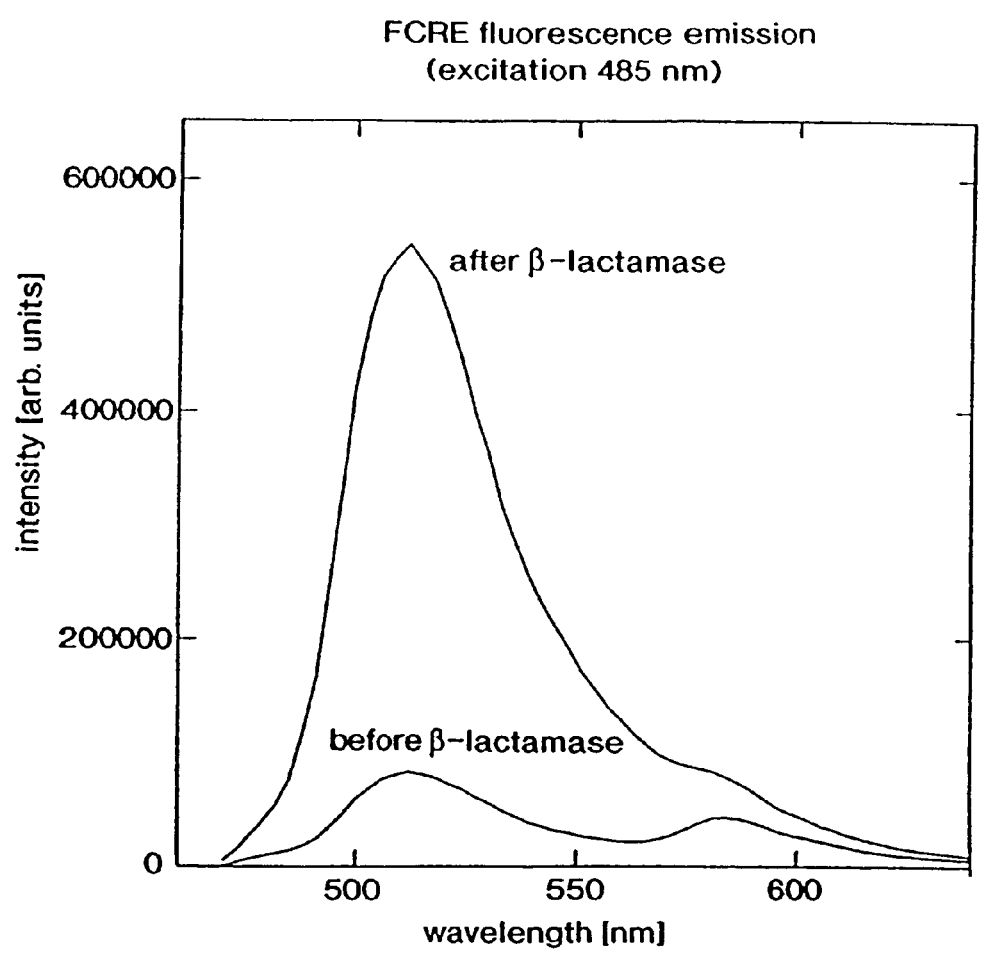
FIG. 4 illustrates the emission spectrum of compound 25 before and after β-lactamase cleavage of the β-lactam ring.

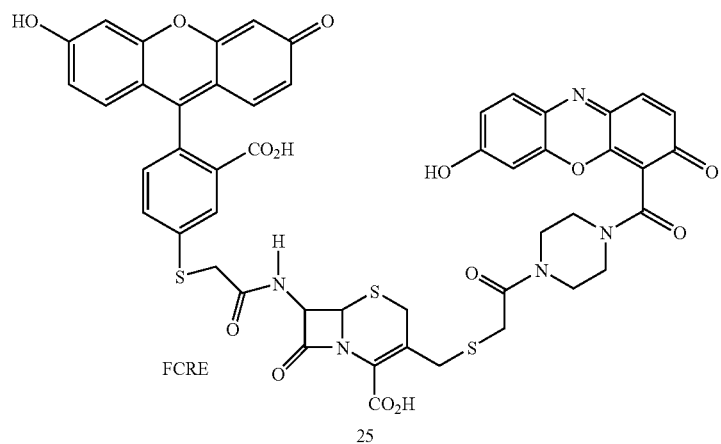

β-Lactamase catalyzed hydrolysis of this compound generates two fluorescent fragments. Resorufin excitation and emission spectra are longer wavelength and narrower than the rhodol spectra, possibly affording better spectral separation between the uncleaved dye versus the products of enzymatic cleavage. But, as in the case of rhodol as the acceptor, in aqueous phosphate buffer the dyes stack and form a dark complex. β-Lactamase treatment disrupts the stacking and increases donor fluorescence (FIG. 4).

Example 5
compound 7b
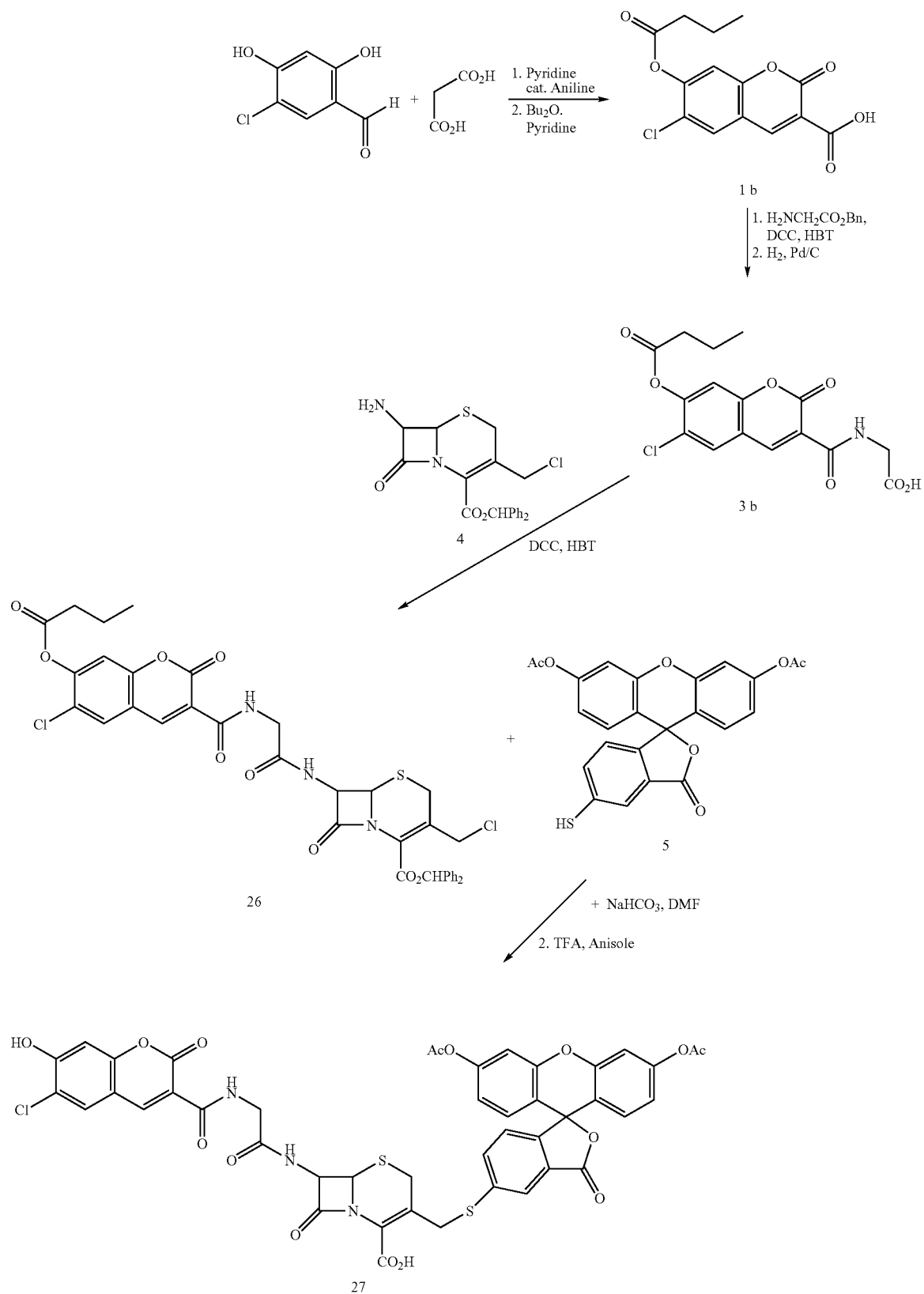

For synthesis of 2,4 dihydroxy-5-chlorobenzaldehyde, 21.7 g (0.15 Mol) 4-chlororesorcinol were dissolved in 150 ml dry diethyl ether and 27 g finely powdered zinc (II) cyanide and 0.5 g potassium chloride were added with stirring. The suspension was cooled on ice. A strong stream of hydrogen chloride gas was blown into the solution with vigorous stirring. After approximately 30 minutes the reactants were dissolved. The addition of hydrogen chloride gas was continued until it stopped being absorbed in the ether solution (approx. 1 hour). During this time a precipitate formed. The suspension was stirred for one additional hour on ice. Then the solid was let to settle. The ethereal solution was poured from the solid. The solid was treated with 100 g of ice and heated to 100° C. in a water bath. Upon cooling the product crystallized in shiny plates from the solution. They were removed by filtration on dried over potassium hydroxide. The yield was 15.9 g (0.092 Mol, 61%). $^1$H NMR (CDCl$_3$): δ 6.23 ppm (s, 1H, phenol), δ 6.62 ppm (s, 1H, phenyl), δ 7.52 ppm (s, 1H, phenyl), δ 9.69 ppm (s, 1H, formyl), δ 11.25 ppm (s, 1H, phenol).

To prepare 3-carboxy 6-chloro 7-hydroxy coumarin, 5.76 g (0.033 Mol) 2,4-dihydroxy-5-chlorobenzaldehyde and 7.2 g (0.069 Mol) malonic acid were dissolved in 5 ml warm pyridine. 75 µl Aniline were stirred into the solution and the reaction let to stand at room temperature for 3 days. The yellow solid that formed was broken into smaller pieces and 50 ml ethanol was added. The creamy suspension was filtered through a glass frit and the solid was washed three times with 1 N hydrochloric acid and then with water. Then the solid was stirred with 100 ml ethyl acetate, 150 ml ethanol and 10 ml half concentrated hydrochloric acid. The solvent volume was reduced in vacuo and the precipitate recovered by filtration, washed with diethyl ether and dried over phosphorous pentoxide. 4.97 g (0.021 Mol, 63%) of product was obtained as a white powder. $^1$H NMR (dDMSO): δ 6.95 ppm (s, 1H), δ 8.02 ppm (s, 1H), δ 8.67 ppm (s, 1H).

To prepare 7-butyryloxy-3-carboxy-6-chlorocoumarin, 3.1 g (12.9 mMol) 3-carboxy-6-chloro-7-hydroxycoumarin were dissolved in 100 ml dioxane and treated with 5 ml butyric anhydride, 8 ml pyridine and 20 mg dimethyl aminopyridine at room temperature for two hours. The reaction solution was added with stirring to 300 ml heptane upon which a white precipitate formed. It was recovered by filtration and dissolved in 150 ml ethyl acetate. Undissolved material was removed by filtration and the filtrate extracted twice with 50 ml 1 N hydrochloric acid/brine (1:1) and then brine. The solution was dried over anhydrous sodium sulfate. Evaporation in vacuo yielded 2.63 g (8.47 mMol, 66 k) of product. 1H NMR (CDCl$_3$): δ 1.08 ppm (t, 3H, J=7.4 Hz, butyric methyl), δ 1.85 ppm (m, 2H, $J_1 \approx J_2$ =7.4 Hz, butyric methylene), δ 2.68 ppm (t, 2H, J=7.4 Hz, butyric methylene), δ 7.37 ppm (s, 1H, coumarin), δ 7.84 ppm (s, 1H, coumarin), δ 8.86 ppm (s, 1H, coumarin).

Preparation of 7-butyryloxy-3-benzyloxycarbonylmethylaminocarbonyl-6-chlorocoumarin is effected as follows. 2.5 g (8.06 mMol) 7-Butyryloxy-3-carboxy-6-chlorocoumarin, 2.36 g hydroxybenztriazole hydrate (16 mmol) and 1.67 g (8.1 mMol) dicyclohexyl carbodiimide were dissolved in 30 ml dioxane. A toluene solution of O-benzylglycine [prepared by extraction of 3.4 g (10 mMol) benzylglycine tosyl salt with ethyl acetate-toluene-saturated aqueous bicarbonate-water (1:1:1:1, 250 ml), drying of the organic phase with anhydrous sodium sulfate and reduction of the solvent volume to 5 ml] was added dropwise to the coumarin solution. The reaction was kept at room temperature for 20 hours after which the precipitate was removed by filtration and washed extensively with ethylacetate and acetone. The combined solvent fractions were reduced to 50 ml on the rotatory evaporator upon which one volume of toluene was added and the volume further reduced to 30 ml. The precipitating product was recovered by filtration and dissolved in 200 ml chloroform-absolute ethanol (1:1). The solution was reduced to 50 ml on the rotatory evaporator and the product filtered off and dried in vacuo yielding 1.29 g of the title product. Further reduction of the solvent volume yielded a second crop (0.64 g). Total yield: 1.93 g (4.22 mMol, 52%). $^1$H NMR (CDCl$_3$): δ 1.08 ppm (t, 3H, J=7.4 Hz, butyric methyl), δ 1.84 ppm (m, 2H, $J_1 \approx J_2$=7.4 Hz, butyric methylene), δ 2.66 ppm (t, 2H, J=7.4 Hz, butyric methylene), δ 4.29 ppm (d, 2H, J=5.5 Hz, glycine methylene), δ 5.24 ppm (s, 2H, benzyl), δ 7.36 ppm (s, 1H, coumarin), δ 7.38 ppm (s, 5H, phenyl), δ 7.77 ppm (s, 1H, coumarin), δ 8.83 ppm (s, 1H, coumarin), δ 9.15 ppm (t, 1H, J=5.5 Hz, amide).

7-Butyryloxy-3-carboxymethylaminocarbonyl-6-chlorocoumarin was prepared as follows. 920 mg (2 mMol) 7-butyryloxy-3-benzyloxycarbonylmethylaminocarbonyl-6-chlorocoumarin were dissolved in 50 ml dioxane. 100 mg palladium on carbon (10%) and 100 µl acetic acid were added to the solution and the suspension stirred vigorously in a hydrogen atmosphere at ambient pressure. After the uptake of hydrogen seized the suspension was filtered. The product containing carbon was extracted five times with 25 ml boiling dioxane. The combined dioxane solutions were let to cool upon which the product precipitated as a white powder. Reduction of the solvent to 20 ml precipitates more product. The remaining dioxane solution is heated to boiling and heptane is added until the solution becomes cloudy. The weights of the dried powders were 245 mg, 389 mg and 58 mg, totaling 692 mg (1. 88 mMol, 94%) of white product. $^1$H NMR (dDMSO): δ 1.02 ppm (t, 3H, J=7.4 Hz, butyric methyl), δ 1.73 ppm (m, 2H, $J_1 \approx J_2$=7.3 Hz, butyric methylene), δ 2.70 ppm (t, 2H, J=7.2 Hz, butyric methylene), δ 4.07 ppm (d, 2H, J=5.6 Hz, glycine methylene), δ 7.67 ppm (s, 1H, coumarin), δ 8.35 ppm (s, 1H, coumarin), δ 8.90 ppm (s, 1H, coumarin), δ 9.00 ppm (t, 1H, J=5.6 Hz, amide).

Coupling of 7-Butyryloxy-3-carboxymethylaminocarbonyl-6-chlorocoumarin with 7-amino-3'-chlorocephalosporanic acid benzhydryl ester was effected as follows. 368 mg (1 mMol) 7-Butyryloxy-3-carboxymethylaminocarbonyl-6-chlorocoumarin, 270 mg hydroxybenztriazole hydrate and 415 mg (1 mMol) 7-amino-3'-chloro cephalosporanic acid benzhydryl ester were suspended in 40 ml dioxane-acetonitrile (1:1). 260 mg (1.25 mMol) dicyclohexylcarbodiimide in 5 ml acetonitrile were added and the suspension was stirred vigorously for 36 hours. The precipitate was removed by filtration and the volume of the solution reduced to 20 ml on the rotatory evaporator. 50 ml Toluene was added and the volume reduced to 30 ml. With stirring 50 ml heptane was added and the suspension chilled on ice. The precipitate was recovered by filtration. It was redissolved in 10 ml chloroform and the remaining undissolved solids were filtered off. Addition of 2 volumes of heptane precipitated the title product which was collected and dried in vacuo and yielded 468 mg (0.64 mMol, 64%) off-white powder. $^1$H NMR (CDCl$_3$): δ 1.08 ppm (t, 3H, J=7.4 Hz, butyric methyl), δ 1.84 ppm (m, 2H, J$_1$≈J$_2$=7.4 Hz, butyric methylene), δ 2.66 ppm (t, 2H, J=7.4 Hz, butyric methylene), δ 3.54 ppm (2d, 2H, J=18.3 Hz, cephalosporin C-2), δ 4.24 ppm (2d, 2H, J=5.8 Hz, cephalosporin 3 methylene), δ 4.37 ppm (d, 2H, J=3.8 Hz, glycine methylene), δ 5.02 ppm (d, 1H, J=4.9 Hz, cephalosporin C-6), δ 5.89 ppm (dd, 1H, J$_1$=9.0 Hz, J$_2$ =5.0 Hz, cephalosporin C-7), δ 6.96 ppm (s, 1H, benzhydryl), δ 7.30 -7.45 ppm (m, 12H, phenyl, coumarin, amide), δ 7.79 ppm (s, 1H, coumarin), δ 8.84 ppm (s, 1H, coumarin), δ 9.28 ppm (t, 1H, J=3.7 Hz, amide).

Coupling of the above product with 5-fluoresceinthiol was effected as follows. 90 mg (0.2 mmol) 5-mercaptofluorescein diacetate disulfide dimer were dissolved in 10 ml chloroform and treated with 25 μl tributyl phosphine and 25 μl water in an argon atmosphere. The solution was kept for 2 hours at ambient temperature and was then added to a solution of 20 mg sodium bicarbonate, 25 mg sodium iodide and 110 mg (0.15 mMol) of the above compound in 10 ml is dimethylformamide. After 4 hours the solvents were removed in vacuo and the residue triturated with diethylether. The solid was dissolved in ethyl acetate-acetonitrile (1:1). After removal of the solvents the residue was triturated once more with diethylether yielding 157 mg (0.13 mMol, 88%) of a cream colored powder product.

A sample of the above compound was treated with a large access of trifluoroacetic acid-anisole (1:1) at room temperature for 20 minutes. The reagents are removed in vacuo and the residue triturated with ether. High performance liquid chromatography of the solid in 45% aqueous acetonitrile containing 0.5% acetic acid gives a product in which the butyrate and the diphenylmethyl esters have been cleaved. It was purified by high performance liquid chromatography on a reverse phase C$_{18}$-column using 45% aqueous acetonitrile containing 5% acetic acid as the eluent.

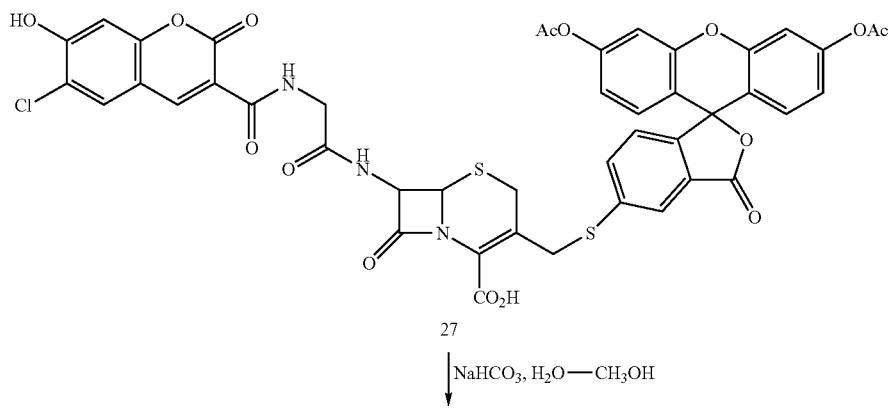

27

NaHCO$_3$, H$_2$O — CH$_3$OH

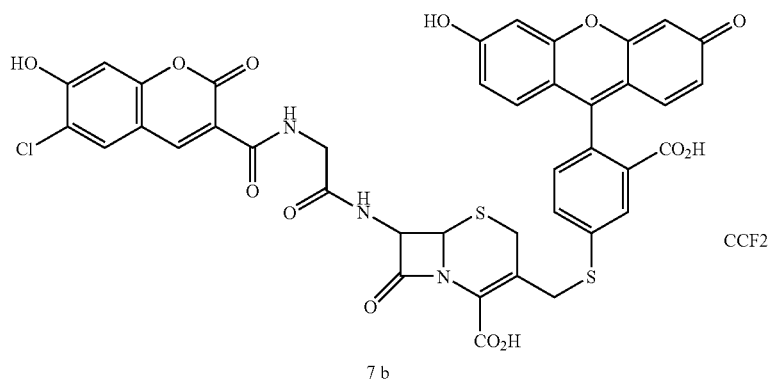

CCF2

7 b

Deprotection of the fluorescein acetates in compound 27 was accomplished with sodium bicarbonate in methanol (room temperature, 30 minutes) to provide the fluorescent enzyme substrate CCF2. It was purified by high performance liquid chromatography on a reverse phase $C_{18}$-column using 35% aqueous acetonitrile containing 0.5% acetic acid as the eluent.

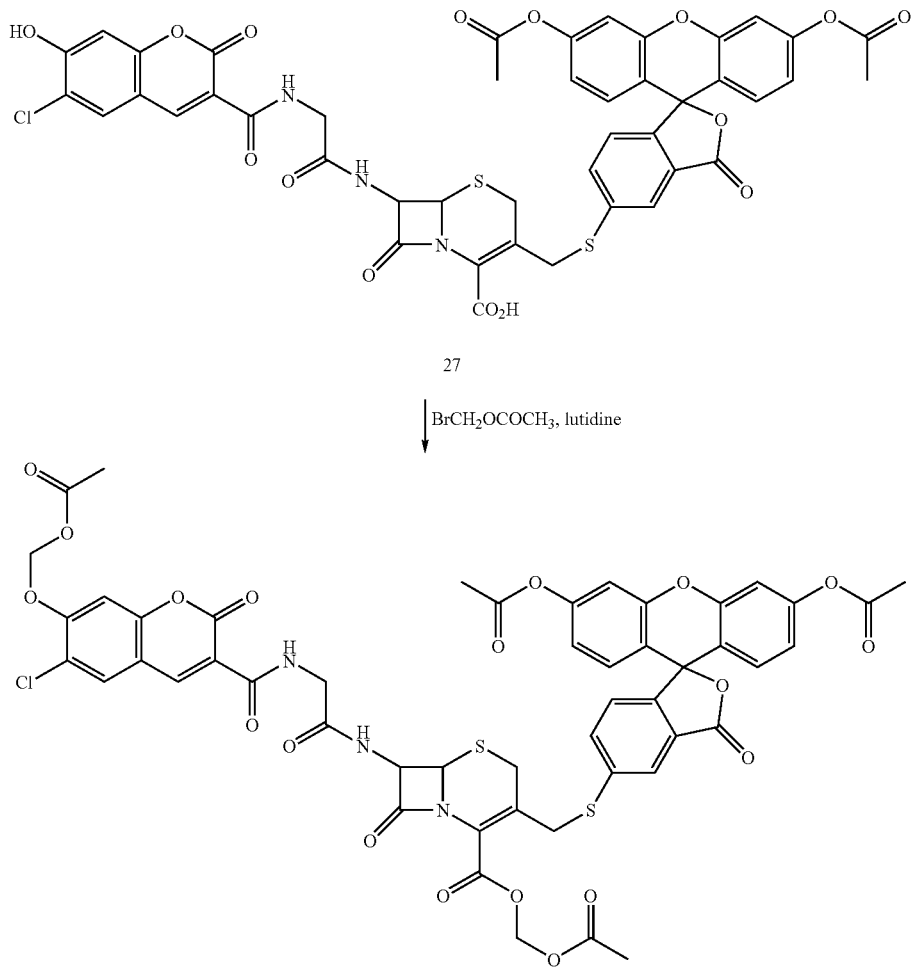

Stirring of compound 27 with excess acetoxymethyl bromide in dry lutidine produced the membrane permeable derivative of the substrate (CCF2/$ac_2AM_2$). It was purified by high performance liquid chromatography on a reverse phase $C_{18}$-column using 65% aqueous acetonitrile containing 0.5% acetic acid as the eluent. CCF2/$ac_2AM_2$ is readily converted to CCF2 in the cells' cytoplasm.

Unlike in Examples 1-4, the donor and acceptor dyes in substrate CCF2 do not stack. The substrate is fully fluorescent in phosphate buffer and there is no formation of the "dark complex" (i. e., addition of methanol does not change the fluorescence spectrum of CCF2, except for the effect of dilution). This is due to the much smaller and more polar nature of the 7-hydroxycoumarin compared to that of the xanthene dyes (eosin, rhodamine, rhodol and resorufin) in Examples 1-4.

Figure 5:
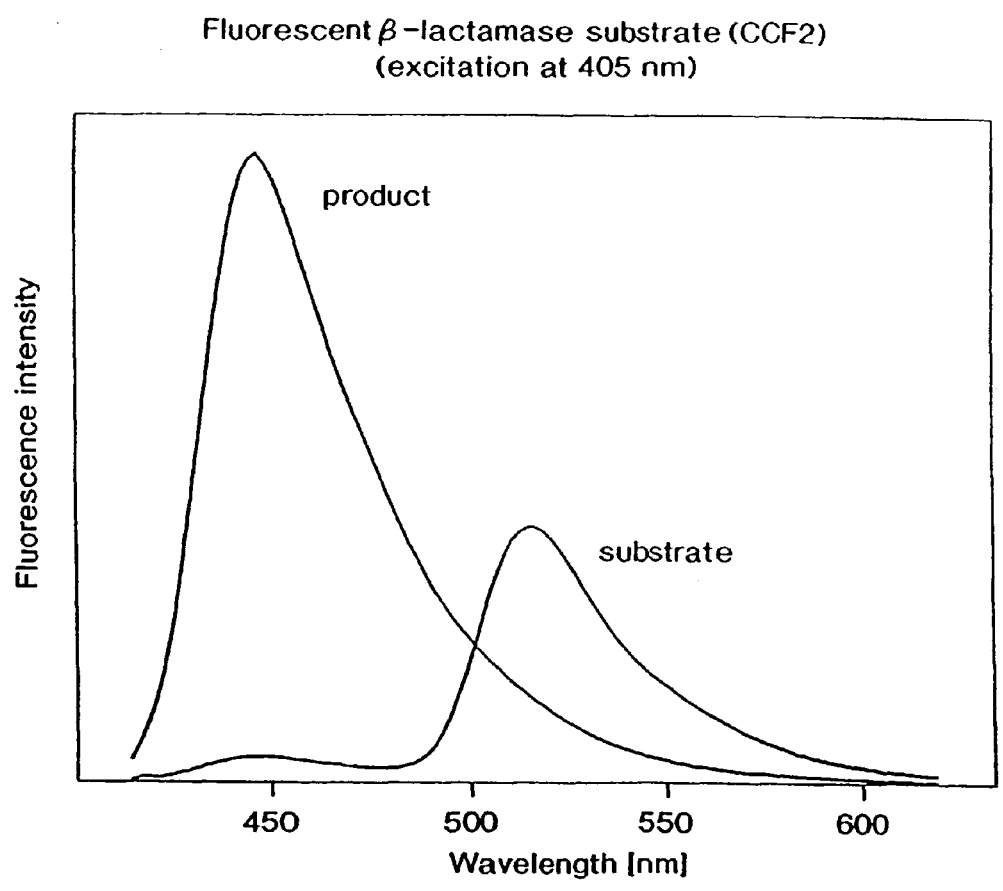
FIG. 5 illustrates the emission spectrum of compound CCF2 before and after β-lactamase cleavage of the β-lactam ring.

FIG. 5 illustrates the emission spectrum of compound CCF2 in 50 mmolar phosphate buffer pH 7. 0 before and after β-lactamase cleavage of the β-lactam ring. In the intact substrate, efficient energy transfer occurs from the 7-hydroxycoumarin moiety to the fluorescein moiety. Excitation of the substrate at 405 nm results in fluorescence emission at 515 nm (green) from the acceptor dye fluorescein. The energy transfer is disrupted when β-lactamase cleaves the β-lactam ring, thereby severing the link between the two dyes. Excitation of the products at 405 nm now results entirely in donor fluorescence emission at 448 nm (blue). The fluorescence emission from the donor moiety increases 25 fold upon β-lactam cleavage. The fluorescence at 515 nm is reduced by 3.5 fold, all of the remaining fluorescence originating from the 7-hydroxycoumarin as its emission spectrum extends into the green. Twenty-five-fold quenching of the donor in the substrate is equivalent to an efficiency of fluorescence energy transfer of 96%. This large fluorescence change upon β-lactam cleavage can readily be used to detect β-lactamase in the cytoplasm of living mammalian cells, as is reported in Examples 6 and 7.

The 7-hydroxycoumarin moiety in the cephalosporin was determined to have a fluorescence quantum efficiency in the absence of the acceptor of 98-100%. This value was determined by comparing the integral of the corrected fluorescence emission spectrum of the dye with that of a solution of 9-aminoacridine hydrochloride in water matched for absorbance at the excitation wavelength. It follows that 7-hydroxycoumarin is an ideal donor dye, as virtually every photon absorbed by the dye undergoes fluorescence energy transfer to the acceptor.

Example 6

Cells of the T-cell lymphoma line Jurkat were suspended in an isotonic saline solution (Hank's balanced salt solution) containing approximately $10^{12}$ β-lactamase enzyme molecules per milliliter (approximately 1.7 nM; Penicillinase 205 TEM R$^+$, from Sigma) and 1 mg/ml rhodamine conjugated to dextran (40 kd) as a marker of loading. The suspension was passed through a syringe needle (30 gauge) four times. This causes transient, survivable disruptions of the cells' plasma membrane and allows entry of labeled dextran and β-lactamase. Cells that had been successfully permeabilized contained β-lactamase and were red fluorescent when illuminated at the rhodamine excitation wavelength on a fluorescent microscope. The cells were incubated with 5 μM fluorogenic β-lactamase substrate, CCF2/ac$_2$AM$_2$, at room temperature for 30 minutes. Illumination with violet light (405 nm) revealed blue fluorescent and green fluorescent cells. All cells that had taken up the marker rhodamine-dextran appeared fluorescent blue, while cells devoid the enzyme appeared fluorescent green.

Example 7

Cells from cell lines of various mammalian origin were transiently transfected with a plasmid containing the RTEM β-lactamase gene under the control of a mammalian promotor. The gene encodes cytosolic β-lactamase lacking any signal sequence and is listed as SEQ. ID. 1. 10 to 48 hours after transfection cells were exposed to 5 μmol CCF2/ac$_2$AM$_2$ for 1 to 6 hours. In all cases fluorescent blue cells were detected on examination with a fluorescence microscope. Not a single blue fluorescent cell was ever detected in nontransfected control cells. To quantitate the fluorescence measurements the cells were first viewed through coumarin (450 DF 65) and then fluorescein (515 EFLP) emission filters and pictures were recorded with a charge couple device camera. The average pixel intensities of CCF2 loaded transfected cells (blue) and controls (green) at coumarin-and fluorescein wavelength in COS-7 (Table 2) and CHO (Table 3) cells are summarized; values for 4 representative cells for each population are given. Thus, the substrate CCF2 revealed gene expression in single living mammalian cells.

TABLE 2

| COS-7 (origin: SV40 transformed african green monkey kidney cells) | | |
|---|---|---|
| Table of pixel intensities | coumarin emission filter | fluorescein emission filter |
| Blue cell #1 | 27 | 20 |
| #2 | 34 | 23 |
| #3 | 31 | 31 |
| #4 | 22 | 33 |
| Green cell #1 | 4 | 43 |
| #2 | 4 | 42 |
| #3 | 5 | 20 |
| #4 | 3 | 24 |

TABLE 3

| CHO (origin: Chinese hamster ovary cells) | | |
|---|---|---|
| Table of pixel intensities | coumarin emission filter | fluorescein emission filter |
| Blue cell #1 | 98 | 112 |
| #2 | 70 | 113 |
| #3 | 76 | 92 |
| #4 | 56 | 67 |
| Green cell #1 | 9 | 180 |
| #2 | 9 | 102 |
| #3 | 7 | 101 |
| #4 | 9 | 83 |

Example 8

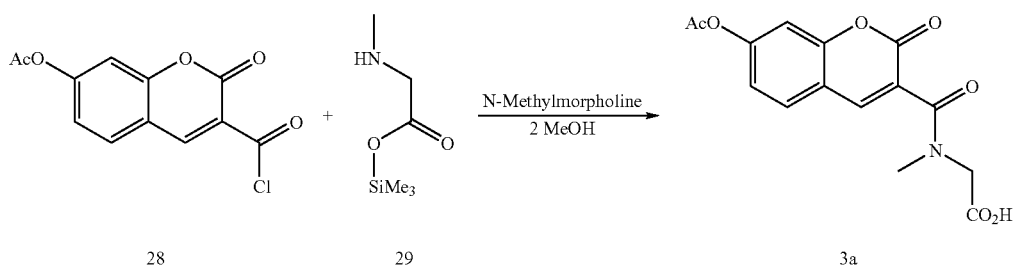

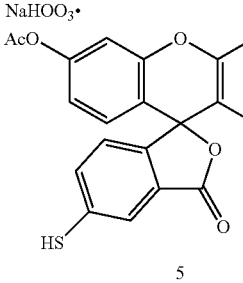

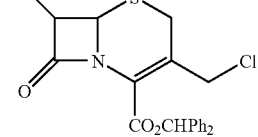

-continued

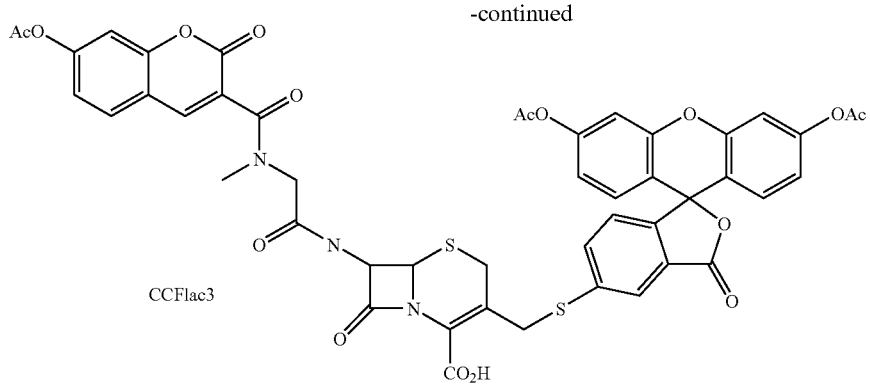

CCFlac3

| orange peel acetyl esterase
| aqueous phosphate buffer pH 7

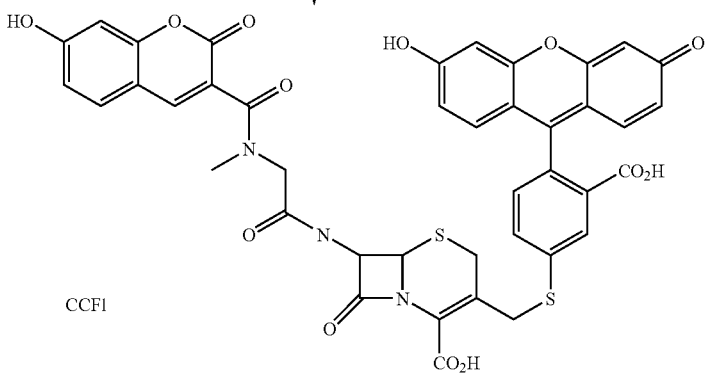

CCFl

7a

For preparation of 7-acetyloxy-3-(N-carboxymethyl-N-methylaminocarbonyl)coumarin, 400 mg (1.6 mMol) 3-carboxy-7-acetylcoumarin were refluxed with 4 ml thionyl chloride for 20 minutes. Excess thionyl chloride was removed by distillation and the residue (7-acetyloxy-3-chlorocarbonyl-coumarin) stored in vacuo over potassium hydroxide pellets overnight. In a separate vessel 142.5 mg (1.6 mMol) sarcosine was dissolved in 1.05 ml (5.4 mMol) N-methyl trimethylsilyl trifluoroacetamide (MSTFA) and kept at room temperature for 16 hours. 2 ml dry acetonitrile and 187 µl (1.7 mMol) N-methylmorpholine were added and the solution was poured onto the solid 7-acetyloxy-3-chlorocarbonylcoumarin on ice. After stirring for 20 minutes on ice the solution was let to warm to room temperature. After 4 hours the solvents were removed in vacuo. The residue was dissolved in methanol to deprotect the acid after which the solvent was removed in vacuo. The solid was dissolved in 30 ml ethylacetate-acetonitrile (2:1) and the solution extracted twice with an equal volume of 1N hydrochloric acid and the with brine. The organic phase was dried over anhydrous sodium sulfate. The solvent was removed in vacuo and the solid crystallized from boiling ethylacetate with addition of hexane. The yield was 316 mg (1.0 mMol, 63%) of a white crystalline solid.

Coupling of 7-acetyloxy-3-(N-carboxymethyl-N-methylaminocarbonyl)coumarin with 7-amino-3'-chlorocephalosporanic acid benzhydryl ester was effected as follows. 62 mg (0.2 mMol) 7-acetyloxy-3-(N-carboxymethyl-N-methylaminocarbonyl)coumarin was stirred with 1 ml dry methylene chloride to which 27 mg (0.2 mmol) hydroxybenztriazole and 41 mg dicyclohexyl carbodiimide had been added. A solution of 82.6 mg (0.2 mMol) 7-amino 3'-chloro cephalosporanic acid benzhydryl ester in 1 ml methylene chloride was added dropwise over a period of 5 minutes. The reaction was stirred for 20 hours at room temperature after which the precipitate was removed by filtration. The filtrate was evaporated in vacuo and the product extracted into methylene chloride. The solvent was removed once more and the residue dissolved in 1 ml ethyl acetate. Addition of three volumes of hexane precipitated the product which was recovered by centrifugation. The yield was 49.9 mg (70 µMol, 35%) of the product as a white powder.

Conversion of the cephalosporin 3'-chloro substituent in the above product to the 3'-iodo substituent was carried out as follows. 49.9 mg (70 µMol) of the above product was stirred with 52.5 mg sodium iodide (5 equivalents) in 1.2 ml dry methyl ethyl ketone at room temperature for 2 hours. The solvent was removed in vacuo and the residue dissolved in 2 ml ethyl acetate-methylene chloride (1:1) and extracted with cold 2% aqueous sodium thiosulfate solution, followed by two extractions with brine. The organic layer was dried over anhydrous sodium sulfate. The slightly orange powder (32 mg, 40 µMol, 57%) was used without further purification in the next reaction.

Coupling of above product with 5-mercaptofluorescein diacetate (product CCFlac$_3$ diphenylmethyl ester) was effected by dissolving 32 mg (40 µMol) of the iodo derivative in 0.4 ml dimethylformamide and 3.4 mg sodium bicarbonate added. 22 mg (50 μMol) 5-mercaptofluorescein diacetate were dissolved in 0.3 ml deoxygenated dimethyl formamide and added to the iodo compound in an argon atmosphere. After 2 hours the solvent was removed in vacuo. The residue was suspended in methylene chloride-ethyl acetate (1:1). The organic solution was washed with water and dried over anhydrous sodium sulfate. The solvent was removed and the residue was triturated with ethyl ether hexane (1:1). Flash chromatography on 60 mesh silica gel with ethyl acetate-toluene (2:1) yielded 4.2 mg (4 μMol, 10%) of colorless product.

Cleavage of the diphenylmethyl ester to give CCF1ac₃ was effected as follows. 4 mg (4 μMol) of CCF1ac₃ diphenylmethyl ester were treated with 200 μl trifluoroacetic acid-anisole-methylene chloride (10:1:10) on ice for 15 minutes. The reagents were removed in vacuo and the residue was dissolved in 0.5 ml ethyl acetate and the solvent evaporated in vacuo. The solid was triturated with ether and then dissolved in 0.5 ml methanol. Addition of the methanolic solution to 2 ml water precipitated the product. The product was recovered by centrifugation and dried in vacuo. The yield was 2 mg (2 μMol, 50%) white solid. The compound was further purified by high performance liquid chromatography on a reverse phase C₁₈-column using 55% aqueous acetonitrile containing 0.5% acetic acid as the eluent.

Figure 6:
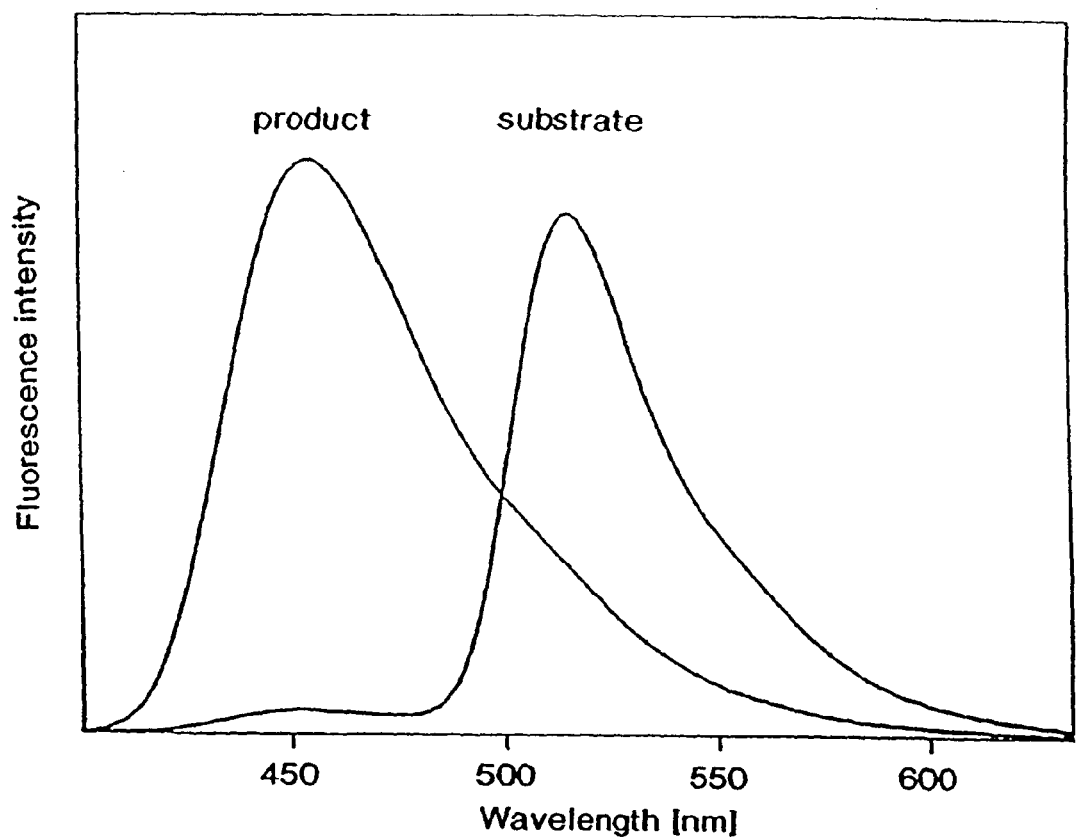
FIG. 6 illustrates the emission spectrum of compound CCF1 before and after β-lactamase cleavage of the β-lactam ring.

The fluorescence emission spectrum of CCF1 before and after β-lactamase cleavage (FIG. 6) was obtained from a sample of CCF1ac₃ that had been converted to CCF1 by treatment with orange peel acetyl esterase in 50 mmolar aqueous phosphate buffer pH 7.

Substrate CCF1 has similar fluorescence properties to substrate CCF2 in Example 5. In the intact substrate, efficient energy transfer occurs from the 7-hydroxycoumarin moiety to the fluorescein moiety. Excitation of the substrate at 390 nm results in fluorescence emission at 515 nm (green) from the acceptor dye fluorescein. The energy transfer is disrupted when β-lactamase cleaves the β-lactam ring, thereby severing the link between the two dyes. Excitation of the products at 390 nm now results entirely in donor fluorescence emission at 460 nm (blue). The fluorescence emission from the donor moiety increases 25-fold upon β-lactam cleavage. The fluorescence at 515 nm is reduced by 3-fold, all of the remaining fluorescence originating from the ⁷-hydroxycoumarin 5 as its emission spectrum extends into the green. Twenty-five-fold quenching of the donor in the substrate is equivalent to an efficiency of fluorescence energy transfer of 96%. This large fluorescence change upon β-lactam cleavage can readily be used to detect β-lactamase in the cytoplasm of living mammalian cells, as is reported in Example 9.

Example 9

Cells of the T-cell lymphoma line Jurkat were suspended in an isotonic saline solution (Hank's balanced salt is solution) containing approximately 10¹² β-lactamase enzyme molecules per milliliter (approximately 1.7 nM; Penicillinase 205 TEM R⁺, from Sigma) and 1 mg/ml rhodamine conjugated to dextran (40 kd) as a marker of loading. The suspension was passed through a syringe needle (30 gauge) four times. This causes transient, survivable disruptions of the cells' plasma membrane and allows entry of labeled dextran and β-lactamase. Cells which had been successfully permeabilized contained β-lactamase and were red fluorescent when illuminated at the rhodamine excitation wavelength on a fluorescent microscope. The cells were incubated with 30 μM fluorogenic β-lactamase substrate CCF1ac₃ at room temperature for 30 minutes. Illumination with ultraviolet light (360 nm) revealed blue fluorescent and green fluorescent cells. All cells that had taken up the marker rhodamine-dextran appeared fluorescent blue, while cells devoid the enzyme appeared fluorescent green.

Example 10

The preferred membrane-permeable ester of CCF2 was prepared as follows:

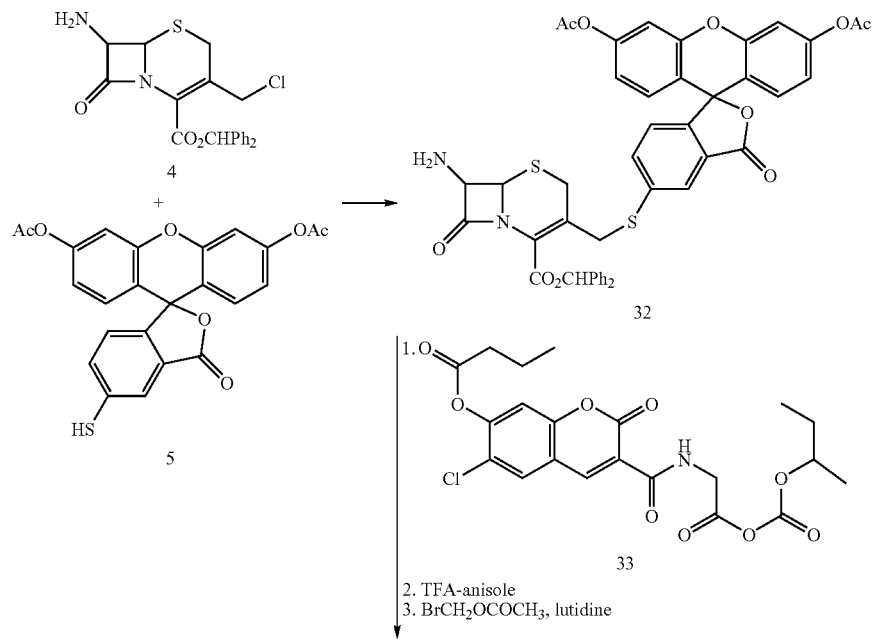

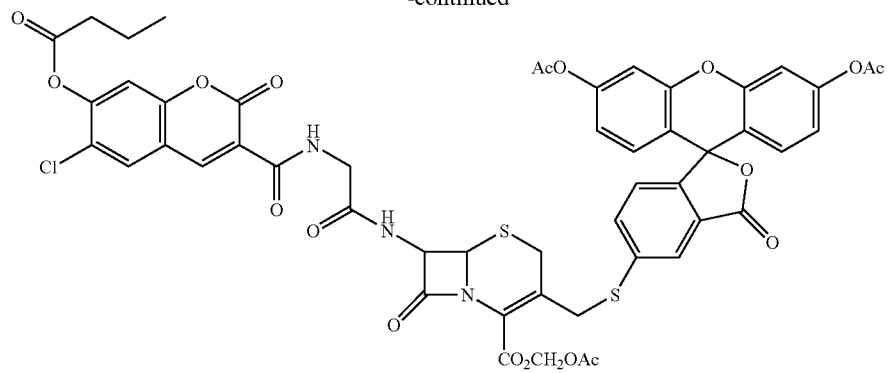

CCF2/btAMac₂    34

Coupling of 5-fluoresceinthiol diacetate (5) and 7-amino-3'-chlorocephalosporanic acid benzhydryl ester was effected as follows. 450 mg (1mmol) 5-mercaptofluorescein diacetate disulfide dimer were dissolved in 30 ml chloroform and treated with 50 μl water and 125 μl tributylphosphine in a nitrogen atmosphere which generated the free 5-fluoresceinthiol. 450 mg (1 mmol) 7-Amino-3'-chlorocephalosporanic acid benzhydryl ester hydrochloride salt were dissolved in 10 ml acetonitrile with the help of 220 μl (2 mmol) N-methyl morpholine and the two solutions combined after 30 minutes. One hour later the solvent volume was reduced to 5 ml and 50 ml carbon tetrachloride were added. The solvent volume was reduced to 15 ml and hexane added with stirring. The initial orange precipitate consisting mainly of N-methyl morpholine hydrochloride was removed by filtration. Upon further addition of two volumes of hexane 630 mg (0.76 mmol, 76%) white product was precipitated and collected.

The above product was coupled with 7-butyryloxy-3-carboxymethyl aminocarbonyl-6-chlorocoumarin. 325 mg (0.88 mmol) 7-Butyryloxy-3-carboxymethyl aminocarbonyl-6-chlorocoumarin was dissolved in 15 ml hot dry dioxane. With rapid cooling 110 μl (1 mmol) N-methyl morpholine in 1 ml dioxane and 115 μl (0.9 mmol) isobutyl chloroformate in 8 ml methylene chloride were added. The reaction was kept at 0° C. for 30 minutes after which 661 mg (0.8 mmol) of the above fluorescein-cephalosporin adduct in 7 ml dry methylene chloride were added. The solution was let to warm to room temperature and after 3 hours the solvents were removed in vaccuo. The residue was dissolved in 30 ml methylene chloride and twice extracted with one volume 10% aqueous acetic acid and once with water. The organic phase was dried over anhydrous sodium sulfate. Addition of 150 ml dry ethanol, reduction of the solvent volume to 50 ml and cooling to −20° C. resulted in precipitation of the product (crude, 850 mg). Purification was achieved by chromatography over silica gel with 25% ethyl acetate in toluene as the eluent. 250 mg (0.21 mmol, 26%) of white powderous product was collected.

Cleavage of the cephalosporin benzhydryl ester was accomplished by treatment with trifluoroacetic acid. 145 mg (0.12 mmol) of the above product was treated with trifluoroacetic acid/methylene chloride/anisole (10/10/1) at 0° C. for 20 minutes. The reagents were removed in vacuo and the residue triturated with diisopropyl ether. The solid was dissolved in 1 ml dimethyl sulfoxide and the product precipitated by addition to 25 ml water. It was further purified on reverse phase $C_{18}$ resin with a step gradient of 40 to 60% aqueous acetonitrile containing 0.5% acetic acid as the eluent yielding 74 mg (73 μmol, 60%) white powder.

Protection of cephalosporin acid as membrane permeable acetoxymethyl ester was achieved as follows. 15 mg (15 μmol) of the above product was dissolved in 250 μl methylene chloride. 25 μl Bromomethyl acetate and 50 μl lutidine were added to the solution. The reaction was kept at ambient temperature for 7 hours after which the reagents were removed in vacuo. The residue was purified by flash chromatography on silica gel with ethyl acetate as the eluent. 15 mg (14 μmol, 92%) white product was obtained. This compound, named CCF2/btAMac₂ was used for intracellular detection of β-lactamase activity.

Example 11

Measurement of activation of an intracellular receptor: Activation of the intracellular glucocorticoid receptor was measured by its ability to upregulate the transcriptional activity of the glucocorticoid responsive element in the mouse mammary tumor virus promotor. This response to steroids was detected as increased intracellular β-lactamase activity on the substrate CCF2 causing an appropriate change in fluorescent signal.

The gene for plasmid encoded RTEM β-lactamase of *Escherichia coli* without a signal sequence (Sequence 1 of FIG. 7) was put under transcriptional control of the mouse mammary tumor virus promotor and introduced into a mammalian expression vector. This vector also carried the chloramphenicol resistance marker for amplification of the plasmid in bacteria and the neomycin resistance marker for mammalian selection. It was introduced into baby hamster kidney (BHK) cells in culture using the calcium phosphate precipitation technique. Cells were then subjected to selection for stable integration of the plasmid into the cells' genome using the antibiotic G418. One of twenty clones was selected for its marked increase in β-lactamase expression following exposure to the steroid analog dexamethasone.

The following describes the measurement of the increase in β-lactamase gene expression in this clone after addition of the agonist dexamethasone. Cells of the stable BHK cell clone G941 expressing β-lactamase under control of the glucocorticoid-inducible promotor were kept in the presence or absence of the agonists in the incubator at 37° C. Flasks with cells were removed from the incubator at different intervals after agonist addition and the cells transferred into Hank's balanced salt solution containing 10 μmolar CCF2/btAMac₂. This compound becomes converted to the β-lactamase accessible fluorescent substrate CCF2 by endogenous cytoplasmic esterases. Ten minutes later the cell supernatant containing CCF2/btAMac₂ was removed. 30 Minutes later the cells were imaged with a cooled CCD camera mounted on an epi-fluorescence microscope. Fluorescence measurements were taken with violet excitation light (filter 400DF15) and with blue (filter 450DF65) and green (filter 535DF45) emission filters. A ratio of blue versus green emission intensities was determined. The ratio is a measure of how much substrate has been converted to product. Using a 40× objective, 4 fields with approximately 60 cells each were imaged at each time point. The results show a significant increase in the ratio of fluorescent intensities reflective of increasing β-lactamase expression and production.

|  | time in presence of 1 μM dexamethasone | | | |
| --- | --- | --- | --- | --- |
|  | 0.0 hours | 1.0 hours | 2.0 hours | 3.3 hours |
| average ratio of fluorescence intensities 450DF65/ 535DF45 | 0.21 +/− 0.02 | 0.38 +/− 0.05 | 0.42 +/− 0.07 | 0.47 +/− 0.08 |

Example 12

Measurement of cell surface receptor activation and intracellular signaling via second-messenger responsive elements: Activation of cell surface receptors leads to a change in intracellular messenger concentrations which in turn modulates intracellular transcription factor activity. In lymphocytes, an increase the intracellular concentration of the messenger ion calcium leads to the activation of the nuclear factor of activated T-lymphocytes (NFAT). This event increases transcription at promoters containing the NFAT-recognition site. An increase in calcium levels alone is sufficient to markedly increase transcription of a reporter gene such as β-lactamase regulated when it is put under transcriptional control of a promotor containing a trimer of NFAT sites.

The murine T-lymphocyte cell line B3Z was transiently cotransfected with two plasmids. One plasmid is contained the β-adrenergic receptor, which localizes at the cells' surface, under the transcriptional control of the strong and constitutively active cytomegalovirus (CMV) promoter. The other plasmid contained the bacterial RTEM β-lactamase gene from *Escherichia coli* modified for improved mammalian expression (sequence ID # 3 , with optimum mammalian Kozak sequence, β-globin leader sequence, pre-sequence removed) under the transcriptional control of a promoter containing a trimer of NFAT sites. The plasmids were introduced into cells using electroporation. $5 \times 10^6$ cells in 0.5 ml electroporation buffer were electroporated in the presence of 10 μg each of both plasmids using the Biorad Gene Pulser (250V, 960 μF, 16 μsec). Twenty-four hours after transfection, cells were either incubated in the presence or absence of the β-adrenergic agonist isoproterenol (10 μmolar) for 5 hours. The supernatant was removed and replaced with Hank's balanced salt solution containing 10 μmolar CCF2/btAMac$_2$. After 20 minutes at room temperature cells were washed with fresh buffer and viewed with the fluorescence microscope. 4% of isoproterenol treated cells appeared fluorescent blue (excitation filter 400DF15, emission filter 435 nm longpass) while no blue fluorescent cells were detectable in the control population (absence of agonist) Maximal stimulation with 2 μM ionomycin and 50 ng/ml phorbol ester for 5 hours resulted in 20% blue fluorescent cells in the population.

Example 13

β-Lactamases from different microorganisms were modified for use as reporter enzymes in eukaryotic cells, preferably mammalian. The bacterial gene for these enzymes includes a N-terminal pre-sequence. (first 23 amino acids of Sequence 2 of FIG. 7.) that targets the enzyme to the extracellular space. Following translocation a pre-sequence peptidase cleaves the 23 amino acid pre-sequence releasing the mature β-lactamase enzyme. RTEM β-lactamase from *Escherichia coli* including its bacterial pre-sequence (Sequence 2 of FIG. 7) was put into a mammalian expression vector under the control of the mouse mammary tumor virus promoter. This construct was introduced into baby hamster kidney cells using the standard calcium phosphate precipitation technique. The β-lactamase activity was found in the cell culture medium; no activity could be detected in the cell pellet. The amount of β-lactamase activity in the medium was steroid dependent. Cells that had been in the presence of 1 μM dexamethasone for 36 hours prior to the measurement produced threefold more enzyme than control. This makes the β-lactamase with its bacterial pre-sequence (Sequences 2 of FIG. 7) useful for an extracellular assay of mammalian reporter gene activity.

A preferred use of the β-lactamase reporter is where the enzyme is produced and retained in the cell cytoplasm. Therefore the bacterial signal sequence was removed and replaced by ATG (methionine) as the new translational start site in three modified RTEM β-lactamase genes (Sequences 1, 3, and 4 of FIG. 7). In order to increase expression of the β-lactamases in mammalian cells, the RTEM β-lactamases of Sequence 3 and 4 of FIG. 7 were constructed with altered ribosome binding sites optimized for mammalian expression [Kozak, M., *J. Cell Biol.* 108: 229-241 (1989)]. For increased compatibility with the mammalian translation machinery, β-lactamase of sequence ID #3 was inserted at the end of an untranslated mammalian β-globin leader sequence. All of these novel DNA sequences encoding novel β-lactamases were inserted into mammalian expression vectors with the cytomegalovirus promoter controlling their transcription. Mammalian cells in tissue culture (Hela, COS-7, CHO, BHK) were transfected transiently with the plasmids using the standard lipofectin technique. Two to five days after transfection, the cells were incubated with the membrane-permeant derivative, CCF2/btAMac$_2$, of the fluorescent substrate CCF2 to assay functional expression of the enzyme. 5-20% of cells transfected with plasmids containing cDNA Sequences 2, 3 and 4 of FIG. 7 showed a conversion of green to blue fluorescence indicating cleavage of the intracellularly trapped substrate by expressed β-lactamase. By contrast, in untransfected or mock transfected controls, all cells showed the green fluorescence-of uncleaved CCF2; no blue-fluorescing cells were observed, confirming the absence of any endogenous β-lactamase activity.

The gene for *Bacillus licheniformis* β-lactamase was isolated from total *Bacillus licheniformis* DNA by use of the polymerase chain reaction. The oligonucleotide primers removed the β-lactamase secretion sequence and generated the DNA sequence ID # 5. This gene was inserted in a pCDNA3 mammalian expression vector under the transcriptional control of the constitutively active cytomegalovirus promoter. HeLa cells were transfected with 10 μg of plasmid per 25 cm$^2$ culture dish using lipofectin. 5 days after transfection, cells were tested for functional expression of β-lactamase by incubating them in the presence of 100 μmolar CCF2/btAMac$_2$ and visual inspection with the epifluorescence microscope. 30-40% of cells showed blue fluorescence, whereas only green-fluorescing cells, no blue-fluorescing cells were detectable in untransfected controls. In transient transfections, it is typical for <50% of the cells to become transfected.

Example 14

A plasmid was constructed with β-lactamase of sequence ID 3 (FIG. 7) under control of yeast elongation factor EF-1alpha enhancer and promoter. This plasmid was coinjected together with the potassium salt of substrate CCF2 (compound 7b) into zebrafish embryos at the single cell stage. As control, embryos were injected with the potassium salt of substrate CCF2 alone After three hours, the embryos were viewed with an epifluorescence microscope using violet excitation light (filter 400DF15) and a 435 nm longpass emission filter. Embryos that had received plasmid DNA fluoresced blue while controls fluoresced green.

Example 15

The β-lactamase gene of sequence ID 3 was cloned into a Drosophila transformation vector under the control of the glass promotor and injected into wild-type Drosophila embryos. As control, the β-lactamase gene was inserted in the wrong orientation. Drosophila embryos were germline-transformed using P element-mediated transformation. The transformations and all subsequent fly manipulations were performed using standard techniques [Karess, R. E. and Rubin, G. M., Cell 38, 135, (1984)]. Omatidia of late stage transformed pupe were transssected and dissociated to single cells. The cells were incubated in buffer with 40 μmolar CCF2/btAMac$_2$ (compound 34) for 20 minutes, washed and viewed with an epifluorescence microscope (excitation filter 400DF15, emission filter 435 nm long pass). Omatidia cells from flyes transformed with the β-lactamase gene in the proper orientation fluoresced blue, while omatidia cells containing the gene in the wrong orientation fluoresced green.

Example 16

In certain embodiments the compound of this invention can be any of the following compounds.

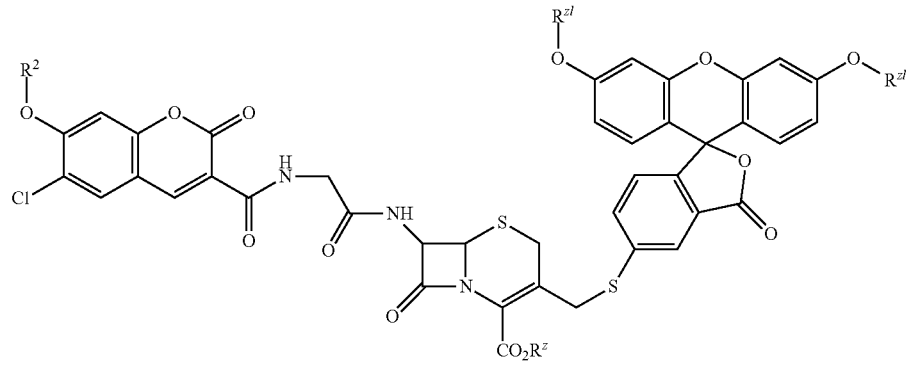

wherein
$R^Y$ is selected from the group consisting of H, Cl, and Br;
$R^X$ is selected from the group consisting of H, and methyl;
wherein $R^z$ and $R^{z1}$ are independently selected from the group consisting of —C(O)alk, —CH$_2$OC(O)alk, —CH$_2$SC(O)alk, —CH$_2$OC(O)Oalk, lower acyloxy-alpha-benzyl, and deltabutyrolactonyl; wherein alk is lower alkyl of 1 to 4 carbon atoms, and membrane-permeant fluorogenic derivatives thereof,
R" is 1-(acyloxy)alkyl.
Another example of the compound is:

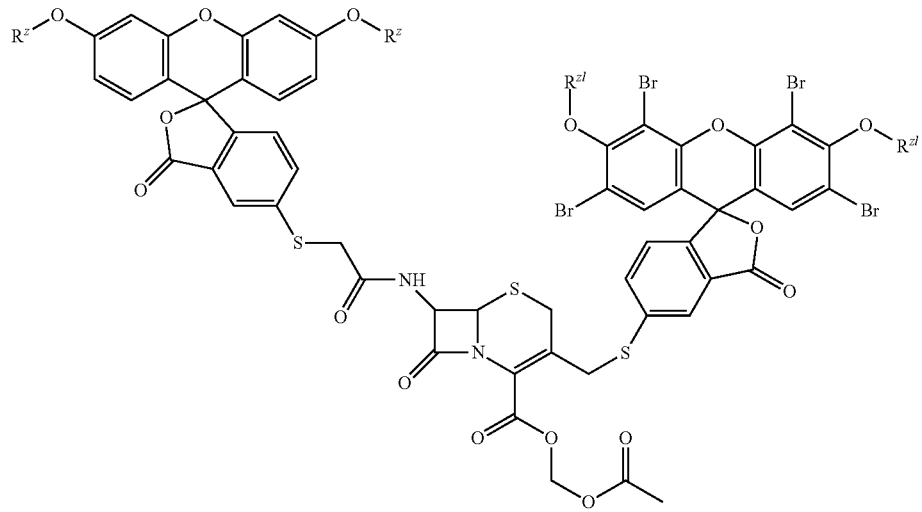

wherein $R^z$ and $R^{z1}$ are independently selected from the group consisting of —C(O)alk, —CH$_2$OC(O)alk, —CH$_2$SC(O)alk, —CH$_2$(O)alk, lower acyloxy-alpha-benzyl, and deltabutyrolactonyl; wherein alk is lower alkyl of 1 to 4 carbon atoms. Another example of the compound is:

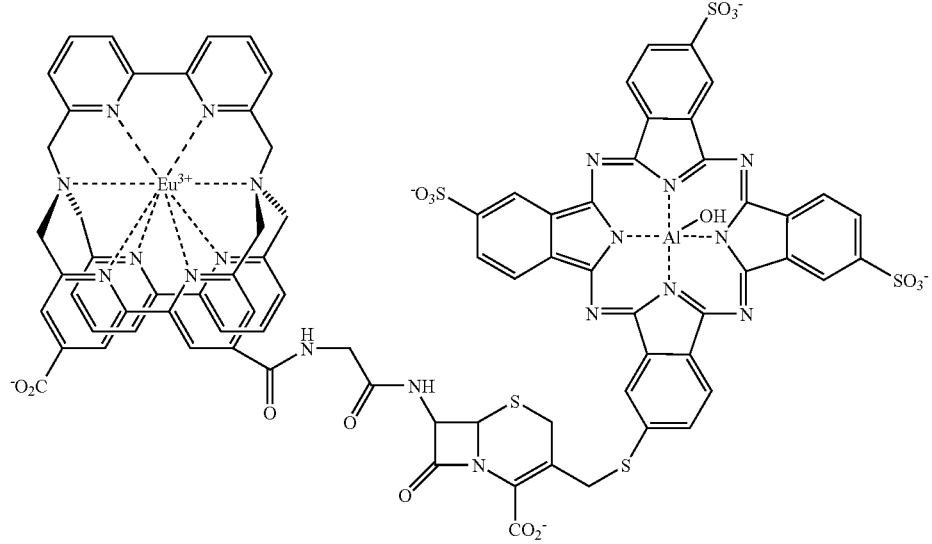

A final example of the compond is:

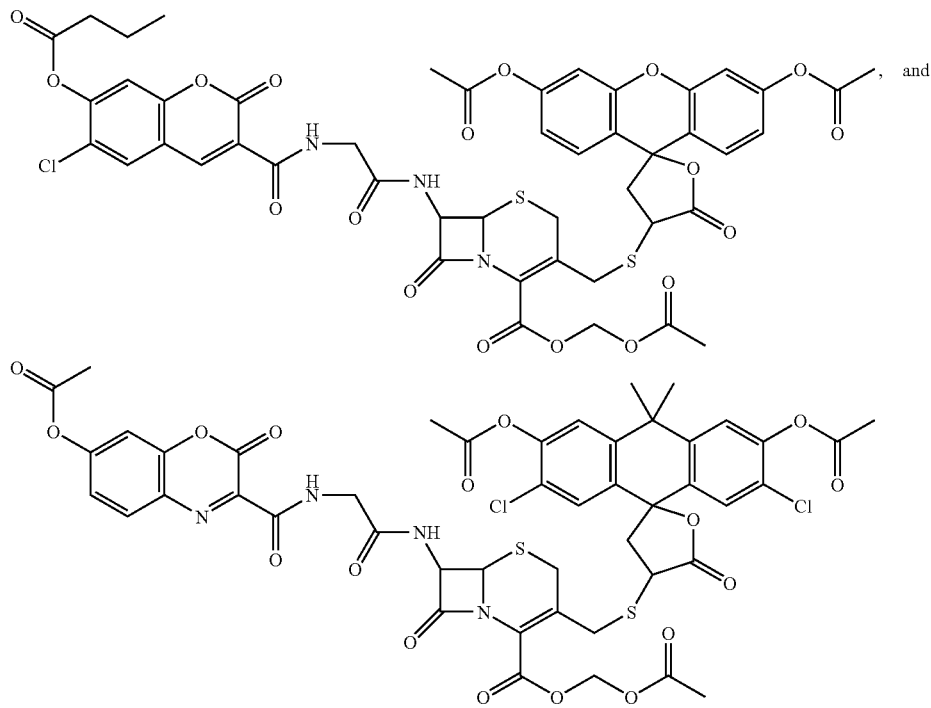

All publications and patent documents cited in this application are incorporated by reference in their entirety for all purposes to the same extent as if each individual publication or patent document were so individually denoted.

The present invention provides novel substrates for beta-lactamase, beta-lactamases and methods for their use. While specific examples have been provided, the above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted.

What is claimed is:

1. A method of preparing a fluorescent substrate for β-lactamase, said method comprising:
   providing a first fluorescent molecule having a first-reactive functional group, a second fluorescent molecule having a second-reactive functional group and a cephalosporin compound having the formula:

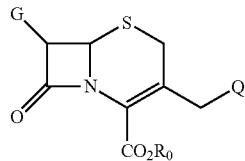

wherein G is selected from the group consisting of SH, $NH_2$, OH and a bifunctional aliphatic acid moiety;
Q is selected from the group consisting of halogen, acetate, and thiol; and
$R_0$ is selected from the group consisting of H, and a moiety that forms an ester with the $CO_2$ moiety drawn in the formula; and
contacting the cephalosporin compound with the first fluorescent molecule and the second fluorescent molecule, wherein the first-reactive functional group reacts with G and the second-reactive functional group reacts with Q to form the fluorescent substrate, wherein the first fluorescent molecule and the second fluorescent molecule are capable of operating by fluorescence resonance energy transfer.

2. The method of claim 1, wherein said first fluorescent molecule is a fluorescent donor molecule and said second fluorescent molecule is a fluorescent acceptor molecule.

3. The method of claim 1, wherein said first-reactive group is a nucleophile reactive group selected from the group consisting of carboxylic acid, iodoacetamide, isocyanate, isothiocyanate, and ester anhydride.

4. The method of claim 1, wherein said second-reactive group is a nucleophile.

5. The method of claim 4, wherein the second-reactive group is selected from the group consisting of thiol and acyl halide.

6. The method of claim 4, where Q is selected from the group consisting of chloro, acetate, and thiol.

7. The method of claim 1 wherein G is $NH_2$.

8. The method of claim 1 wherein G is the bifunctional aliphatic acid moiety.

9. The method of claim 1 wherein the bifunctional aliphatic acid moiety is an amino-, mecapto- or hydroxyalkyl acid moiety.

10. The method of claim 1 wherein $R_0$ is selected from —$CHR^2OCO(CH_2)_nCH_3$, —$CHR^2OCOC(CH_3)_3$, acylthiomethyl, acyloxy-alpha-benzyl, delta-butyrolactonyl, methoxycarbonyloxymethyl, phenyl, methylsulphinylmethyl, beta-morpholinoethyl, dialkylaminoethyl and dialkylaminocarbonyloxymethyl, in which $R^2$ is selected from the group consisting of H and lower alkyl and n is 0 or an integer selected from 1 to 5.

11. The method of claim 1 wherein $R_0$ is acyloxy-alpha-benzyl.

12. The method of claim 1 wherein $R_0$ is benzhyrdryl.

* * * * *

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
      (A) LENGTH: 795 base pairs
      (B) TYPE: nucleic acid
      (C) STRANDEDNESS: double
      (D) TOPOLOGY: linear (ii) MOLECULE TYPE: Genomic DNA (ix) FEATURE:
      (A) NAME/KEY: Coding Sequence
      (B) LOCATION: 1...795

(xi) SEQUENCE DESCRIPTION: SEQ ID NO: 1:

```
ATG AGT CAC CCA GAA ACG CTG GTG AAA GTA AAA GAT GCT GAA GAT CAG      48
Met Ser His Pro Glu Thr Leu Val Lys Val Lys Asp Ala Glu Asp Gln
 1               5                  10                  15

TTG GGT GCA CGA GTG GGT TAC ATC GAA CTG GAT CTC AAC AGC GGT AAG      96
Leu Gly Ala Arg Val Gly Tyr Ile Glu Leu Asp Leu Asn Ser Gly Lys
             20                  25                  30

ATC CTT GAG AGT TTT CGC CCC GAA GAA CGT TTT CCA ATG ATG AGC ACT     144
Ile Leu Glu Ser Phe Arg Pro Glu Glu Arg Phe Pro Met Met Ser Thr
         35                  40                  45

TTT AAA GTT CTG CTA TGT GGC GCG GTA TTA TCC CGT GTT GAC GCC GGG     192
Phe Lys Val Leu Leu Cys Gly Ala Val Leu Ser Arg Val Asp Ala Gly
     50                  55                  60

CAA GAG CAA CTC GGT CGC CGC ATA CAC TAT TCT CAG AAT GAC TTG GTT     240
Gln Glu Gln Leu Gly Arg Arg Ile His Tyr Ser Gln Asn Asp Leu Val
 65                  70                  75                  80

GAG TAC TCA CCA GTC ACA GAA AAG CAT CTT ACG GAT GGC ATG ACA GTA     288
Glu Tyr Ser Pro Val Thr Glu Lys His Leu Thr Asp Gly Met Thr Val
                 85                  90                  95

AGA GAA TTA TGC AGT GCT GCC ATA ACC ATG AGT GAT AAC ACT GCG GCC     336
Arg Glu Leu Cys Ser Ala Ala Ile Thr Met Ser Asp Asn Thr Ala Ala
            100                 105                 110

AAC TTA CTT CTG ACA ACG ATC GGA GGA CCG AAG GAG CTA ACC GCT TTT     384
Asn Leu Leu Leu Thr Thr Ile Gly Gly Pro Lys Glu Leu Thr Ala Phe
        115                 120                 125

TTG CAC AAC ATG GGG GAT CAT GTA ACT CGC CTT GAT CGT TGG GAA CCG     432
Leu His Asn Met Gly Asp His Val Thr Arg Leu Asp Arg Trp Glu Pro
    130                 135                 140

GAG CTG AAT GAA GCC ATA CCA AAC GAC GAG CGT GAC ACC ACG ATG CCT     480
Glu Leu Asn Glu Ala Ile Pro Asn Asp Glu Arg Asp Thr Thr Met Pro
145                 150                 155                 160

GCA GCA ATG GCA ACA ACG TTG CGC AAA CTA TTA ACT GGC GAA CTA CTT     528
Ala Ala Met Ala Thr Thr Leu Arg Lys Leu Leu Thr Gly Glu Leu Leu
                165                 170                 175

ACT CTA GCT TCC CGG CAA CAA TTA ATA GAC TGG ATG GAG GCG GAT AAA     576
Thr Leu Ala Ser Arg Gln Gln Leu Ile Asp Trp Met Glu Ala Asp Lys
            180                 185                 190

GTT GCA GGA CCA CTT CTG CGC TCG GCC CTT CCG GCT GGC TGG TTT ATT     624
Val Ala Gly Pro Leu Leu Arg Ser Ala Leu Pro Ala Gly Trp Phe Ile
        195                 200                 205

GCT GAT AAA TCT GGA GCC GGT GAG CGT GGG TCT CGC GGT ATC ATT GCA     672
Ala Asp Lys Ser Gly Ala Gly Glu Arg Gly Ser Arg Gly Ile Ile Ala
    210                 215                 220
```

```
GCA CTG GGG CCA GAT GGT AAG CCC TCC CGT ATC GTA GTT ATC TAC ACG      720
Ala Leu Gly Pro Asp Gly Lys Pro Ser Arg Ile Val Val Ile Tyr Thr
225                 230                 235                 240

ACG GGG AGT CAG GCA ACT ATG GAT GAA CGA AAT AGA CAG ATC GCT GAG      768
Thr Gly Ser Gln Ala Thr Met Asp Glu Arg Asn Arg Gln Ile Ala Glu
                245                 250                 255

ATA GGT GCC TCA CTG ATT AAG CAT TGG                                  795
Ile Gly Ala Ser Leu Ile Lys His Trp
260                 265
```

(2) INFORMATION FOR SEQ ID NO: 2:

(i) SEQUENCE CHARACTERISTICS:
        (A) LENGTH: 265 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 2:

```
Met Ser His Pro Glu Thr Leu Val Lys Val Lys Asp Ala Glu Asp Gln
 1               5                  10                  15

Leu Gly Ala Arg Val Gly Tyr Ile Glu Leu Asp Leu Asn Ser Gly Lys
                20                  25                  30

Ile Leu Glu Ser Phe Arg Pro Glu Arg Phe Pro Met Met Ser Thr
                35                  40                  45

Phe Lys Val Leu Leu Cys Gly Ala Val Leu Ser Arg Val Asp Ala Gly
    50                  55                  60

Gln Glu Gln Leu Gly Arg Arg Ile His Tyr Ser Gln Asn Asp Leu Val
65                  70                  75                  80

Glu Tyr Ser Pro Val Thr Glu Lys His Leu Thr Asp Gly Met Thr Val
                85                  90                  95

Arg Glu Leu Cys Ser Ala Ala Ile Thr Met Ser Asp Asn Thr Ala Ala
                100                 105                 110

Asn Leu Leu Leu Thr Thr Ile Gly Gly Pro Lys Glu Leu Thr Ala Phe
            115                 120                 125

Leu His Asn Met Gly Asp His Val Thr Arg Leu Asp Arg Trp Glu Pro
        130                 135                 140

Glu Leu Asn Glu Ala Ile Pro Asn Asp Glu Arg Asp Thr Thr Met Pro
145                 150                 155                 160

Ala Ala Met Ala Thr Thr Leu Arg Lys Leu Leu Thr Gly Glu Leu Leu
                165                 170                 175

Thr Leu Ala Ser Arg Gln Gln Leu Ile Asp Trp Met Glu Ala Asp Lys
            180                 185                 190

Val Ala Gly Pro Leu Leu Arg Ser Ala Leu Pro Ala Gly Trp Phe Ile
        195                 200                 205

Ala Asp Lys Ser Gly Ala Gly Glu Arg Gly Ser Arg Gly Ile Ile Ala
        210                 215                 220

Ala Leu Gly Pro Asp Gly Lys Pro Ser Arg Ile Val Val Ile Tyr Thr
225                 230                 235                 240

Thr Gly Ser Gln Ala Thr Met Asp Glu Arg Asn Arg Gln Ile Ala Glu
                245                 250                 255

Ile Gly Ala Ser Leu Ile Lys His Trp
                260                 265
```

(2) INFORMATION FOR SEQ ID NO: 3:

(i) SEQUENCE CHARACTERISTICS:
  (A) LENGTH: 858 base pairs
  (B) TYPE: nucleic acid
  (C) STRANDEDNESS: double
  (D) TOPOLOGY: linear (ii) MOLECULE TYPE: Genomic DNA (ix) FEATURE:
  (A) NAME/KEY: Coding Sequence
  (B) LOCATION: 1...858

(xi) SEQUENCE DESCRIPTION: SEQ ID NO: 3:

| | | | | | | | | | | | | | | | | |
|---|---|---|---|---|---|---|---|---|---|---|---|---|---|---|---|---|
| ATG | AGA | ATT | CAA | CAT | TTC | CGT | GTC | GCC | CTT | ATT | CCC | TTT | TTT | GCG | GCA | 48 |
| Met | Arg | Ile | Gln | His | Phe | Arg | Val | Ala | Leu | Ile | Pro | Phe | Phe | Ala | Ala | |
| 1 | | | | 5 | | | | | 10 | | | | | 15 | | |
| TTT | TGC | CTT | CCT | GTT | TTT | GGT | CAC | CCA | GAA | ACG | CTG | GTG | AAA | GTA | AAA | 96 |
| Phe | Cys | Leu | Pro | Val | Phe | Gly | His | Pro | Glu | Thr | Leu | Val | Lys | Val | Lys | |
| | | | 20 | | | | | 25 | | | | | 30 | | | |
| GAT | GCT | GAA | GAT | CAG | TTG | GGT | GCA | CGA | GTG | GGT | TAC | ATC | GAA | CTG | GAT | 144 |
| Asp | Ala | Glu | Asp | Gln | Leu | Gly | Ala | Arg | Val | Gly | Tyr | Ile | Glu | Leu | Asp | |
| | | | | 35 | | | | | 40 | | | | | 45 | | |
| CTC | AAC | AGC | GGT | AAG | ATC | CTT | GAG | AGT | TTT | CGC | CCC | GAA | GAA | CGT | TTT | 192 |
| Leu | Asn | Ser | Gly | Lys | Ile | Leu | Glu | Ser | Phe | Arg | Pro | Glu | Glu | Arg | Phe | |
| | | 50 | | | | | 55 | | | | | 60 | | | | |
| CCA | ATG | ATG | AGC | ACT | TTT | AAA | GTT | CTG | CTA | TGT | GGC | GCG | GTA | TTA | TCC | 240 |
| Pro | Met | Met | Ser | Thr | Phe | Lys | Val | Leu | Leu | Cys | Gly | Ala | Val | Leu | Ser | |
| 65 | | | | | 70 | | | | | 75 | | | | | 80 | |
| CGT | GTT | GAC | GCC | GGG | CAA | GAG | CAA | CTC | GGT | CGC | CGC | ATA | CAC | TAT | TCT | 288 |
| Arg | Val | Asp | Ala | Gly | Gln | Glu | Gln | Leu | Gly | Arg | Arg | Ile | His | Tyr | Ser | |
| | | | | 85 | | | | | 90 | | | | | 95 | | |
| CAG | AAT | GAC | TTG | GTT | GAG | TAC | TCA | CCA | GTC | ACA | GAA | AAG | CAT | CTT | ACG | 336 |
| Gln | Asn | Asp | Leu | Val | Glu | Tyr | Ser | Pro | Val | Thr | Glu | Lys | His | Leu | Thr | |
| | | | 100 | | | | | 105 | | | | | 110 | | | |
| GAT | GGC | ATG | ACA | GTA | AGA | GAA | TTA | TGC | AGT | GCT | GCC | ATA | ACC | ATG | AGT | 384 |
| Asp | Gly | Met | Thr | Val | Arg | Glu | Leu | Cys | Ser | Ala | Ala | Ile | Thr | Met | Ser | |
| | | 115 | | | | | 120 | | | | | 125 | | | | |
| GAT | AAC | ACT | GCG | GCC | AAC | TTA | CTT | CTG | ACA | ACG | ATC | GGA | GGA | CCG | AAG | 432 |
| Asp | Asn | Thr | Ala | Ala | Asn | Leu | Leu | Leu | Thr | Thr | Ile | Gly | Gly | Pro | Lys | |
| 130 | | | | | 135 | | | | | 140 | | | | | | |
| GAG | CTA | ACC | GCT | TTT | TTG | CAC | AAC | ATG | GGG | GAT | CAT | GTA | ACT | CGC | CTT | 480 |
| Glu | Leu | Thr | Ala | Phe | Leu | His | Asn | Met | Gly | Asp | His | Val | Thr | Arg | Leu | |
| 145 | | | | | 150 | | | | | 155 | | | | | 160 | |
| GAT | CGT | TGG | GAA | CCG | GAG | CTG | AAT | GAA | GCC | ATA | CCA | AAC | GAC | GAG | CGT | 528 |
| Asp | Arg | Trp | Glu | Pro | Glu | Leu | Asn | Glu | Ala | Ile | Pro | Asn | Asp | Glu | Arg | |
| | | | | 165 | | | | | 170 | | | | | 175 | | |
| GAC | ACC | ACG | ATG | CCT | GCA | GCA | ATG | GCA | ACA | ACG | TTG | CGC | AAA | CTA | TTA | 576 |
| Asp | Thr | Thr | Met | Pro | Ala | Ala | Met | Ala | Thr | Thr | Leu | Arg | Lys | Leu | Leu | |
| | | | 180 | | | | | 185 | | | | | 190 | | | |
| ACT | GGC | GAA | CTA | CTT | ACT | CTA | GCT | TCC | CGG | CAA | CAA | TTA | ATA | GAC | TGG | 624 |
| Thr | Gly | Glu | Leu | Leu | Thr | Leu | Ala | Ser | Arg | Gln | Gln | Leu | Ile | Asp | Trp | |
| | | 195 | | | | | 200 | | | | | 205 | | | | |
| ATG | GAG | GCG | GAT | AAA | GTT | GCA | GGA | CCA | CTT | CTG | CGC | TCG | GCC | CTT | CCG | 672 |
| Met | Glu | Ala | Asp | Lys | Val | Ala | Gly | Pro | Leu | Leu | Arg | Ser | Ala | Leu | Pro | |
| 210 | | | | | 215 | | | | | 220 | | | | | | |
| GCT | GGC | TGG | TTT | ATT | GCT | GAT | AAA | TCT | GGA | GCC | GGT | GAG | CGT | GGG | TCT | 720 |
| Ala | Gly | Trp | Phe | Ile | Ala | Asp | Lys | Ser | Gly | Ala | Gly | Glu | Arg | Gly | Ser | |
| 225 | | | | | 230 | | | | | 235 | | | | | 240 | |
| CGC | GGT | ATC | ATT | GCA | GCA | CTG | GGG | CCA | GAT | GGT | AAG | CCC | TCC | CGT | ATC | 768 |
| Arg | Gly | Ile | Ile | Ala | Ala | Leu | Gly | Pro | Asp | Gly | Lys | Pro | Ser | Arg | Ile | |
| | | | | 245 | | | | | 250 | | | | | 255 | | |
| GTA | GTT | ATC | TAC | ACG | ACG | GGG | AGT | CAG | GCA | ACT | ATG | GAT | GAA | CGA | AAT | 816 |
| Val | Val | Ile | Tyr | Thr | Thr | Gly | Ser | Gln | Ala | Thr | Met | Asp | Glu | Arg | Asn | |

-continued

```
                    260                 265                 270
AGA CAG ATC GCT GAG ATA GGT GCC TCA CTG ATT AAG CAT TGG              858
Arg Gln Ile Ala Glu Ile Gly Ala Ser Leu Ile Lys His Trp
            275                 280                 285
```

(2) INFORMATION FOR SEQ ID NO: 4:

(i) SEQUENCE CHARACTERISTICS:
        (A) LENGTH: 286 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 4:

```
Met Arg Ile Gln His Phe Arg Val Ala Leu Ile Pro Phe Phe Ala Ala
 1               5                  10                  15

Phe Cys Leu Pro Val Phe Gly His Pro Glu Thr Leu Val Lys Val Lys
                20                  25                  30

Asp Ala Glu Asp Gln Leu Gly Ala Arg Val Gly Tyr Ile Glu Leu Asp
            35                  40                  45

Leu Asn Ser Gly Lys Ile Leu Glu Ser Phe Arg Pro Glu Glu Arg Phe
        50                  55                  60

Pro Met Met Ser Thr Phe Lys Val Leu Leu Cys Gly Ala Val Leu Ser
 65                  70                  75                  80

Arg Val Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Ala Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285
```

(2) INFORMATION FOR SEQ ID NO: 5:

(i) SEQUENCE CHARACTERISTICS:
        (A) LENGTH: 843 base pairs
        (B) TYPE: nucleic acid (C) STRANDEDNESS: double
        (D) TOPOLOGY: linear (ii) MOLECULE TYPE: Genomic DNA (ix) FEATURE:
        (A) NAME/KEY: Coding Sequence
        (B) LOCATION: 49...843

(xi) SEQUENCE DESCRIPTION: SEQ ID NO: 5:

```
AAGCTTTTTG CAGAAGCTCA GAATAAACGC AACTTTCCGG GTACCACC ATG GGG CAC          57
                                                      Met Gly His
                                                        1

CCA GAA ACG CTG GTG AAA GTA AAA GAT GCT GAA GAT CAG TTG GGT GCA         105
Pro Glu Thr Leu Val Lys Val Lys Asp Ala Glu Asp Gln Leu Gly Ala
          5                  10                  15

CGA GTG GGT TAC ATC GAA CTG GAT CTC AAC AGC GGT AAG ATC CTT GAG         153
Arg Val Gly Tyr Ile Glu Leu Asp Leu Asn Ser Gly Lys Ile Leu Glu
 20                  25                  30                  35

AGT TTT CGC CCC GAA GAA CGT TTT CCA ATG ATG AGC ACT TTT AAA GTT         201
Ser Phe Arg Pro Glu Glu Arg Phe Pro Met Met Ser Thr Phe Lys Val
                 40                  45                  50

CTG CTA TGT GGC GCG GTA TTA TCC CGT GAT GAC GCC GGG CAA GAG CAA         249
Leu Leu Cys Gly Ala Val Leu Ser Arg Asp Asp Ala Gly Gln Glu Gln
             55                  60                  65

CTC GGT CGC CGC ATA CAC TAT TCT CAG AAT GAC TTG GTT GAG TAC TCA         297
Leu Gly Arg Arg Ile His Tyr Ser Gln Asn Asp Leu Val Glu Tyr Ser
         70                  75                  80

CCA GTC ACA GAA AAG CAT CTT ACG GAT GGC ATG ACA GTA AGA GAA TTA         345
Pro Val Thr Glu Lys His Leu Thr Asp Gly Met Thr Val Arg Glu Leu
     85                  90                  95

TGC AGT GCT GCC ATA ACC ATG AGT GAT AAC ACT GCG GCC AAC TTA CTT         393
Cys Ser Ala Ala Ile Thr Met Ser Asp Asn Thr Ala Ala Asn Leu Leu
100                 105                 110                 115

CTG ACA ACG ATC GGA GGA CCG AAG GAG CTA ACC GCT TTT TTG CAC AAC         441
Leu Thr Thr Ile Gly Gly Pro Lys Glu Leu Thr Ala Phe Leu His Asn
                120                 125                 130

ATG GGG GAT CAT GTA ACT CGC CTT GAT CAT TGG GAA CCG GAG CTG AAT         489
Met Gly Asp His Val Thr Arg Leu Asp His Trp Glu Pro Glu Leu Asn
            135                 140                 145

GAA GCC ATA CCA AAC GAC GAG CGT GAC ACC ACG ATG CCT GTA GCA ATG         537
Glu Ala Ile Pro Asn Asp Glu Arg Asp Thr Thr Met Pro Val Ala Met
        150                 155                 160

GCA ACA ACG TTG CGC AAA CTA TTA ACT GGC GAA CTA CTT ACT CTA GCT         585
Ala Thr Thr Leu Arg Lys Leu Leu Thr Gly Glu Leu Leu Thr Leu Ala
    165                 170                 175

TCC CGG CAA CAA TTA ATA GAC TGG ATG GAG GCG GAT AAA GTT GCA GGA         633
Ser Arg Gln Gln Leu Ile Asp Trp Met Glu Ala Asp Lys Val Ala Gly
180                 185                 190                 195

CCA CTT CTG CGC TCG GCC CTT CCG GCT GGC TGG TTT ATT GCT GAT AAA         681
Pro Leu Leu Arg Ser Ala Leu Pro Ala Gly Trp Phe Ile Ala Asp Lys
                200                 205                 210

TCT GGA GCC GGT GAG CGT GGG TCT CGC GGT ATC ATT GCA GCA CTG GGG         729
Ser Gly Ala Gly Glu Arg Gly Ser Arg Gly Ile Ile Ala Ala Leu Gly
            215                 220                 225

CCA GAT GGT AAG CCC TCC CGT ATC GTA GTT ATC TAC ACG ACG GGG AGT         777
Pro Asp Gly Lys Pro Ser Arg Ile Val Val Ile Tyr Thr Thr Gly Ser
        230                 235                 240

CAG GCA ACT ATG GAT GAA CGA AAT AGA CAG ATC GCT GAG ATA GGT GCC         825
Gln Ala Thr Met Asp Glu Arg Asn Arg Gln Ile Ala Glu Ile Gly Ala
    245                 250                 255

TCA CTG ATT AAG CAT TGG                                                 843
```

```
Ser Leu Ile Lys His Trp
260             265

(2) INFORMATION FOR SEQ ID NO: 6:

(i) SEQUENCE CHARACTERISTICS:
        (A) LENGTH: 265 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 6:

Met Gly His Pro Glu Thr Leu Val Lys Val Lys Asp Ala Glu Asp Gln
1               5                   10                  15

Leu Gly Ala Arg Val Gly Tyr Ile Glu Leu Asp Leu Asn Ser Gly Lys
            20                  25                  30

Ile Leu Glu Ser Phe Arg Pro Glu Glu Arg Phe Pro Met Met Ser Thr
        35                  40                  45

Phe Lys Val Leu Leu Cys Gly Ala Val Leu Ser Arg Asp Asp Ala Gly
    50                  55                  60

Gln Glu Gln Leu Gly Arg Arg Ile His Tyr Ser Gln Asn Asp Leu Val
65                  70                  75                  80

Glu Tyr Ser Pro Val Thr Glu Lys His Leu Thr Asp Gly Met Thr Val
                85                  90                  95

Arg Glu Leu Cys Ser Ala Ala Ile Thr Met Ser Asp Asn Thr Ala Ala
            100                 105                 110

Asn Leu Leu Leu Thr Thr Ile Gly Gly Pro Lys Glu Leu Thr Ala Phe
        115                 120                 125

Leu His Asn Met Gly Asp His Val Thr Arg Leu Asp His Trp Glu Pro
    130                 135                 140

Glu Leu Asn Glu Ala Ile Pro Asn Asp Glu Arg Asp Thr Thr Met Pro
145                 150                 155                 160

Val Ala Met Ala Thr Thr Leu Arg Lys Leu Leu Thr Gly Glu Leu Leu
                165                 170                 175

Thr Leu Ala Ser Arg Gln Gln Leu Ile Asp Trp Met Glu Ala Asp Lys
            180                 185                 190

Val Ala Gly Pro Leu Leu Arg Ser Ala Leu Pro Ala Gly Trp Phe Ile
        195                 200                 205

Ala Asp Lys Ser Gly Ala Gly Glu Arg Gly Ser Arg Gly Ile Ile Ala
    210                 215                 220

Ala Leu Gly Pro Asp Gly Lys Pro Ser Arg Ile Val Val Ile Tyr Thr
225                 230                 235                 240

Thr Gly Ser Gln Ala Thr Met Asp Glu Arg Asn Arg Gln Ile Ala Glu
                245                 250                 255

Ile Gly Ala Ser Leu Ile Lys His Trp
            260                 265

(2) INFORMATION FOR SEQ ID NO: 7:

(i) SEQUENCE CHARACTERISTICS:
        (A) LENGTH: 792 base pairs
        (B) TYPE: nucleic acid
        (C) STRANDEDNESS: double
        (D) TOPOLOGY: linear (ii) MOLECULE TYPE: Genomic DNA (ix) FEATURE:
```

(A) NAME/KEY: Coding Sequence
        (B) LOCATION: 1...792

(xi) SEQUENCE DESCRIPTION: SEQ ID NO: 7:

```
ATG GAC CCA GAA ACG CTG GTG AAA GTA AAA GAT GCT GAA GAT CAG TTG        48
Met Asp Pro Glu Thr Leu Val Lys Val Lys Asp Ala Glu Asp Gln Leu
 1               5                  10                  15

GGT GCA CGA GTG GGT TAC ATC GAA CTG GAT CTC AAC AGC GGT AAG ATC        96
Gly Ala Arg Val Gly Tyr Ile Glu Leu Asp Leu Asn Ser Gly Lys Ile
                20                  25                  30

CTT GAG AGT TTT CGC CCC GAA GAA CGT TTT CCA ATG ATG AGC ACT TTT       144
Leu Glu Ser Phe Arg Pro Glu Glu Arg Phe Pro Met Met Ser Thr Phe
             35                  40                  45

AAA GTT CTG CTA TGT GGC GCG GTA TTA TCC CGT ATT GAC GCC GGG CAA       192
Lys Val Leu Leu Cys Gly Ala Val Leu Ser Arg Ile Asp Ala Gly Gln
         50                  55                  60

GAG CAA CTC GGT CGC CGC ATA CAC TAT TCT CAG AAT GAC TTG GTT GAG       240
Glu Gln Leu Gly Arg Arg Ile His Tyr Ser Gln Asn Asp Leu Val Glu
 65                  70                  75                  80

TAC TCA CCA GTC ACA GAA AAG CAT CTT ACG GAT GGC ATG ACA GTA AGA       288
Tyr Ser Pro Val Thr Glu Lys His Leu Thr Asp Gly Met Thr Val Arg
                 85                  90                  95

GAA TTA TGC AGT GCT GCC ATA ACC ATG AGT GAT AAC ACT GCG GCC AAC       336
Glu Leu Cys Ser Ala Ala Ile Thr Met Ser Asp Asn Thr Ala Ala Asn
                100                 105                 110

TTA CTT CTG ACA ACG ATC GGA GGA CCG AAG GAG CTA ACC GCT TTT TTG       384
Leu Leu Leu Thr Thr Ile Gly Gly Pro Lys Glu Leu Thr Ala Phe Leu
            115                 120                 125

CAC AAC ATG GGG GAT CAT GTA ACT CGC CTT GAT CAT TGG GAA CCG GAG       432
His Asn Met Gly Asp His Val Thr Arg Leu Asp His Trp Glu Pro Glu
        130                 135                 140

CTG AAT GAA GCC ATA CCA AAC GAC GAG CGT GAC ACC ACG ATG CCT GTA       480
Leu Asn Glu Ala Ile Pro Asn Asp Glu Arg Asp Thr Thr Met Pro Val
145                 150                 155                 160

GCA ATG GCA ACA ACG TTG CGC AAA CTA TTA ACT GGC GAA CTA CTT ACT       528
Ala Met Ala Thr Thr Leu Arg Lys Leu Leu Thr Gly Glu Leu Leu Thr
                165                 170                 175

CTA GCT TCC CGG CAA CAA TTA ATA GAC TGG ATG GAG GCG GAT AAA GTT       576
Leu Ala Ser Arg Gln Gln Leu Ile Asp Trp Met Glu Ala Asp Lys Val
            180                 185                 190

GCA GGA CCA CTT CTG CGC TCG GCC CTT CCG GCT GGC TGG TTT ATT GCT       624
Ala Gly Pro Leu Leu Arg Ser Ala Leu Pro Ala Gly Trp Phe Ile Ala
        195                 200                 205

GAT AAA TCT GGA GCC GGT GAG CGT GGG TCT CGC GGT ATC ATT GCA GCA       672
Asp Lys Ser Gly Ala Gly Glu Arg Gly Ser Arg Gly Ile Ile Ala Ala
        210                 215                 220

CTG GGG CCA GAT GGT AAG CCC TCC CGT ATC GTA GTT ATC TAC ACG ACG       720
Leu Gly Pro Asp Gly Lys Pro Ser Arg Ile Val Val Ile Tyr Thr Thr
225                 230                 235                 240

GGG AGT CAG GCA ACT ATG GAT GAA CGA AAT AGA CAG ATC GCT GAG ATA       768
Gly Ser Gln Ala Thr Met Asp Glu Arg Asn Arg Gln Ile Ala Glu Ile
                245                 250                 255

GGT GCC TCA CTG ATT AAG CAT TGG                                       792
Gly Ala Ser Leu Ile Lys His Trp
            260
```

(2) INFORMATION FOR SEQ ID NO: 8:

(i) SEQUENCE CHARACTERISTICS:
        (A) LENGTH: 264 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 8:

Met Asp Pro Glu Thr Leu Val Lys Val Lys Asp Ala Glu Asp Gln Leu
1               5                   10                  15

Gly Ala Arg Val Gly Tyr Ile Glu Leu Asp Leu Asn Ser Gly Lys Ile
                20                  25                  30

Leu Glu Ser Phe Arg Pro Glu Glu Arg Phe Pro Met Met Ser Thr Phe
            35                  40                  45

Lys Val Leu Leu Cys Gly Ala Val Leu Ser Arg Ile Asp Ala Gly Gln
50                  55                  60

Glu Gln Leu Gly Arg Arg Ile His Tyr Ser Gln Asn Asp Leu Val Glu
65                  70                  75                  80

Tyr Ser Pro Val Thr Glu Lys His Leu Thr Asp Gly Met Thr Val Arg
                85                  90                  95

Glu Leu Cys Ser Ala Ala Ile Thr Met Ser Asp Asn Thr Ala Ala Asn
                100                 105                 110

Leu Leu Leu Thr Thr Ile Gly Gly Pro Lys Glu Leu Thr Ala Phe Leu
            115                 120                 125

His Asn Met Gly Asp His Val Thr Arg Leu Asp His Trp Glu Pro Glu
130                 135                 140

Leu Asn Glu Ala Ile Pro Asn Asp Glu Arg Asp Thr Thr Met Pro Val
145                 150                 155                 160

Ala Met Ala Thr Thr Leu Arg Lys Leu Leu Thr Gly Glu Leu Leu Thr
                165                 170                 175

Leu Ala Ser Arg Gln Gln Leu Ile Asp Trp Met Glu Ala Asp Lys Val
                180                 185                 190

Ala Gly Pro Leu Leu Arg Ser Ala Leu Pro Ala Gly Trp Phe Ile Ala
            195                 200                 205

Asp Lys Ser Gly Ala Gly Glu Arg Gly Ser Arg Gly Ile Ile Ala Ala
210                 215                 220

Leu Gly Pro Asp Gly Lys Pro Ser Arg Ile Val Val Ile Tyr Thr Thr
225                 230                 235                 240

Gly Ser Gln Ala Thr Met Asp Glu Arg Asn Arg Gln Ile Ala Glu Ile
                245                 250                 255

Gly Ala Ser Leu Ile Lys His Trp
            260

(2) INFORMATION FOR SEQ ID NO: 9:

(i) SEQUENCE CHARACTERISTICS:
            (A) LENGTH: 786 base pairs
            (B) TYPE: nucleic acid
            (C) STRANDEDNESS: double
            (D) TOPOLOGY: linear (ii) MOLECULE TYPE: Genomic DNA (ix) FEATURE:
            (A) NAME/KEY: Coding Sequence
            (B) LOCATION: 1...786

(xi) SEQUENCE DESCRIPTION: SEQ ID NO: 9:

ATG AAA GAT GAT TTT GCA AAA CTT GAG GAA CAA TTT GAT GCA AAA CTC         48
Met Lys Asp Asp Phe Ala Lys Leu Glu Glu Gln Phe Asp Ala Lys Leu
1               5                   10                  15

GGG ATC TTT GCA TTG GAT ACA GGT ACA AAC CGG ACG GTA GCG TAT CGG         96

```
Gly Ile Phe Ala Leu Asp Thr Gly Thr Asn Arg Thr Val Ala Tyr Arg
            20                  25                  30

CCG GAT GAG CGT TTT GCT TTT GCT TCG ACG ATT AAG GCT TTA ACT GTA         144
Pro Asp Glu Arg Phe Ala Phe Ala Ser Thr Ile Lys Ala Leu Thr Val
        35                  40                  45

GGC GTG CTT TTG CAA CAG AAA TCA ATA GAA GAT CTG AAC CAG AGA ATA         192
Gly Val Leu Leu Gln Gln Lys Ser Ile Glu Asp Leu Asn Gln Arg Ile
    50                  55                  60

ACA TAT ACA CGT GAT GAT CTT GTA AAC TAC AAC CCG ATT ACG GAA AAG         240
Thr Tyr Thr Arg Asp Asp Leu Val Asn Tyr Asn Pro Ile Thr Glu Lys
65                  70                  75                  80

CAC GTT GAT ACG GGA ATG ACG CTC AAA GAG CTT GCG GAT GCT TCG CTT         288
His Val Asp Thr Gly Met Thr Leu Lys Glu Leu Ala Asp Ala Ser Leu
                85                  90                  95

CGA TAT AGT GAC AAT GCG GCA CAG AAT CTC ATT CTT AAA CAA ATT GGC         336
Arg Tyr Ser Asp Asn Ala Ala Gln Asn Leu Ile Leu Lys Gln Ile Gly
            100                 105                 110

GGA CCT GAA AGT TTG AAA AAG GAA CTG AGG AAG ATT GGT GAT GAG GTT         384
Gly Pro Glu Ser Leu Lys Lys Glu Leu Arg Lys Ile Gly Asp Glu Val
        115                 120                 125

ACA AAT CCC GAA CGA TTC GAA CCA GAG TTA AAT GAA GTG AAT CCG GGT         432
Thr Asn Pro Glu Arg Phe Glu Pro Glu Leu Asn Glu Val Asn Pro Gly
    130                 135                 140

GAA ACT CAG GAT ACC AGT ACA GCA AGA GCA CTT GTC ACA AGC CTT CGA         480
Glu Thr Gln Asp Thr Ser Thr Ala Arg Ala Leu Val Thr Ser Leu Arg
145                 150                 155                 160

GCC TTT GCT CTT GAA GAT AAA CTT CCA AGT GAA AAA CGC GAG CTT TTA         528
Ala Phe Ala Leu Glu Asp Lys Leu Pro Ser Glu Lys Arg Glu Leu Leu
                165                 170                 175

ATC GAT TGG ATG AAA CGA AAT ACC ACT GGA GAC GCC TTA ATC CGT GCC         576
Ile Asp Trp Met Lys Arg Asn Thr Thr Gly Asp Ala Leu Ile Arg Ala
            180                 185                 190

GGA GCG GCA TCA TAT GGA ACC CGG AAT GAC ATT GCC ATC ATT TGG CCG         624
Gly Ala Ala Ser Tyr Gly Thr Arg Asn Asp Ile Ala Ile Ile Trp Pro
        195                 200                 205

CCA AAA GGA GAT CCT GTC GGT GTG CCG GAC GGT TGG GAA GTG GCT GAT         672
Pro Lys Gly Asp Pro Val Gly Val Pro Asp Gly Trp Glu Val Ala Asp
    210                 215                 220

AAA ACT GTT CTT GCA GTA TTA TCC AGC AGG GAT AAA AAG GAC GCC AAG         720
Lys Thr Val Leu Ala Val Leu Ser Ser Arg Asp Lys Lys Asp Ala Lys
225                 230                 235                 240

TAT GAT GAT AAA CTT ATT GCA GAG GCA ACA AAG GTG GTA ATG AAA GCC         768
Tyr Asp Asp Lys Leu Ile Ala Glu Ala Thr Lys Val Val Met Lys Ala
                245                 250                 255

TTA AAC ATG AAC GGC AAA                                                 786
Leu Asn Met Asn Gly Lys
            260

(2) INFORMATION FOR SEQ ID NO: 10:

(i) SEQUENCE CHARACTERISTICS:
        (A) LENGTH: 262 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 10:

Met Lys Asp Asp Phe Ala Lys Leu Glu Glu Gln Phe Asp Ala Lys Leu
1               5                   10                  15
```

```
Gly Ile Phe Ala Leu Asp Thr Gly Thr Asn Arg Thr Val Ala Tyr Arg
            20                  25                  30

Pro Asp Glu Arg Phe Ala Phe Ala Ser Thr Ile Lys Ala Leu Thr Val
        35                  40                  45

Gly Val Leu Leu Gln Gln Lys Ser Ile Glu Asp Leu Asn Gln Arg Ile
    50                  55                  60

Thr Tyr Thr Arg Asp Asp Leu Val Asn Tyr Asn Pro Ile Thr Glu Lys
65                      70                  75                  80

His Val Asp Thr Gly Met Thr Leu Lys Glu Leu Ala Asp Ala Ser Leu
                85                  90                  95

Arg Tyr Ser Asp Asn Ala Ala Gln Asn Leu Ile Leu Lys Gln Ile Gly
            100                 105                 110

Gly Pro Glu Ser Leu Lys Lys Glu Leu Arg Lys Ile Gly Asp Glu Val
            115                 120                 125

Thr Asn Pro Glu Arg Phe Glu Pro Glu Leu Asn Glu Val Asn Pro Gly
    130                 135                 140

Glu Thr Gln Asp Thr Ser Thr Ala Arg Ala Leu Val Thr Ser Leu Arg
145                 150                 155                 160

Ala Phe Ala Leu Glu Asp Lys Leu Pro Ser Glu Lys Arg Glu Leu Leu
                165                 170                 175

Ile Asp Trp Met Lys Arg Asn Thr Thr Gly Asp Ala Leu Ile Arg Ala
            180                 185                 190

Gly Ala Ala Ser Tyr Gly Thr Arg Asn Asp Ile Ala Ile Ile Trp Pro
            195                 200                 205

Pro Lys Gly Asp Pro Val Gly Val Pro Asp Gly Trp Glu Val Ala Asp
    210                 215                 220

Lys Thr Val Leu Ala Val Leu Ser Ser Arg Asp Lys Lys Asp Ala Lys
225                 230                 235                 240

Tyr Asp Asp Lys Leu Ile Ala Glu Ala Thr Lys Val Val Met Lys Ala
            245                 250                 255

Leu Asn Met Asn Gly Lys
            260
```